(12) United States Patent
Kong et al.

(10) Patent No.: US 8,372,844 B2
(45) Date of Patent: *Feb. 12, 2013

(54) PIPERAZINYL-PROPYL-PYRAZOLE DERIVATIVES AS DOPAMINE D4 RECEPTOR ANTAGONISTS, AND PHARMACEUTICAL COMPOSITIONS CONTAINING THE SAME

(75) Inventors: Jae Yang Kong, Seoul (KR); Woo-Kyu Park, Cheongju (KR); Heeyeong Cho, Daejeon (KR); Daeyoung Jeong, Daejeon (KR); Gildon Choi, Daejeon (KR); Hun Yeong Koh, Seoul (KR); Sang Hee Kim, Seoul (KR); Ae Nim Pae, Seoul (KR); Yong Seo Cho, Seoul (KR); Joo Hwan Cha, Seoul (KR); Hyunah Choo, Seoul (KR); Sang Eun Chae, Daejeon (KR); Hee-Yoon Lee, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/454,817

(22) Filed: Apr. 24, 2012

(65) Prior Publication Data

US 2012/0209001 A1   Aug. 16, 2012

Related U.S. Application Data

(63) Continuation of application No. 12/530,312, filed as application No. PCT/KR2007/003415 on Jul. 13, 2007.

(30) Foreign Application Priority Data

Mar. 8, 2007 (KR) ........................ 10-2007-0022845

(51) Int. Cl.
*A61K 31/496* (2006.01)
*C07D 231/12* (2006.01)
*C07D 401/04* (2006.01)
*C07D 409/04* (2006.01)

(52) U.S. Cl. ......... 514/253.09; 514/254.05; 514/254.07; 544/364; 544/371

(58) Field of Classification Search ............... None
See application file for complete search history.

(56) References Cited

U.S. PATENT DOCUMENTS

| | | | |
|---|---|---|---|
| 3,926,999 A | 12/1975 | Poetsch | |
| 5,236,957 A * | 8/1993 | Dostert et al. | 514/620 |
| 5,922,752 A | 7/1999 | Harrison et al. | |
| 6,465,456 B2 | 10/2002 | Springer et al. | |
| 2002/0040142 A1 | 4/2002 | Springer et al. | |

FOREIGN PATENT DOCUMENTS

| | | |
|---|---|---|
| EP | 0885883 | 12/1998 |
| WO | 2004094380 | 11/2004 |
| WO | 2007019867 | 2/2007 |

OTHER PUBLICATIONS

Wong, A.H.C. et al., Potential therapeutic targets for schizophrenia, Emerging Therapeutic targets, 1999, 3, pp. 571-586.
Chtterjee, A. et al., Prevalence and Clinical Correlates of Extrapyramidal Signs and Spontaneous Dyskinesia in Never-Medicated Schizophrenic Patients, Am. J. Psychiat. Dec. 1995, 152, pp. 1724-1729.
Van Tol, H. H. M et al., Cloning of the gene for a human dopamine D4 receptor with high affinity for the antipsychotic clozapine, Nature, Apr. 1991, 350, pp. 610-614.
Oak, J. N. et al., The Dopamine D4 receptor: one decade of research, European journal of Parmacology, 2000, 405, pp. 303-327.
Lober, S. et al., Synthesis and biological investigations of dopaminergic partial agonists preferentially recognizing the D4 receptor subtype, Bioorganic & Medicinal Chemistry Letters, 2006, 16, pp. 2955-2959.
Bartolome, J. M. et al., Novel 2-N, N-dimethylaminomethyl-2, 3, 3a, 12b-tetrahydrodibenzo[b,f]furo[2,3-d]oxepin derivatives displaying combined norepinephrine reuptake inhibition and 5-HT2A/2C receptor antagonism, Bioorganic & Medicinal Chemistry Letters, 2005, 15, pp. 2898-2901.
Arora, J. et al., N-[(3S)-1-Benzylpyrrolidin-3-yl]-(2-thienyl)benzamides: Human dopamine D4 ligands with high affinity for the 5-HT2A receptor, Bioorganic & Medicinal Chemistry Lettes, 2005, 15, pp. 5253-5256.
Nakane, M. et al., 2-[4-(3,4-Dimethylphenyl)piperazin-1-ylmethyl]-1H benzoimidazole(A-381393), a selective dopamine D4 receptor antagonist, Neuropharmacology, 2005, 49, pp. 112-121.
Todd, R.D. & O'Malley, K.L., The dopamine receptor DRD4gene: are duplications distracting?, TRENDS in Parmacological Sciences, Feb. 2001, 22, pp. 55-56.
Roth, B. L. et al., Serotonin receptors represent highly favorable molecular targets for cognitive enhancement in schizophrenia and other disorders, Psychopharmacology, 2004, 174, pp. 17-24.
International Search Report mailed Aug. 29, 2008 for PCT/KR2007/003415.

* cited by examiner

*Primary Examiner* — Emily Bernhardt
(74) *Attorney, Agent, or Firm* — Lowe Hauptman Ham & Berner, LLP

(57) ABSTRACT

The present invention relates to a novel piperazinyl-propyl-pyrazole derivative, a method of its preparation and a pharmaceutically acceptable composition comprising the same. The novel piperazinyl-propyl-pyrazole derivative of the present invention has superior selective affinity for dopamine $D_4$ receptor, can effectively inhibit psychotic behavior (cage climbing) induced by apomorphine, and has relatively low adverse effects in mouse rotarod test. Therefore, it can be developed as a therapeutic agent for the treatment and prevention of central nervous system (CNS) disorders, in particular, schizophrenia, attention deficit hyperactivity disorder, depression, stress diseases, panic disorder, phobia, obsessive-compulsive disorder, posttraumatic stress disorder, cognitive disorder, Alzheimer's disease, Parkinson's disease, anxiety, paraphrenia, mania, seizure disorder, personality disorder, migraine, drug addiction, alcohol addiction, obesity, eating disorder, and sleeping disorder.

10 Claims, No Drawings

PIPERAZINYL-PROPYL-PYRAZOLE DERIVATIVES AS DOPAMINE D4 RECEPTOR ANTAGONISTS, AND PHARMACEUTICAL COMPOSITIONS CONTAINING THE SAME

CROSS-REFERENCE TO RELATED APPLICATIONS

The present application is a Continuation Application of U.S. patent application Ser. No. 12/530,312, filed Sep. 8, 2009, which is a National Stage Entry of PCT/KR2007/003415 filed Jul. 13, 2007, and claims priority to Korean patent application number 10-2007-0022845, filed on Mar. 8, 2007, which is incorporated by reference in its entirety.

TECHNICAL FIELD

The present invention relates to a piperazinyl-propyl-pyrazole derivative, a method of its preparation and a pharmaceutically acceptable salt comprising the same.

BACKGROUND ART

Dopamine is a neurotransmitter essential for neuronal signal transduction in animal brains including humans. Dopamine receptor antagonists inhibiting the binding between dopamine and its cognate receptors have been used as a therapeutic agent for treating central nervous system (CNS) disorders such as schizophrenia. Since the discovery of psychotropic effect chloropromazine in 1952, numerous psychotropic drugs with various chemical structures have been developed. Drugs such as chloropromazine and haloperidol, which typically work on dopamine $D_2$ receptors, are shown to have generally good therapeutic profiles for the treatment of schizophrenia. However, their clinical applications are greatly restricted because they are known to cause extrapyramidal side effects (EPS) in addition to other adverse effects such as sexual dysfunction, orthostatic hypotension, excessive sedation and gain in body weight, thus preventing patients from managing a normal life. Further, these drugs are shown to improve the symptoms of schizophrenia such as delusion or hallucination but were unable to improve apathy, atrophy and impairment of cognitive function at all [Wong, A. H. C. et al., *Expert. Opin. Ther. Targets* 1999, 3, 571-586; Chatterjee, A. et al., *Am. J. Psychiat.* 1995, 152, 1724-1729]. Therefore, there has been a longfelt need for the development of a new version of drug that can remedy the above-mentioned drawbacks of the typical therapeutic drugs for the treatment of mental disorders. As a result, atypical psychotropic drugs such as clozapine, olanzapine, risperidone, quetiapine and aripiprazole have been developed recently to meet the above requirement. Among them, the most representative $D_4$ antagonist is clozapine. Clozapine has shown a relatively low affinity for dopamine $D_2$ receptor but a relatively high selectivity for dopamine $D_4$ receptor. It also manifested a high affinity for serotonin (5-HT) receptor such as 5-HT$_6$ in several reports (Van Tol, H. H. M et al., *Nature* 1991, 350, 610-614; Oak, J. N. et al., *Eur. J. Pharmacol.* 2000, 405, 303-327). Clozapine is known to have relatively reduced side effects compared with those of typical drugs acting on dopamine $D_2$ receptors. However, it still has extrapyramidal side effects (EPS) and shows no efficacy in about 30-50% of patients. Based on these findings, intensive researches have been recently performed to develop the dopamine $D_4$ receptor antagonists with an improved selectivity for the $D_4$ receptor or the antagonists showing a moderate affinity for serotonin 5-HT$_2$ receptor in addition (Lober, S. et al., *Bioorg. Med. Chem. Lett.* 2006, 16, 2955-9; Bartolome, J. M. et al., *Bioorg. Med. Chem. Lett.* 2005, 15, 2898-901; Arora, J. et al., *Bioorg. Med. Chem. Lett.* 2005, 15, 5253-5256; Nakane, M. et al., *Neuropharmacology* 2005, 49, 112-121). Meanwhile, dopamine receptors have been reported to be closely associated with schizophrenia, Parkinson's disease, attention deficit hyperactivity disorder (ADHD), depression, dementia, migraine, aggressive and suicidal behaviors (Todd, R. D. & O'Malley, K. L., *TIPS* 2001, 55-56; Roth, B. L. et al., *Psychopharmacology* 2004, 174, 17-24).

The inventors of the present invention synthesized novel piperazinyl-propyl-pyrazole compounds having high affinity for the dopamine $D_4$ receptor and completed the present invention by confirming that these compounds indeed have high affinity for the dopamine receptor.

Therefore, in an embodiment, the present invention provides novel piperazinyl-propyl-pyrazole derivatives with a novel structure introduced with various substituents, and its pharmaceutically acceptable salt.

In another embodiment, the present invention provides a novel piperazinyl-propyl-pyrazole derivative and a method of its preparation.

In a further embodiment, the present invention provides a pharmaceutical composition comprising a novel piperazinyl-propyl-pyrazole derivative as an active ingredient effective in the prevention and treatment of CNS disorders.

DISCLOSURE OF INVENTION

The present invention relates to piperazinyl-propyl-pyrazole derivatives represented by the following formula 1 having selective antagonistic activity on dopamine $D_4$ receptor and its pharmaceutically acceptable salts thereof:

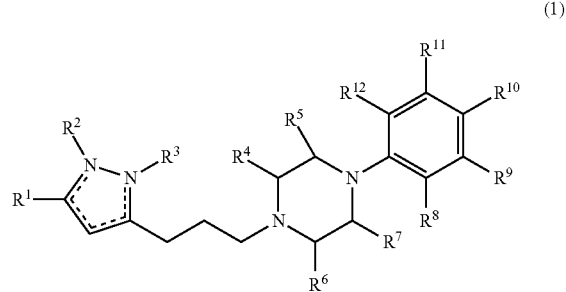

(1)

wherein $R^1$ is a $C_1$-$C_{10}$ alkyl group, or a substituted or unsubstituted aryl or heteroaryl group; one of $R^2$ and $R^3$ is a hydrogen atom, while the other is a $C_1$-$C_{10}$ alkyl group, benzyl group, or substituted or unsubstituted aryl or heteroaryl group; $R^4$, $R^5$, $R^6$ and $R^7$, being same or different with one another, are independently a hydrogen atom or a $C_1$-$C_{10}$ alkyl group; $R^8$, $R^9$, $R^{10}$, $R^{11}$ and $R^{12}$, being same or different with one another, are independently a hydrogen atom, a halogen atom, a $C_1$-$C_{10}$ alkyl group, a $C_1$-$C_{10}$ alkoxy group, a bis (substituted or unsubstituted aryl)alkylene group, a benzyl group, a nitro group, a hydroxyl group, a cyano group, an amino group, a mono or dialkylamino group, an alkylcarbonylamino group, an aminosulfonyl group, a mono or dialkylaminosulfonyl group, an alkylcarbonyl group, or an alkyloxycarbonyl group; the dotted line represents a single or double bond which depends on the substitution of $R^2$ and $R^3$ but maintains the aromaticity of a pyrazole ring; the aryl group represents a phenyl group, said heteroaryl group represents a thiophenyl group or a pyridyl group, and said substituted aryl or heteroaryl group represents an aryl or a heteroaryl group with from 1 to 3 substituents selected from the group consisting of a halogen atom, a nitro group, a $C_1$-$C_{10}$ alkyl group, a $C_1$-$C_{10}$ alkoxy group, a $C_1$-$C_{10}$ haloalkyl group, and a $C_1$-$C_{10}$ haloalkoxy.

The substituents of the compounds of the present invention are further defined as set forth hereunder.

As used herein, "alkyl" refers to a $C_1$-$C_{10}$ straight, branched or cyclic aliphatic saturated or unsaturated hydrocarbon group, preferably $C_1$-$C_6$ straight, branched or cyclic aliphatic saturated or unsaturated hydrocarbon group. More specifically, it may refer to methyl, ethyl, n-propyl, isopropyl, n-butyl, isobutyl, tert-butyl, n-pentyl, neo-pentyl, cyclopentyl, cyclobutylmethyl, n-hexyl, isohexyl, cyclohexyl, benzyl, phenylethyl and the like.

As used herein, "alkoxy" refers to a hydroxyl group wherein a hydrogen atom is substituted by the above-defined "alkyl". More specifically, it may refer to, methoxy, ethoxy, n-propoxy, i-propoxy, n-butoxy, i-butoxy, tert-butoxy, benzyloxy, phenylethoxy and the like.

As used herein, "aryl" practically refers to all the aromatic rings. Aryl herein refers to a single aromatic ring comprising at least 5 five carbon atoms, preferably 5-20 carbon atoms, or an aromatic ring including 1-5 heteroatoms selected from a nitrogen, an oxygen or a sulfur atom, preferably 1-3 heteroatoms additionally. It also refers to the structure with a few adjoining rings that is resonance-stabilized. More specific examples are phenyl, naphthyl, pyridyl, pirazine, pyrimidine, pyridazine, triazine, imidazole, triazole, quinoline, isoquinoline, quinazoline, quinoxaline, phthalazine, oxazole, isooxazole, thiazole, isothiazole, thiadiazole, oxadiazole, pyrrole, furan, thiophene and the like.

Further, aryl may have at least one substituent selected from the group consisting of alkyl, halogen, alkoxy, phenoxy, nitro, hydroxy, cyano, amino, mono or dialkylamino, alkylcarbonylamino, aminosulfonyl, mono or dialkylaminosulfonyl, alkylcarbonyl, alkyloxycarbonyl.

Piperazinyl-propyl-pyrazole derivatives are represented by the above formula 1 of the present invention, wherein, preferably, $R^1$ is a $C_1$-$C_{10}$ alkyl group, a substituted or unsubstituted phenyl group, or a substituted or unsubstituted thiophenyl group; one of $R^2$ and $R^3$ is a hydrogen atom, while the other is a $C_1$-$C_{10}$ alkyl group, benzyl group, a substituted or unsubstituted phenyl group, or a substituted or unsubstituted pyridyl group; $R^4$, $R^5$, $R^6$ and $R^7$, being same or different with one another, are independently a hydrogen atom or a $C_1$-$C_{10}$ alkyl group; $R^8$, $R^9$, $R^{10}$, $R^{11}$ and $R^{12}$, being same or different with one another, are independently a hydrogen atom, a halogen atom, a $C_1$-$C_{10}$ alkyl group, a $C_1$-$C_{10}$ alkoxy group, bis (substituted or unsubstituted phenyl)alkylene group, or a benzyl group; the dotted line represents a single bond or a double bond which depends on the substitution of $R^2$ and $R^3$ but maintains the aromaticity of a pyrazole ring; the substituted phenyl group, thiophenyl group or pyridyl group are independently a phenyl group, a thiophenyl group or a pyridyl group with from 1 to 3 substituents selected from the group consisting of a halogen atom, a nitro group, a $C_1$-$C_{10}$ alkyl group, a $C_1$-$C_{10}$ alkoxy group, a $C_1$-$C_{10}$ haloalkyl group, and a $C_1$-$C_{10}$ haloalkoxy group.

In the piperazinyl-propyl-pyrazole derivatives represented by the above formula 1 of the present invention, preferably, $R^1$ is a phenyl, 4-methylphenyl, 4-chlorophenyl, 4-fluorophenyl, 4-methoxyphenyl, 2-thiophenyl, methyl, ethyl, propyl, isopropyl, butyl, or isobutyl; one of $R^2$ and $R^3$ is a hydrogen atom, while the other is t-butyl, benzyl, phenyl, 3-nitrophenyl, 4-nitrophenyl, 3-chlorophenyl, 4-fluorophenyl, 4-methylphenyl, 4-methoxyphenyl, 4-trifluoromethylphenyl, 4-trifluoromethoxyphenyl, or 2-pyridyl; $R^4$, $R^5$, $R^6$ and $R^7$, being same or different with one another, are independently a hydrogen atom or a methyl group; $R^8$, $R^9$, $R^{10}$, $R^{11}$ and $R^{12}$, being same or different with one another, are independently a hydrogen atom, a chloro, fluoro, methyl, methoxy, or bis(4-fluorophenyl)methylene.

In particular, piperazinyl-propyl-pyrazole derivatives represented by the above formula 1 are preferably as follows:

1-(3-(1-tert-butyl-5-phenyl-1H-pyrazol-3-yl)propyl)-4-phenylpiperazine (Compound 1)

1-(3-(1-tert-butyl-5-phenyl-1H-pyrazol-3-yl)propyl)-4-(2-fluorophenyl)piperazine (Compound 2);

1-(3-(1-tert-butyl-5-phenyl-1H-pyrazol-3-yl)propyl)-4-(4-chlorophenyl)piperazine (Compound 3);

1-(3-(1-tert-butyl-5-phenyl-1H-pyrazol-3-yl)propyl)-4-(2,4-dimethylphenyl)piperazine (Compound 4);

1-(3-(1-tert-butyl-5-phenyl-1H-pyrazol-3-yl)propyl)-4-(3,4-dimethylphenyl)piperazine (Compound 5);

1-(3-(1-tert-butyl-5-phenyl-1H-pyrazol-3-yl)propyl)-4-(2,3-dimethylphenyl)piperazine (Compound 6);

1-(3-(1-tert-butyl-5-phenyl-1H-pyrazol-3-yl)propyl)-4-(4-methoxyphenyl)piperazine (Compound 7);

4-(3-(1-tert-butyl-5-phenyl-1H-pyrazol-3-yl)propyl)-2-methyl-1-m-tolylpiperazine (Compound 8);

1-(3-(1-tert-butyl-5-phenyl-1H-pyrazol-3-yl)propyl)-4-(3,4-dichlorophenyl)piperazine (Compound 9);

1-(3-(1-tert-butyl-3-phenyl-1H-pyrazol-5-yl)propyl)-4-(bis(4-fluorophenyl)methyl)piperazine (Compound 10);

1-phenyl-4-(3-(1,5-diphenyl-1H-pyrazol-3-yl)propyl)piperazine (Compound 11);

1-(2-fluorophenyl)-4-(3-(1,5-diphenyl-1H-pyrazol-3-yl)propyl)piperazine (Compound 12);

1-(4-chlorophenyl)-4-(3-(1,5-diphenyl-1H-pyrazol-3-yl)propyl)piperazine (Compound 13);

1-(2,4-dimethylphenyl)-4-(3-(1,5-diphenyl-1H-pyrazol-3-yl)propyl)piperazine (Compound 14);

1-(3,4-dimethylphenyl)-4-(3-(1,5-diphenyl-1H-pyrazol-3-yl)propyl)piperazine (Compound 15);

1-(2,3-dimethylphenyl)-4-(3-(1,5-diphenyl-1H-pyrazol-3-yl)propyl)piperazine (Compound 16);

1-(4-methoxyphenyl)-4-(3-(1,5-diphenyl-1H-pyrazol-3-yl)propyl)piperazine (Compound 17);

2-methyl-4-(3-(1,5-diphenyl-1H-pyrazol-3-yl)propyl)-1-m-tolylpiperazine (Compound 18);

1-(3,4-dichlorophenyl)-4-(3-(1,5-diphenyl-1H-pyrazol-3-yl)propyl)piperazine (Compound 19);

1-(bis(4-fluorophenyl)methyl)-4-(3-(1,5-diphenyl-1H-pyrazol-3-yl)propyl)piperazine (Compound 20);

1-(3-(1-tert-butyl-5-p-tolyl-1H-pyrazol-3-yl)propyl)-4-phenylpiperazine (Compound 21);

1-(3-(1-tert-butyl-5-p-tolyl-1H-pyrazol-3-yl)propyl)-4-(2-fluorophenyl)piperazine (Compound 22);

1-(3-(1-tert-butyl-5-p-tolyl-1H-pyrazol-3-yl)propyl)-4-(4-chlorophenyl)piperazine (Compound 23);

1-(3-(1-tert-butyl-5-p-tolyl-1H-pyrazol-3-yl)propyl)-4-(2,4-dimethylphenyl)piperazine (Compound 24);

1-(3-(1-tert-butyl-5-p-tolyl-1H-pyrazol-3-yl)propyl)-4-(3,4-dimethylphenyl)piperazine (Compound 25);

1-(3-(1-tert-butyl-5-p-tolyl-1H-pyrazol-3-yl)propyl)-4-(2,3-dimethylphenyl)piperazine (Compound 26);

1-(3-(1-tert-butyl-5-p-tolyl-1H-pyrazol-3-yl)propyl)-4-(4-methoxyphenyl)piperazine (Compound 27);

4-(3-(1-tert-butyl-5-p-tolyl-1H-pyrazol-3-yl)propyl)-2-methyl-1-m-tolylpiperazine (Compound 28);

1-(3-(1-tert-butyl-5-p-tolyl-1H-pyrazol-3-yl)propyl)-4-(3,4-dichlorophenyl)piperazine (Compound 29);

1-(3-(1-tert-butyl-5-p-tolyl-1H-pyrazol-3-yl)propyl)-4-(bis(4-fluorophenyl)methyl)piperazine (Compound 30);

1-phenyl-4-(3-(1-phenyl-5-p-tolyl-1H-pyrazol-3-yl)propyl)piperazine (Compound 31);

1-(2-fluorophenyl)-4-(3-(1-phenyl-5-p-tolyl-1H-pyrazol-3-yl)propyl)piperazine (Compound 32);

1-(4-chlorophenyl)-4-(3-(1-phenyl-5-p-tolyl-1H-pyrazol-3-yl)propyl)piperazine (Compound 33);

1-(2,4-dimethylphenyl)-4-(3-(1-phenyl-5-p-tolyl-1H-pyrazol-3-yl)propyl)piperazine (Compound 34);

1-(3,4-dimethylphenyl)-4-(3-(1-phenyl-5-p-tolyl-1H-pyrazol-3-yl)propyl)piperazine (Compound 35);

1-(2,3-dimethylphenyl)-4-(3-(1-phenyl-5-p-tolyl-1H-pyrazol-3-yl)propyl)piperazine (Compound 36);

1-(4-methoxyphenyl)-4-(3-(1-phenyl-5-p-tolyl-1H-pyrazol-3-yl)propyl)piperazine (Compound 37);

2-methyl-4-(3-(1-phenyl-5-p-tolyl-1H-pyrazol-3-yl)propyl)-1-m-tolylpiperazine (Compound 38);

1-(3,4-dichlorophenyl)-4-(3-(1-phenyl-5-p-tolyl-1H-pyrazol-3-yl)propyl)piperazine (Compound 39);

1-(bis(4-fluorophenyl)methyl)-4-(3-(1-phenyl-5-p-tolyl-1H-pyrazol-3-yl)propyl)piperazine (Compound 40);

1-(3-(1-tert-butyl-5-(4-methoxyphenyl)-1H-pyrazol-3-yl)propyl)-4-phenylpiperazine (Compound 41);

1-(3-(1-tert-butyl-5-(4-methoxyphenyl)-1H-pyrazol-3-yl)propyl)-4-(2-fluorophenyl)piperazine (Compound 42);

1-(3-(1-tert-butyl-5-(4-methoxyphenyl)-1H-pyrazol-3-yl)propyl)-4-(4-chlorophenyl)piperazine (Compound 43);

1-(3-(1-tert-butyl-5-(4-methoxyphenyl)-1H-pyrazol-3-yl)propyl)-4-(2,4-dimethylphenyl)piperazine (Compound 44);

1-(3-(1-tert-butyl-5-(4-methoxyphenyl)-1H-pyrazol-3-yl)propyl)-4-(3,4-dimethylphenyl)piperazine (Compound 45);

1-(3-(1-tert-butyl-5-(4-methoxyphenyl)-1H-pyrazol-3-yl)propyl)-4-(2,3-dimethylphenyl)piperazine (Compound 46);

1-(3-(1-tert-butyl-5-(4-methoxyphenyl)-1H-pyrazol-3-yl)propyl)-4-(4-methoxyphenyl)piperazine (Compound 47);

4-(3-(1-tert-butyl-5-(4-methoxyphenyl)-1H-pyrazol-3-yl)propyl)-2-methyl-1-m-tolylpiperazine (Compound 48);

1-(3-(1-tert-butyl-5-(4-methoxyphenyl)-1H-pyrazol-3-yl)propyl)-4-(3,4-dichlorophenyl)piperazine (Compound 49);

1-(3-(1-tert-butyl-5-(4-methoxyphenyl)-1H-pyrazol-3-yl)propyl)-4-(bis(4-fluorophenyl)methyl)piperazine (Compound 50);

1-(3-(5-(4-methoxyphenyl)-1-phenyl-1H-pyrazol-3-yl)propyl)-4-phenylpiperazine (Compound 51);

1-(2-fluorophenyl)-4-(3-(5-(4-methoxyphenyl)-1-phenyl-1H-pyrazol-3-yl)propyl)piperazine (Compound 52);

1-(4-chlorophenyl)-4-(3-(5-(4-methoxyphenyl)-1-phenyl-1H-pyrazol-3-yl)propyl)piperazine (Compound 53);

1-(3-(5-(4-methoxyphenyl)-1-phenyl-1H-pyrazol-3-yl)propyl)-4-(2,4-dimethylphenyl)piperazine (Compound 54);

1-(3-(5-(4-methoxyphenyl)-1-phenyl-1H-pyrazol-3-yl)propyl)-4-(3,4-dimethylphenyl)piperazine (Compound 55);

1-(3-(5-(4-methoxyphenyl)-1-phenyl-1H-pyrazol-3-yl)propyl)-4-(2,3-dimethylphenyl)piperazine (Compound 56);

1-(4-methoxyphenyl)-4-(3-(5-(4-methoxyphenyl)-1-phenyl-1H-pyrazol-3-yl)propyl)piperazine (Compound 57);

4-(3-(5-(4-methoxyphenyl)-1-phenyl-1H-pyrazol-3-yl)propyl)-2-methyl-1-m-tolylpiperazine (Compound 58);

1-(3,4-dichlorophenyl)-4-(3-(5-(4-methoxyphenyl)-1-phenyl-1H-pyrazol-3-yl)propyl)piperazine (Compound 59);

1-(bis(4-fluorophenyl)methyl)-4-(3-(5-(4-methoxyphenyl)-1-phenyl-1H-pyrazol-3-yl)propyl)piperazine (Compound 60);

1-(3-(1-tert-butyl-5-(4-chlorophenyl)-1H-pyrazol-3-yl)propyl)-4-phenylpiperazine (Compound 61);

1-(3-(1-tert-butyl-5-(4-chlorophenyl)-1H-pyrazol-3-yl)propyl)-4-(2-fluorophenyl)piperazine (Compound 62);

1-(3-(1-tert-butyl-5-(4-chlorophenyl)-1H-pyrazol-3-yl)propyl)-4-(4-chlorophenyl)piperazine (Compound 63);

1-(3-(1-tert-butyl-5-(4-chlorophenyl)-1H-pyrazol-3-yl)propyl)-4-(2,4-dimethylphenyl)piperazine (Compound 64);

1-(3-(1-tert-butyl-5-(4-chlorophenyl)-1H-pyrazol-3-yl)propyl)-4-(3,4-dimethylphenyl)piperazine (Compound 65);

1-(3-(1-tert-butyl-5-(4-chlorophenyl)-1H-pyrazol-3-yl)propyl)-4-(2,3-dimethylphenyl)piperazine (Compound 66);

1-(3-(1-tert-butyl-5-(4-chlorophenyl)-1H-pyrazol-3-yl)propyl)-4-(4-methoxyphenyl)piperazine (Compound 67);

4-(3-(1-tert-butyl-5-(4-chlorophenyl)-1H-pyrazol-3-yl)propyl)-2-methyl-1-m-tolylpiperazine (Compound 68);

1-(3-(1-tert-butyl-5-(4-chlorophenyl)-1H-pyrazol-3-yl)propyl)-4-(3,4-dichlorophenyl)piperazine (Compound 69);

1-(3-(1-tert-butyl-5-(4-chlorophenyl)-1H-pyrazol-3-yl)propyl)-4-(bis(4-fluorophenyl)methyl)piperazine (Compound 70);

1-(3-(5-(4-chlorophenyl)-1-phenyl-1H-pyrazol-3-yl)propyl)-4-phenylpiperazine (Compound 71);

1-(3-(5-(4-chlorophenyl)-1-phenyl-1H-pyrazol-3-yl)propyl)-4-(2-fluorophenyl)piperazine (Compound 72);

1-(4-chlorophenyl)-4-(3-(5-(4-chlorophenyl)-1-phenyl-1H-pyrazol-3-yl)propyl)piperazine (Compound 73);

1-(3-(5-(4-chlorophenyl)-1-phenyl-1H-pyrazol-3-yl)propyl)-4-(2,4-dimethylphenyl)piperazine (Compound 74);

1-(3-(5-(4-chlorophenyl)-1-phenyl-1H-pyrazol-3-yl)propyl)-4-(3,4-dimethylphenyl)piperazine (Compound 75);

1-(3-(5-(4-chlorophenyl)-1-phenyl-1H-pyrazol-3-yl)propyl)-4-(2,3-dimethylphenyl)piperazine (Compound 76);

1-(3-(5-(4-chlorophenyl)-1-phenyl-1H-pyrazol-3-yl)propyl)-4-(4-methoxyphenyl)piperazine (Compound 77);

4-(3-(5-(4-chlorophenyl)-1-phenyl-1H-pyrazol-3-yl)propyl)-2-methyl-1-m-tolylpiperazine (Compound 78);

1-(3,4-dichlorophenyl)-4-(3-(5-(4-chlorophenyl)-1-phenyl-1H-pyrazol-3-yl)propyl)piperazine (Compound 79);

1-(bis(4-fluorophenyl)methyl)-4-(3-(5-(4-chlorophenyl)-1-phenyl-1H-pyrazol-3-yl)propyl)piperazine (Compound 80);

1-(3-(1-tert-butyl-5-(4-fluorophenyl)-1H-pyrazol-3-yl)propyl)-4-phenylpiperazine (Compound 81);

1-(3-(1-tert-butyl-5-(4-fluorophenyl)-1H-pyrazol-3-yl)propyl)-4-(2-fluorophenyl)piperazine (Compound 82);

1-(3-(1-tert-butyl-5-(4-fluorophenyl)-1H-pyrazol-3-yl)propyl)-4-(4-chlorophenyl)piperazine (Compound 83);

1-(3-(1-tert-butyl-5-(4-fluorophenyl)-1H-pyrazol-3-yl)propyl)-4-(2,4-dimethylphenyl)piperazine (Compound 84);

1-(3-(1-tert-butyl-5-(4-fluorophenyl)-1H-pyrazol-3-yl)propyl)-4-(3,4-dimethylphenyl)piperazine (Compound 85);

1-(3-(1-tert-butyl-5-(4-fluorophenyl)-1H-pyrazol-3-yl)propyl)-4-(2,3-dimethylphenyl)piperazine (Compound 86);

1-(3-(1-tert-butyl-5-(4-fluorophenyl)-1H-pyrazol-3-yl)propyl)-4-(4-methoxyphenyl)piperazine (Compound 87);

4-(3-(1-tert-butyl-5-(4-fluorophenyl)-1H-pyrazol-3-yl)propyl)-2-methyl-1-m-tolylpiperazine (Compound 88);

1-(3-(1-tert-butyl-5-(4-fluorophenyl)-1H-pyrazol-3-yl)propyl)-4-(3,4-dichlorophenyl)piperazine (Compound 89);

1-(3-(1-tert-butyl-5-(4-fluorophenyl)-1H-pyrazol-3-yl)propyl)-4-(bis(4-fluorophenyl)methyl)piperazine (Compound 90);

1-(3-(5-(4-fluorophenyl)-1-phenyl-1H-pyrazol-3-yl)propyl)-4-phenylpiperazine (Compound 91);
1-(2-fluorophenyl)-4-(3-(5-(4-fluorophenyl)-1-phenyl-1H-pyrazol-3-yl)propyl)piperazine (Compound 92);
1-(4-chlorophenyl)-4-(3-(5-(4-fluorophenyl)-1-phenyl-1H-pyrazol-3-yl)propyl)piperazine (Compound 93);
1-(3-(5-(4-fluorophenyl)-1-phenyl-1H-pyrazol-3-yl)propyl)-4-(2,4-dimethylphenyl)piperazine (Compound 94);
1-(3-(5-(4-fluorophenyl)-1-phenyl-1H-pyrazol-3-yl)propyl)-4-(3,4-dimethylphenyl)piperazine (Compound 95);
1-(3-(5-(4-fluorophenyl)-1-phenyl-1H-pyrazol-3-yl)propyl)-4-(2,3-dimethylphenyl)piperazine (Compound 96);
1-(3-(5-(4-fluorophenyl)-1-phenyl-1H-pyrazol-3-yl)propyl)-4-(4-methoxyphenyl)piperazine (Compound 97);
4-(3-(5-(4-fluorophenyl)-1-phenyl-1H-pyrazol-3-yl)propyl)-2-methyl-1-m-tolylpiperazine (Compound 98);
1-(3,4-dichlorophenyl)-4-(3-(5-(4-fluorophenyl)-1-phenyl-1H-pyrazol-3-yl)propyl)piperazine (Compound 99);
1-(bis(4-fluorophenyl)methyl)-4-(3-(5-(4-fluorophenyl)-1-phenyl-1H-pyrazol-3-yl)propyl)piperazine (Compound 100);
1-(3-(1-tert-butyl-5-(thiophene-2-yl)-1H-pyrazol-3-yl)propyl)-4-phenylpiperazine (Compound 101);
1-(3-(1-tert-butyl-5-(thiophene-2-yl)-1H-pyrazol-3-yl)propyl)-4-(2-fluorophenyl)piperazine (Compound 102);
1-(3-(1-tert-butyl-5-(thiophene-2-yl)-1H-pyrazol-3-yl)propyl)-4-(4-chlorophenyl)piperazine (Compound 103);
1-(3-(1-tert-butyl-5-(thiophene-2-yl)-1H-pyrazol-3-yl)propyl)-4-(2,4-dimethylphenyl)piperazine (Compound 104);
1-(3-(1-tert-butyl-5-(thiophene-2-yl)-1H-pyrazol-3-yl)propyl)-4-(3,4-dimethylphenyl)piperazine (Compound 105);
1-(3-(1-tert-butyl-5-(thiophene-2-yl)-1H-pyrazol-3-yl)propyl)-4-(2,3-dimethylphenyl)piperazine (Compound 106);
1-(3-(1-tert-butyl-5-(thiophene-2-yl)-1H-pyrazol-3-yl)propyl)-4-(4-methoxyphenyl)piperazine (Compound 107);
4-(3-(1-tert-butyl-5-(thiophene-2-yl)-1H-pyrazol-3-yl)propyl)-2-methyl-1-m-tolylpiperazine (Compound 108);
1-(3-(1-tert-butyl-5-(thiophene-2-yl)-1H-pyrazol-3-yl)propyl)-4-(3,4-dichlorophenyl)piperazine (Compound 109);
1-(3-(1-tert-butyl-5-(thiophene-2-yl)-1H-pyrazol-3-yl)propyl)-4-(bis(4-fluorophenyl)methyl)piperazine (Compound 110);
1-phenyl-4-(3-(1-phenyl-5-(thiophene-2-yl)-1H-pyrazol-3-yl)propyl)piperazine (Compound 111);
1-(2-fluorophenyl)-4-(3-(1-phenyl-5-(thiophene-2-yl)-1H-pyrazol-3-yl)propyl)piperazine (Compound 112);
1-(4-chlorophenyl)-4-(3-(1-phenyl-5-(thiophene-2-yl)-1H-pyrazol-3-yl)propyl)piperazine (Compound 113);
1-(2,4-dimethylphenyl)-4-(3-(1-phenyl-5-(thiophene-2-yl)-1H-pyrazol-3-yl)propyl)piperazine (Compound 114);
1-(3,4-dimethylphenyl)-4-(3-(1-phenyl-5-(thiophene-2-yl)-1H-pyrazol-3-yl)propyl)piperazine (Compound 115);
1-(2,3-dimethylphenyl)-4-(3-(1-phenyl-5-(thiophene-2-yl)-1H-pyrazol-3-yl)propyl)piperazine (Compound 116);
1-(4-methoxyphenyl)-4-(3-(1-phenyl-5-(thiophene-2-yl)-1H-pyrazol-3-yl)propyl)piperazine (Compound 117);
2-methyl-4-(3-(1-phenyl-5-(thiophene-2-yl)-1H-pyrazol-3-yl)propyl)-1-m-tolylpiperazine (Compound 118);
1-(3,4-dichlorophenyl)-4-(3-(1-phenyl-5-(thiophene-2-yl)-1H-pyrazol-3-yl)propyl)piperazine (Compound 119);
1-(bis(4-fluorophenyl)methyl)-4-(3-(1-phenyl-5-(thiophene-2-yl)-1H-pyrazol-3-yl)propyl)piperazine (Compound 120);
1-phenyl-4-(3-(1-phenyl-3-methyl-1H-pyrazol-5-yl)propyl)piperazine (Compound 121);
1-(2-fluorophenyl)-4-(3-(1-phenyl-3-methyl-1H-pyrazol-5-yl)propyl)piperazine (Compound 122);
1-phenyl-4-(3-(1-phenyl-3-ethyl-1H-pyrazol-5-yl)propyl)piperazine (Compound 123);
1-(2-fluorophenyl)-4-(3-(1-phenyl-3-ethyl-1H-pyrazol-5-yl)propyl)piperazine (Compound 124);
1-(3-(1-tert-butyl-5-propyl-1H-pyrazol-3-yl)propyl)-4-phenylpiperazine (Compound 125);
1-(3-(1-tert-butyl-5-propyl-1H-pyrazol-3-yl)propyl)-4-(2-fluorophenyl)piperazine (Compound 126);
1-(3-(1-tert-butyl-5-propyl-1H-pyrazol-3-yl)propyl)-4-(4-chlorophenyl)piperazine (Compound 127);
1-(3-(1-tert-butyl-5-propyl-1H-pyrazol-3-yl)propyl)-4-(2,4-dimethylphenyl)piperazine (Compound 128);
1-(3-(1-tert-butyl-5-propyl-1H-pyrazol-3-yl)propyl)-4-(3,4-dimethylphenyl)piperazine (Compound 129);
1-(3-(1-tert-butyl-5-propyl-1H-pyrazol-3-yl)propyl)-4-(2,3-dimethylphenyl)piperazine (Compound 130);
1-(3-(1-tert-butyl-5-propyl-1H-pyrazol-3-yl)propyl)-4-(4-methoxyphenyl)piperazine (Compound 131);
4-(3-(1-tert-butyl-5-propyl-1H-pyrazol-3-yl)propyl)-2-methyl-1-m-tolylpiperazine (Compound 132);
1-(3-(1-tert-butyl-5-propyl-1H-pyrazol-3-yl)propyl)-4-(3,4-dichlorophenyl)piperazine (Compound 133);
1-(3-(1-tert-butyl-5-propyl-1H-pyrazol-3-yl)propyl)-4-(bis(4-fluorophenyl)methyl)piperazine (Compound 134);
1-(3-(1-tert-butyl-3-propyl-1H-pyrazol-5-yl)propyl)-4-phenylpiperazine (Compound 135);
1-(3-(1-tert-butyl-3-propyl-1H-pyrazol-5-yl)propyl)-4-(2-fluorophenyl)piperazine (Compound 136);
1-(3-(1-tert-butyl-3-propyl-1H-pyrazol-5-yl)propyl)-4-(4-chlorophenyl)piperazine (Compound 137);
1-(3-(1-tert-butyl-3-propyl-1H-pyrazol-5-yl)propyl)-4-(2,4-dimethylphenyl)piperazine (Compound 138);
1-(3-(1-tert-butyl-3-propyl-1H-pyrazol-5-yl)propyl)-4-(3,4-dimethylphenyl)piperazine (Compound 139);
1-(3-(1-tert-butyl-3-propyl-1H-pyrazol-5-yl)propyl)-4-(2,3-dimethylphenyl)piperazine (Compound 140);
1-(3-(1-tert-butyl-3-propyl-1H-pyrazol-5-yl)propyl)-4-(4-methoxyphenyl)piperazine (Compound 141);
4-(3-(1-tert-butyl-3-propyl-1H-pyrazol-5-yl)propyl)-2-methyl-1-m-tolylpiperazine (Compound 142);
1-(3-(1-tert-butyl-3-propyl-1H-pyrazol-5-yl)propyl)-4-(3,4-dichlorophenyl)piperazine (Compound 143);
1-(3-(1-tert-butyl-3-propyl-1H-pyrazol-5-yl)propyl)-4-(bis(4-fluorophenyl)methyl)piperazine (Compound 144);
1-phenyl-4-(3-(1-phenyl-5-propyl-1H-pyrazol-3-yl)propyl)piperazine (Compound 145);
1-(2-fluorophenyl)-4-(3-(1-phenyl-5-propyl-1H-pyrazol-3-yl)propyl)piperazine (Compound 146);
1-(4-chlorophenyl)-4-(3-(1-phenyl-5-propyl-1H-pyrazol-3-yl)propyl)piperazine (Compound 147);
1-(2,4-dimethylphenyl)-4-(3-(1-phenyl-5-propyl-1H-pyrazol-3-yl)propyl)piperazine (Compound 148);
1-(3,4-dimethylphenyl)-4-(3-(1-phenyl-5-propyl-1H-pyrazol-3-yl)propyl)piperazine (Compound 149);
1-(2,3-dimethylphenyl)-4-(3-(1-phenyl-5-propyl-1H-pyrazol-3-yl)propyl)piperazine (Compound 150);
1-(4-methoxyphenyl)-4-(3-(1-phenyl-5-propyl-1H-pyrazol-3-yl)propyl)piperazine (Compound 151);
2-methyl-4-(3-(1-phenyl-5-propyl-1H-pyrazol-3-yl)propyl)-1-m-tolylpiperazine (Compound 152);
1-(3,4-dichlorophenyl)-4-(3-(1-phenyl-5-propyl-1H-pyrazol-3-yl)propyl)piperazine (Compound 153);
1-(bis(4-fluorophenyl)methyl)-4-(3-(1-phenyl-5-propyl-1H-pyrazol-3-yl)propyl)piperazine (Compound 154);
1-phenyl-4-(3-(1-phenyl-3-propyl-1H-pyrazol-5-yl)propyl)piperazine (Compound 155);

1-(2-fluorophenyl)-4-(3-(1-phenyl-3-propyl-1H-pyrazol-5-yl)propyl)piperazine (Compound 156);
1-(4-chlorophenyl)-4-(3-(1-phenyl-3-propyl-1H-pyrazol-5-yl)propyl)piperazine (Compound 157);
1-(2,4-dimethylphenyl)-4-(3-(1-phenyl-3-propyl-1H-pyrazol-5-yl)propyl)piperazine (Compound 158);
1-(3,4-dimethylphenyl)-4-(3-(1-phenyl-3-propyl-1H-pyrazol-5-yl)propyl)piperazine (Compound 159);
1-(2,3-dimethylphenyl)-4-(3-(1-phenyl-3-propyl-1H-pyrazol-5-yl)propyl)piperazine (Compound 160);
1-(4-methoxyphenyl)-4-(3-(1-phenyl-3-propyl-1H-pyrazol-5-yl)propyl)piperazine (Compound 161);
2-methyl-4-(3-(1-phenyl-3-propyl-1H-pyrazol-5-yl)propyl)-1-m-tolylpiperazine (Compound 162);
1-(3,4-dichlorophenyl)-4-(3-(1-phenyl-3-propyl-1H-pyrazol-5-yl)propyl)piperazine (Compound 163);
1-(bis(4-fluorophenyl)methyl)-4-(3-(1-phenyl-3-propyl-1H-pyrazol-5-yl)propyl)piperazine (Compound 164);
1-(2-fluorophenyl)-4-(3-(1-(3-chlorophenyl)-3-propyl-1H-pyrazol-5-yl)propyl)piperazine (Compound 165)
1-(2-fluorophenyl)-4-(3-(1-(4-methoxyphenyl)-3-propyl-1H-pyrazol-5-yl)propyl)piperazine (Compound 166)
1-(2-fluorophenyl)-4-(3-(1-(4-methylphenyl)-3-propyl-1H-pyrazol-5-yl)propyl)piperazine (Compound 167)
1-(2-fluorophenyl)-4-(3-(1-(4-fluorophenyl)-3-propyl-1H-pyrazol-5-yl)propyl)piperazine (Compound 168)
1-(2-fluorophenyl)-4-(3-(1-(4-chlorophenyl)-3-propyl-1H-pyrazol-5-yl)propyl)piperazine (Compound 169)
1-(2-fluorophenyl)-4-(3-(1-(4-trifluorphenyl)-3-propyl-1H-pyrazol-5-yl)propyl)piperazine (Compound 170)
1-(2-fluorophenyl)-4-(3-(1-(4-trifluoromethoxyphenyl)-3-propyl-1H-pyrazol-5-yl)propyl)piperazine (Compound 171)
1-(2-fluorophenyl)-4-(3-(1-(4-nitrophenyl)-3-propyl-1H-pyrazol-5-yl)propyl)piperazine (Compound 172)
1-(2-fluorophenyl)-4-(3-(1-benzyl-3-propyl-1H-pyrazol-5-yl)propyl)piperazine (Compound 173)
1-(2-fluorophenyl)-4-(3-(1-(3-nitrophenyl)-3-propyl-1H-pyrazol-5-yl)propyl)piperazine (Compound 174)
1-(2-fluorophenyl)-4-(3-(1-(2'-pyridyl)-3-propyl-1H-pyrazol-5-yl)propyl)piperazine (Compound 175)
1-phenyl-4-(3-(1-phenyl-3-isopropyl-1H-pyrazol-5-yl)propyl)piperazine (Compound 176);
1-(2-fluorophenyl)-4-(3-(1-phenyl-3-isopropyl-1H-pyrazol-5-yl)propyl)piperazine (Compound 177);
1-phenyl-4-(3-(1-phenyl-3-butyl-1H-pyrazol-5-yl)propyl)piperazine (Compound 178);
1-(2-fluorophenyl)-4-(3-(1-phenyl-3-butyl-1H-pyrazol-5-yl)propyl)piperazine (Compound 179);
1-(2-fluorophenyl)-4-(3-(1-(3-chlorophenyl)-3-butyl-1H-pyrazol-5-yl)propyl)piperazine (Compound 180)
1-(2-fluorophenyl)-4-(3-(1-(4-methoxyphenyl)-3-butyl-1H-pyrazol-5-yl)propyl)piperazine (Compound 181)
1-(2-fluorophenyl)-4-(3-(1-(4-methylphenyl)-3-butyl-1H-pyrazol-5-yl)propyl)piperazine (Compound 182)
1-(2-fluorophenyl)-4-(3-(1-(4-fluorophenyl)-3-butyl-1H-pyrazol-5-yl)propyl)piperazine (Compound 183)
1-(2-fluorophenyl)-4-(3-(1-(4-chlorophenyl)-3-butyl-1H-pyrazol-5-yl)propyl)piperazine (Compound 184)
1-(2-fluorophenyl)-4-(3-(1-(4-trifluoromethylphenyl)-3-butyl-1H-pyrazol-5-yl)propyl)piperazine (Compound 185)
1-(2-fluorophenyl)-4-(3-(1-(4-nitrophenyl)-3-butyl-1H-pyrazol-5-yl)propyl)piperazine (Compound 186)
1-(2-fluorophenyl)-4-(3-(1-benzyl-3-butyl-1H-pyrazol-5-yl)propyl)piperazine (Compound 187)
1-(2-fluorophenyl)-4-(3-(1-(3-nitrophenyl)-3-butyl-1H-pyrazol-5-yl)propyl)piperazine (Compound 188)
1-(2-fluorophenyl)-4-(3-(1-(2'-pyridyl)-3-butyl-1H-pyrazol-5-yl)propyl)piperazine (Compound 189)
1-phenyl-4-(3-(1-phenyl-3-isobutyl-1H-pyrazol-5-yl)propyl)piperazine (Compound 190);
1-(2-fluorophenyl)-4-(3-(1-phenyl-3-isobutyl-1H-pyrazol-5-yl)propyl)piperazine (Compound 191).

In an embodiment, the present invention provides a method for preparing a piperazinyl-propyl-pyrazole derivative represented by the above formula 1 by performing reductive amination between a pyrazole aldehyde derivative represented by the following formula 2 and a piperazine derivative represented by the following formula 3:

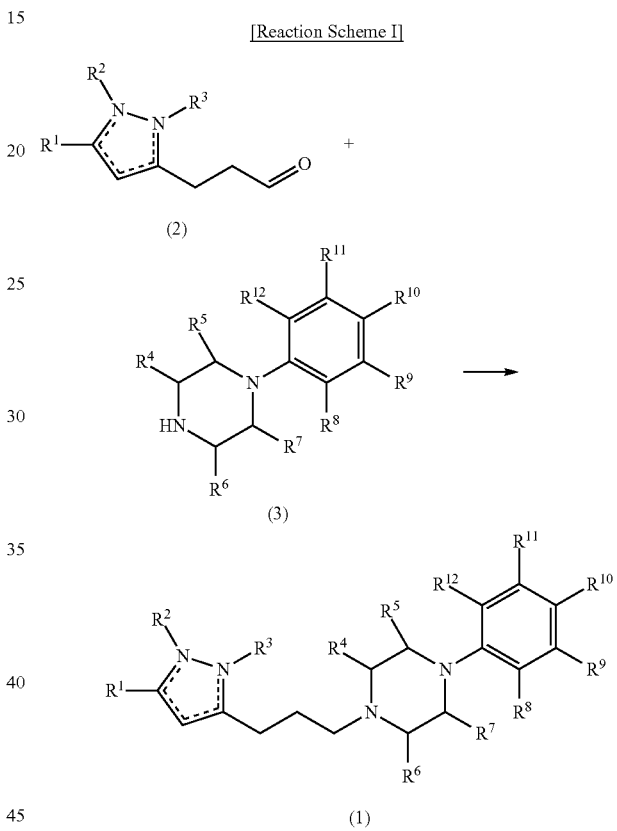

[Reaction Scheme I]

wherein, in the above reaction scheme I, $R^1$, $R^2$, $R^3$, $R^4$, $R^5$, $R^6$, $R^7$, $R^8$, $R^9$, $R^{10}$, $R^{11}$ and $R^{12}$ are same as defined above.

The reductive amination according to the above reaction scheme I is performed as follows: first, pyrazole aldehyde derivative and piperazine, both dissolved in a solvent, are stirred at room temperature along with a molecular sieve under nitrogen atmosphere, dropwisely added with a base, stirred again at room temperature for 0.5-1 hr and then reduced by adding a reducing agent to form a piperazinyl-propyl-pyrazole derivative represented by the above formula 1.

The solvent used in the reductive amination according to the above reaction scheme I is a conventional solvent, examples of which include methylene chloride, chloroform, 1,2-dichloroethane and the like. In the present invention, methylene chloride was used.

The molecular sieve used in the present invention has a size of 0.1-100 in diameter, preferably 0.1-10. In the present invention, a molecular sieve with a size of 4 in diameter was used.

The base used in the present invention includes alkylamines such as triethylamine, diisopropylethylamine and the like, or alkali metal or alkalic metal salt such as $Na_2CO_3$, $K_2CO_3$ and the like. In the present invention, diisopropylethylamine was used. The base is used 1-5 equivalents per reactant, preferably 1 equivalent.

Examples of reducing agents are $NaBH_4$, $NaBH(OAc)_3$ and the like, and $NaBH(OAc)_3$ was used in the present invention. The reducing agent is used 1-10 equivalents, preferably 3 equivalents.

Reaction is performed for about 1-24 hrs, preferably 12-15 hrs. Reaction is preferably performed at room temperature. Upon completion of reaction, the resultant is added with water to eliminate any remaining reducing agent, and then separated via a conventional method such as column chromatography to finally obtain pure piperazinyl-propyl-pyrazole derivatives.

In the above method according to reaction scheme I, the reaction intermediates of a pyrazole aldehyde derivative represented by the above formula 2 and a piperazine derivative represented by the above formula 3 are known compounds and can be easily synthesized by using a known method.

As for a pyrazole aldehyde derivative represented by the above formula 2 can be synthesized by reacting β-keto ketones with hydrazine.

The method of synthesizing the pyrazole aldehyde derivative represented by the above formula 2 is shown in the following reaction scheme II.

[Reaction Scheme II]

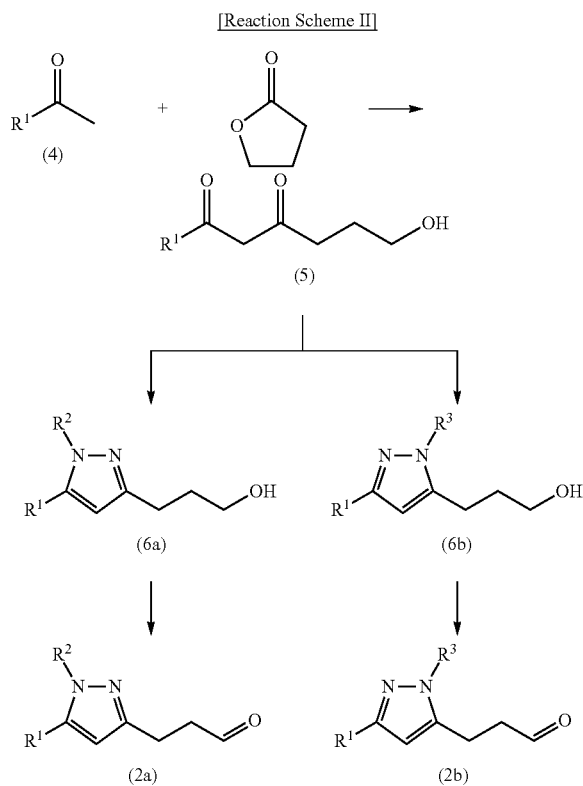

In the above reaction scheme II, $R^1$, $R^2$, and $R^3$ are independently same as defined above.

As shown in the above reaction scheme II, a ketone compound represented by the above formula 4 and γ-butyrolactone are reacted at 30~50° C. in the presence of benzene as a solvent after adding NaOMe to produce a diketone compound represented by the above formula 5. The diketone compound represented by the above formula 5 is reacted with hydrazine to produce a pyrazole alcohol derivative represented by the above formula 6a or 6b. Here, if $R^1$ is an aryl group a pyrazole alcohol derivative represented by the above formula 6a is obtained, while pyrazole alcohol derivatives represented by both the above formula 6a and 6b are obtained if $R^1$ is an alkyl group.

Each of the pyrazole alcohol derivatives represented by the above formula 6a or 6b is oxidized by using an oxidizing agent such as PCC (pyridium chlorochromate) to obtain a pyrazole aldehyde derivative represented by the above formula 2a or 2b. The detailed synthetic methods are described in the following examples.

The compound represented by the above formula 1 of the present invention has a superior selective affinity for dopamine $D_4$ receptor, can effectively inhibit the psychotic behavior (cage climbing) of mice induced by apomorphine, and exhibited relatively low adverse effects in mouse rotarod test. Therefore, it has potential to be developed as a therapeutic agent for the treatment and prevention of CNS disorders, in particular, schizophrenia, attention deficit hyperactivity disorder, depression, stress diseases, panic disorder, phobia, obsessive-compulsive disorder, posttraumatic stress disorder, cognitive disorder, Alzheimer's disease, Parkinson's disease, anxiety, paraphrenia, mania, seizure disorder, personality disorder, migraine, drug addiction, alcohol addiction, obesity, eating disorder, and sleeping disorder.

Therefore, the pharmaceutical composition of the present invention comprises a compound represented by the above formula 1 or its pharmaceutically acceptable salts thereof as active ingredients and thus includes a pharmaceutical composition effective in the treatment and prevention of CNS disorders.

The pharmaceutically acceptable salts of the present invention are those which can be manufactured by using a method known in the art, for example, salts with inorganic acids such as hydrochloric acid, bromic acid, sulfuric acid, sodium hydrogen sulfate, phosphate, nitrate, carbonate and the like; and salts with organic acids such as formic acid, acetic acid, propionic acid, oxalic acid, succinic acid, benzoic acid, citric acid, maleic acid, malonic acid, tartaric acid, gluconic acid, lactic acid, gestisic acid, fumaric acid, lactobionic acid, salicylic acid, trifluoroacetic acid and acetylsalicylic acid (aspirin); or salts with amino acids such as glycine, alanine, valine, isoleucine, serine, cysteine, cystine, aspartic acid, glutamine, lysine, arginine, tyrosine, proline and the like; salts with sulfonic acid such as methane sulfonate, ethane sulfonate, benzene sulfonate, toluene sulfonate and the like; metal salts by reaction with an alkali metal such as sodium, potassium and the like; or salts with ammonium ion and the like.

The pharmaceutical composition can be prepared in the form of, for example, tablets, capsules, troches, liquids, suspensions, etc., for oral or intraperitoneal administration, by adding the compound represented by the above formula 1 or its pharmaceutically acceptable salts with a conventional non-toxic pharmaceutically acceptable additive such as a carrier, a reinforcing agent, an excipient, and the like, for the prevention and treatment of various kinds of CNS disorders.

Examples of excipients to be used in the pharmaceutical composition of the present invention include a sweetener, a binder, a solubilizer, a solubilization builder, a wetting agent, an emulsifier, an isotonic agent, an adsorbent, a disintegrator, an antioxidant, a preservative, a lubricant, a filler, a flavoring agent, etc. For example, lactose, dextrose, sucrose, mannitol, sorbitol, cellulose, glycine, silica, talc, stearate, stearin, magnesium stearate, magnesium aluminosilicate, starch, gelatin, tragacanth Gum, alginic acid, sodium alginate, methylcellulose, sodium carboxylmethylcellulose, agar, water, ethanol, polyethylene glycol, polyvinylpyrolidone, sodium hydroxide, potassium hydroxide, orange essence, strawberry essence, vanilla flavor and the like.

The amount of dosage of the compound represented by the formula 1 of the present invention can vary depending on the patient's age, body weight, sex, type of administration, health conditions, seriousness of disease and the like. In general, the dosage is 0.01-5,000 mg/day, and it can be administered once or a few times daily at regular intervals after consulting with a physician.

BEST MODE FOR CARRYING OUT THE INVENTION

The following examples are embodiments of the methods for preparing compound represented by the above formula 1 according to the reaction scheme I, and they should not be construed as limiting the scope of the present invention.

EXAMPLE

Example 1

1-(3-(1-tert-butyl-5-phenyl-1H-pyrazol-3-yl)propyl)-4-phenylpiperazine (Compound 1)

3-(1-tert-butyl-5-phenyl-1H-pyrazol-3-yl)propanal (80 mg, 312 mmol) and 1-phenylpiperazine (0.047 mL, 0.312 mmol) were dissolved in 5 mL of $CH_2Cl_2$, and then 0.7 g of 4 molecular sieve powder was added thereto and stirred. Diisopropylethylamine (DIPEA; 54 mL, 0.312 mmol) was slowly added thereto, and stirred for 30 min at room temperature. Then, $NaBH(OAc)_3$ (231 mg, 1.092 mmol) was added thereto and stirred for 12 hours at room temperature. The reaction progress and completion were confirmed by TLC. Upon completion of the reaction, water (0.1 mL) was added to the reaction mixture and then stirred for 3 min. 81 mg (64%) of target compound was obtained via column chromatography (EtOAc:Hexane=4:1, v/v).

$^1$H NMR (400 MHz, MeOH-$d_4$) δ 7.62-7.51 (m, 5H), 7.41-7.34 (m, 2H), 7.26-7.23 (m, 2H), 7.10 (t, 1H, J=7.3 Hz), 6.67 (s, 1H), 3.90-3.48 (m, 8H), 3.43-3.38 (m, 2H), 3.06 (t, 2H, J=7.7 Hz), 2.41-2.39 (m, 2H), 1.61 (s, 9H).

Example 2

1-(3-(1-tert-butyl-5-phenyl-1H-pyrazol-3-yl)propyl)-4-(2-fluorophenyl)piperazine (Compound 2)

79 mg (55%) of target compound was obtained by using a method same as in Example 1 by using 3-(1-tert-butyl-5-phenyl-1H-pyrazol-3-yl)propanal (80 mg, 0.312 mmol), 1-(2-fluorophenyl)piperazine (56 mg, 0.312 mmol), DIPEA (82 mL, 0.468 mmol) and $NaBH(OAc)_3$ (198 mg, 0.936 mmol).

$^1$H NMR (400 MHz, MeOH-$d_4$) δ 7.59-7.41 (m, 5H), 7.20-7.03 (m, 4H), 6.50 (s, 1H), 3.84-3.69 (m, 2H), 33.69-3.54 (m, 2H), 3.43-3.13 (m, 6H), 3.11-2.88 (m, 2H), 2.38-2.22 (m, 2H), 1.56 (s, 9H).

Example 3

1-(3-(1-tert-butyl-5-phenyl-1H-pyrazol-3-yl)propyl)-4-(4-chlorophenyl)piperazine (Compound 3)

101 mg (68%) of target compound was obtained by using a method same as in Example 1 by using 3-(1-tert-butyl-5-phenyl-1H-pyrazol-3-yl)propanal (80 mg, 0.312 mmol), 1-(4-chlorophenyl)piperazine (84 mg, 0.312 mmol), DIPEA (82 mL, 0.468 mmol) and $NaBH(OAc)_3$ (198 mg, 0.936 mmol).

$^1$H NMR (400 MHz, MeOH-$d_4$) δ 7.58-7.40 (m, 5H), 7.27 (d, 2H, J=8.5 Hz), 7.01 (d, 2H, J=8.7 Hz), 6.44 (s, 1H), 3.97-3.62 (m, 4H), 3.42-3.08 (m, 6H), 2.99-2.89 (m, 2H), 2.43-2.20 (m, 2H), 1.54 (s, 9H).

Example 4

1-(3-(1-tert-butyl-5-phenyl-1H-pyrazol-3-yl)propyl)-4-(2,4-dimethylphenyl)piperazine (Compound 4)

99 mg (68%) of target compound was obtained by using a method same as in Example 1 by using 3-(1-tert-butyl-5-phenyl-1H-pyrazol-3-yl)propanal (80 mg, 0.312 mmol), 1-(2,4-dimethylphenyl)piperazine (59 mg, 0.312 mmol), DIPEA (82 mL, 0.468 mmol) and $NaBH(OAc)_3$ (198 mg, 0.936 mmol).

$^1$H NMR (400 MHz, MeOH-$d_4$) δ 7.62-7.39 (m, 5H), 7.08-6.95 (m, 3H), 6.51 (s, 1H), 3.79-3.53 (m, 2H), 3.42-3.11 (m, 8H), 3.02-2.90 (m, 2H), 2.48-2.21 (m, 2H), 2.30 (s, 3H), 2.25 (s, 3H), 1.57 (s, 9H).

Example 5

1-(3-(1-tert-butyl-5-phenyl-1H-pyrazol-3-yl)propyl)-4-(3,4-dimethylphenyl)piperazine (Compound 5)

62 mg (71%) of target compound was obtained by using a method same as in Example 1 by using 3-(1-tert-butyl-5-phenyl-1H-pyrazol-3-yl)propanal (50 mg, 0.195 mmol), 1-(3,4-dimethylphenyl)piperazine (35.4 mg, 0.186 mmol), DIPEA (49 mL, 0.279 mmol) and $NaBH(OAc)_3$ (118 mg, 0.558 mmol).

$^1$H NMR (400 MHz, MeOH-$d_4$) δ 7.60-7.38 (m, 5H), 7.08 (d, 1H, J=8.1 Hz), 6.93 (s, 1H), 6.85 (d, 1H, J=7.9 Hz), 6.39 (s, 1H), 3.73-3.40 (m, 8H), 3.40-3.23 (m, 2H), 2.93-2.78 (m, 2H), 2.38-2.13 (m, 2H), 2.26 (s, 3H), 2.20 (s, 3H), 1.53 (s, 9H).

Example 6

1-(3-(1-tert-butyl-5-phenyl-1H-pyrazol-3-yl)propyl)-4-(2,3-dimethylphenyl)piperazine (Compound 6)

39 mg (45%) of target compound was obtained by using a method same as in Example 1 by using 3-(1-tert-butyl-5-phenyl-1H-pyrazol-3-yl)propanal (50 mg, 0.195 mmol), 1-(2,3-dimethylphenyl)piperazine (35.4 mg, 0.186 mmol), DIPEA (49 mL, 0.279 mmol) and $NaBH(OAc)_3$ (118 mg, 0.558 mmol).

$^1$H NMR (400 MHz, MeOH-$d_4$) δ 7.50-7.32 (m, 5H), 7.13-6.89 (m, 3H), 6.15 (s, 1H), 3.77-3.60 (m, 2H), 3.49-3.04 (m, 8H), 2.81 (t, 2H, J=7.3 Hz), 2.31-2.12 (m, 2H), 2.28 (s, 3H), 2.27 (s, 3H), 1.47 (s, 9H).

Example 7

1-(3-(1-tert-butyl-5-phenyl-1H-pyrazol-3-yl)propyl)-4-(4-methoxyphenyl)piperazine (Compound 7)

62 mg (71%) of target compound was obtained by using a method same as in Example 1 by using 3-(1-tert-butyl-5-phenyl-1H-pyrazol-3-yl)propanal (50 mg, 0.195 mmol), 1-(4-methoxyphenyl)piperazine (49 mg, 0.186 mmol), DIPEA (49 mL, 0.279 mmol) and NaBH(OAc)$_3$ (118 mg, 0.558 mmol).

$^1$H NMR (400 MHz, DMSO-d$_6$) δ 10.77 (br s, 1H), 7.50-7.26 (m, 5H), 6.95 (d, 2H, J=8.6 Hz), 6.85 (d, 2H, J=8.5 Hz), 6.02 (s, 1H), 3.68 (s, 3H), 3.68-3.50 (m, 4H), 3.28-3.00 (m, 6H), 2.59 (t, 2H, J=7.1 Hz), 2.18-2.20 (m, 2H), 1.35 (s, 9H)

Example 8

4-(3-(1-tert-butyl-5-phenyl-1H-pyrazol-3-yl)propyl)-2-methyl-1-m-tolylpiperazine (Compound 8)

64 mg (44%) of target compound was obtained by using a method same as in Example 1 by using 3-(1-tert-butyl-5-phenyl-1H-pyrazol-3-yl)propanal (80 mg, 0.312 mmol), 2-methyl-1-m-tolylpiperazine (59 mg, 0.312 mmol), DIPEA (82 mL, 0.468 mmol) and NaBH(OAc)$_3$ (198 mg, 0.936 mmol).

$^1$H NMR (400 MHz, MeOH-d$_4$) δ 7.62-7.41 (m, 8H), 7.41-7.28 (m, 1H), 6.57 (s, 1H), 4.48-4.32 (m, 1H), 4.21-4.06 (m, 1H), 4.06-3.74 (m, 4H), 3.74-3.58 (m, 1H), 3.58-3.30 (m, 2H), 3.14-2.97 (m, 2H), 2.43 (s, 3H), 2.41-2.24 (m, 2H), 1.59 (s, 9H), 1.21 (d, 3H, J=4.9 Hz)

Example 9

1-(3-(1-tert-butyl-5-phenyl-1H-pyrazol-3-yl)propyl)-4-(3,4-dichlorophenyl)piperazine (Compound 9)

74 mg (47%) of target compound was obtained by using a method same as in Example 1 by using 3-(1-tert-butyl-5-phenyl-1H-pyrazol-3-yl)propanal (80 mg, 0.312 mmol), 1-(3,4-dichlorophenyl)piperazine (72 mg, 0.312 mmol), DIPEA (82 mL, 0.468 mmol) and NaBH(OAc)$_3$ (198 mg, 0.936 mmol).

$^1$H NMR (400 MHz, MeOH-d$_4$) δ 7.58-7.34 (m, 6H), 7.22-7.17 (m, 1H), 7.00-6.98 (m, 1H), 6.32 (s, 1H), 3.98-3.83 (m, 2H), 3.79-3.66 (m, 2H), 3.99-3.00 (m, 6H), 2.88 (t, 2H, J=6.9 Hz), 2.32-2.18 (m, 2H), 1.51 (s, 9H)

Example 10

1-(3-(1-tert-butyl-3-phenyl-1H-pyrazol-5-yl)propyl)-4-(bis(4-fluorophenyl)methyl)piperazine (Compound 10)

111 mg (63%) of target compound was obtained by using a method same as in Example 1 by using 3-(1-tert-butyl-5-phenyl-1H-pyrazol-3-yl)propanal (80 mg, 0.312 mmol), 1-(bis(4-fluorophenyl)methyl)piperazine (90 mg, 0.312 mmol), DIPEA (82 mL, 0.468 mmol) and NaBH(OAc)$_3$ (198 mg, 0.936 mmol).

$^1$H NMR (400 MHz, MeOH-d$_4$) δ 7.76-7.57 (m, 4H), 7.51-7.33 (m, 5H), 7.12 (t, 4H, J=8.4 Hz), 6.24 (s, 1H), 3.71-3.43 (m, 4H), 3.36-2.87 (m, 11H), 2.82 (t, 2H, J=7.1 Hz), 2.24-2.09 (m, 2H), 1.48 (s, 9H)

Example 11

1-phenyl-4-(3-(1,5-diphenyl-1H-pyrazol-3-yl)propyl)piperazine (Compound 11)

100 mg (94%) of target compound was obtained by using a method same as in Example 1 by using 3-(1,5-diphenyl-1H-pyrazol-3-yl)propanal (76 mg, 0.275 mmol), 1-phenylpiperazine (0.038 mL, 0.250 mmol), DIPEA (44 mL, 0.250 mmol) and NaBH(OAc)$_3$ (185 mg, 0.875 mmol).

$^1$H NMR (300 MHz, CDCl$_3$) δ 7.33-7.21 (m, 10H), 6.95 (d, 1H, J=8.1 Hz), 6.87 (t, 2H, J=7.3 Hz), 6.37 (s, 1H), 3.34-3.19 (m, 4H), 2.83-2.69 (m, 4H), 2.80 (t, 2H, J=7.6 Hz), 2.63 (t, 2H, J=7.5 Hz), 2.10-1.92 (m, 2H)

Example 12

1-(2-fluorophenyl)-4-(3-(1,5-diphenyl-1H-pyrazol-3-yl)propyl)piperazine (Compound 12)

74 mg (83%) of target compound was obtained by using a method same as in Example 1 by using 3-(1,5-diphenyl-1H-pyrazol-3-yl)propanal (55 mg, 0.199 mmol), 1-(2-fluorophenyl)piperazine (0.026 mL, 0.166 mmol), DIPEA (35 mL, 0.199 mmol) and NaBH(OAc)$_3$ (148 mg, 0.697 mmol).

$^1$H NMR (400 MHz, MeOH-d$_4$) δ 7.54-7.43 (m, 3H), 7.43-7.22 (m, 7H), 7.14-6.99 (m, 4H), 6.79 (s, 1H), 3.82-3.63 (m, 2H), 3.63-3.50 (m, 2H), 3.43-3.25 (m, 4H), 3.21-3.06 (m, 2H), 3.02-2.90 (m, 2H), 2.42-2.23 (m, 2H)

Example 13

1-(4-chlorophenyl)-4-(3-(1,5-diphenyl-1H-pyrazol-3-yl)propyl)piperazine (Compound 13)

106 mg (74%) of target compound was obtained by using a method same as in Example 1 by using 3-(1,5-diphenyl-1H-pyrazol-3-yl)propanal (80 mg, 0.289 mmol), 1-(4-chlorophenyl)piperazine (78 mg, 0.289 mmol), DIPEA (76 mL, 0.434 mmol) and NaBH(OAc)$_3$ (184 mg, 0.868 mmol).

$^1$H NMR (400 MHz, MeOH-d$_4$) δ 7.50-7.42 (m, 3H), 7.42-7.30 (m, 5H), 7.30-7.22 (m, 4H), 7.00 (d, 2H, J=8.8 Hz), 6.75 (s, 1H), 3.91-3.62 (m, 4H), 3.43-3.19 (m, 4H), 3.19-2.90 (m, 2H), 3.00 (t, 2H, J=6.5 Hz), 2.40-2.22 (m, 2H)

Example 14

1-(2,4-dimethylphenyl)-4-(3-(1,5-diphenyl-1H-pyrazol-3-yl)propyl)piperazine (Compound 14)

91 mg (64%) of target compound was obtained by using a method same as in Example 1 by using 3-(1,5-diphenyl-1H-pyrazol-3-yl)propanal (80 mg, 0.289 mmol), 1-(2,4-dimethylphenyl)piperazine (55 mg, 0.289 mmol), DIPEA (76 mL, 0.434 mmol) and NaBH(OAc)$_3$ (184 mg, 0.868 mmol).

$^1$H NMR (400 MHz, MeOH-d$_4$) δ 7.52-7.43 (m, 3H), 7.42-7.23 (m, 7H), 7.03 (s, 1H), 7.00 (d, 1H, J=8.3 Hz), 6.94 (d, 1H, J=8.1 Hz), 6.74 (s, 1H), 3.83-3.60 (m, 2H), 3.48-3.29 (m, 4H), 3.29-3.01 (m, 4H), 2.97 (t, 2H, J=6.1 Hz), 2.40-2.24 (m, 2H), 2.29 (s, 3H), 2.26 (s, 3H)

Example 15

1-(3,4-dimethylphenyl)-4-(3-(1,5-diphenyl-1H-pyrazol-3-yl)propyl)piperazine (Compound 15)

74 mg (83%) of target compound was obtained by using a method same as in Example 1 by using 3-(1,5-diphenyl-1H-pyrazol-3-yl)propanal (55 mg, 0.199 mmol), 1-(3,4-dimethylphenyl)piperazine (32 mg, 0.166 mmol), DIPEA (0.035 mL, 0.199 mmol) and NaBH(OAc)$_3$ (148 mg, 0.697 mmol).

$^1$H NMR (400 MHz, MeOH-d$_4$) δ 7.41-7.18 (m, 10H), 7.11 (d, 1H, J=8.4 Hz), 6.87 (s, 1H), 6.79 (d, 1H, J=7.6 Hz), 6.58

(s, 1H), 3.97-3.50 (m, 4H), 4.41-4.32 (m, 4H), 3.23-2.98 (m, 2H), 2.98-2.81 (m, 2H), 2.35-2.25 (m, 2H), 2.24 (s, 3H), 2.19 (s, 3H)

Example 16

1-(2,3-dimethylphenyl)-4-(3-(1,5-diphenyl-1H-pyrazol-3-yl)propyl)piperazine (Compound 16)

77 mg (81%) of target compound was obtained by using a method same as in Example 1 by using 3-(1,5-diphenyl-1H-pyrazol-3-yl)propanal (64 mg, 0.231 mmol), 1-(2,3-dimethylphenyl)piperazine (40 mg, 0.210 mmol), DIPEA (0.037 mL, 0.210 mmol) and NaBH(OAc)$_3$ (156 mg, 0.735 mmol).
$^1$H NMR (400 MHz, MeOH-d$_4$) δ 7.49-7.42 (m, 3H), 7.40-7.22 (m, 7H), 7.07 (t, 1H, J=7.7 Hz), 7.00 (d, 1H, J=7.4 Hz), 6.87 (d, 1H, J=7.9 Hz), 6.60 (s, 1H), 3.79-3.60 (m, 2H), 3.42-3.25 (m, 4H), 3.25-3.11 (m, 2H), 3.09-2.98 (m, 2H), 2.95 (t, 2H, J=6.9 Hz), 2.36-2.20 (m, 2H), 2.26 (s, 3H), 2.24 (s, 3H)

Example 17

1-(4-methoxyphenyl)-4-(3-(1,5-diphenyl-1H-pyrazol-3-yl)propyl)piperazine (Compound 17)

64 mg (93%) of target compound was obtained by using a method same as in Example 1 by using 3-(1,5-diphenyl-1H-pyrazol-3-yl)propanal (46 mg, 0.166 mmol), 1-(4-methoxyphenyl)piperazine (40 mg, 0.151 mmol), DIPEA (0.026 mL, 0.151 mmol) and NaBH(OAc)$_3$ (96 mg, 0.453 mmol).
$^1$H NMR (400 MHz, MeOH-d$_4$) δ 7.49-7.37 (m, 3H), 7.37-7.30 (m, 5H), 7.30-7.21 (m, 2H), 7.19 (d, 2H, J=6.6 Hz), 6.94 (d, 2H, J=7.4 Hz), 6.63 (s, 1H), 3.77 (s, 3H), 3.73-3.45 (m, 8H), 3.45-3.33 (m, 2H), 3.02-2.81 (m, 2H), 2.40-2.20 (m, 2H)

Example 18

2-methyl-4-(3-(1,5-diphenyl-1H-pyrazol-3-yl)propyl)-1-m-tolylpiperazine (Compound 18)

107 mg (66%) of target compound was obtained by using a method same as in Example 1 by using 3-(1,5-diphenyl-1H-pyrazol-3-yl)propanal (110 mg, 0.398 mmol), 2-methyl-1-m-tolylpiperazine (69 mg, 0.362 mmol), DIPEA (0.063 mL, 0.362 mmol) and NaBH(OAc)$_3$ (269 mg, 1.267 mmol).
$^1$H NMR (400 MHz, MeOH-d$_4$) δ 7.57-7.12 (m, 14H), 6.64 (s, 1H), 4.40-4.20 (m, 1H), 4.09-3.68 (m, 5H), 3.68-3.54 (m, 1H), 3.54-3.37 (m, 2H), 3.06-2.83 (m, 2H), 2.49-2.19 (m, 2H), 2.41 (s, 3H), 1.26-1.03 (m, 3H)

Example 19

1-(3,4-dichlorophenyl)-4-(3-(1,5-diphenyl-1H-pyrazol-3-yl)propyl)piperazine (Compound 19)

110 mg (72%) of target compound was obtained by using a method same as in Example 1 by using 3-(1,5-diphenyl-1H-pyrazol-3-yl)propanal (80 mg, 0.289 mmol), 1-(3,4-dichlorophenyl)piperazine (67 mg, 0.289 mmol), DIPEA (0.076 mL, 0.434 mmol) and NaBH(OAc)$_3$ (184 mg, 0.868 mmol).
$^1$H NMR (400 MHz, MeOH-d$_4$) δ 7.52-7.39 (m, 3H), 7.39-7.30 (m, 6H), 7.30-7.22 (m, 2H), 7.14-7.08 (m, 1H), 6.98-6.87 (m, 1H), 6.72 (s, 1H), 4.90-4.78 (m, 2H), 4.78-4.67 (m, 2H), 4.42-4.19 (m, 6H), 4.13-4.30 (m, 2H), 2.96 (t, 2H, J=6.5 Hz), 2.38-2.21 (m, 2H)

Example 20

1-(bis(4-fluorophenyl)methyl)-4-(3-(1,5-diphenyl-1H-pyrazol-3-yl)propyl)piperazine (Compound 20)

126 mg (75%) of target compound was obtained by using a method same as in Example 1 by using 3-(1,5-diphenyl-1H-pyrazol-3-yl)propanal (80 mg, 0.289 mmol), 1-(bis(4-fluorophenyl)methyl)piperazine (83 mg, 0.289 mmol), DIPEA (0.076 mL, 0.434 mmol) and NaBH(OAc)$_3$ (184 mg, 0.868 mmol).
$^1$H NMR (400 MHz, MeOH-d$_4$) δ 7.88-7.64 (m, 4H), 7.47-7.38 (m, 3H), 7.37-7.24 (m, 5H), 7.24-7.19 (m, 2H), 7.19-7.04 (m, 4H), 6.60 (s, 1H), 3.81-3.54 (m, 4H), 3.42-3.04 (m, 6H), 2.89 (t, 2H, J=6.8 Hz), 2.32-2.12 (m, 2H)

Example 21

1-(3-(1-tert-butyl-5-p-tolyl-1H-pyrazol-3-yl)propyl)-4-phenylpiperazine (Compound 21)

91 mg (90%) of target compound was obtained by using a method same as in Example 1 by using 3-(1-tert-butyl-5-p-tolyl-1H-pyrazol-3-yl)propanal (60 mg, 0.222 mmol), 1-phenylpiperazine (0.033 mL, 0.222 mmol), DIPEA (0.06 mL, 0.333 mmol) and NaBH(OAc)$_3$ (141 mg, 0.666 mmol).
$^1$H NMR (400 MHz, MeOH-d$_4$) δ 7.50-7.28 (m, 6H), 7.28-7.17 (m, 2H), 7.08 (t, 1H, J=6.7 Hz), 6.65 (s, 1H), 3.94-3.48 (m, 8H), 3.44-3.33 (m, 2H), 3.12-2.95 (m, 2H), 2.44 (s, 3H), 2.40-2.20 (m, 2H), 1.62 (s, 9H)

Example 22

1-(3-(1-tert-butyl-5-p-tolyl-1H-pyrazol-3-yl)propyl)-4-(2-fluorophenyl)piperazine (Compound 22)

79 mg (76%) of target compound was obtained by using a method same as in Example 1 by using 3-(1-tert-butyl-5-p-tolyl-1H-pyrazol-3-yl)propanal (60 mg, 0.222 mmol), 1-(2-fluorophenyl)piperazine (40 mg, 0.222 mmol), DIPEA (0.06 mL, 0.333 mmol) and NaBH(OAc)$_3$ (141 mg, 0.666 mmol).
$^1$H NMR (400 MHz, MeOH-d$_4$) δ 7.48-7.19 (m, 4H), 7.09-6.84 (m, 4H), 6.54 (s, 1H), 3.80-3.43 (m, 4H), 3.30-3.05 (m, 6H), 2.98-2.81 (m, 2H), 2.33 (s, 3H), 2.30-2.13 (m, 2H), 1.51 (s, 9H)

Example 23

1-(3-(1-tert-butyl-5-p-tolyl-1H-pyrazol-3-yl)propyl)-4-(4-chlorophenyl)piperazine (Compound 23)

82 mg (76%) of target compound was obtained by using a method same as in Example 1 by using 3-(1-tert-butyl-5-p-tolyl-1H-pyrazol-3-yl)propanal (60 mg, 0.222 mmol), 1-(4-chlorophenyl)piperazine (60 mg, 0.222 mmol), DIPEA (0.06 mL, 0.333 mmol) and NaBH(OAc)$_3$ (141 mg, 0.666 mmol).
$^1$H NMR (400 MHz, MeOH-d$_4$) δ 7.49-7.21 (m, 6H), 7.11-6.95 (m, 2H), 6.65 (s, 1H), 3.97-3.56 (m, 4H), 3.50-3.17 (m, 6H), 3.11-2.90 (m, 2H), 2.44 (s, 3H), 2.40-2.21 (m, 2H), 1.62 (s, 9H)

Example 24

1-(3-(1-tert-butyl-5-p-tolyl-1H-pyrazol-3-yl)propyl)-4-(2,4-dimethylphenyl)piperazine (Compound 24)

88 mg (82%) of target compound was obtained by using a method same as in Example 1 by using 3-(1-tert-butyl-5-p- tolyl-1H-pyrazol-3-yl)propanal (60 mg, 0.222 mmol), 1-(2,4-dimethylphenyl)piperazine (42 mg, 0.222 mmol), DIPEA (0.06 mL, 0.333 mmol) and NaBH(OAc)$_3$ (141 mg, 0.666 mmol).

$^1$H NMR (400 MHz, MeOH-d$_4$) δ 7.50-7.28 (m, 4H), 7.09-6.97 (m, 3H), 6.62 (s, 1H), 3.90-3.57 (m, 2H), 3.56-3.32 (m, 4H), 3.27-3.16 (m, 4H), 3.10-2.96 (m, 2H), 2.44 (s, 3H), 2.40-2.27 (m, 2H), 2.31 (s, 3H), 2.25 (s, 3H), 1.61 (s, 9H)

Example 25

1-(3-(1-tert-butyl-5-p-tolyl-1H-pyrazol-3-yl)propyl)-4-(3,4-dimethylphenyl)piperazine (Compound 25)

89 mg (84%) of target compound was obtained by using a method same as in Example 1 by using 3-(1-tert-butyl-5-p-tolyl-1H-pyrazol-3-yl)propanal (60 mg, 0.222 mmol), 1-(3,4-dimethylphenyl)piperazine (42 mg, 0.222 mmol), DIPEA (0.06 mL, 0.333 mmol) and NaBH(OAc)$_3$ (141 mg, 0.666 mmol).

$^1$H NMR (400 MHz, MeOH-d$_4$) δ 7.49-7.30 (m, 4H), 7.22-7.07 (m, 3H), 6.62 (s, 1H), 3.91-3.60 (m, 8H), 3.52-3.39 (m, 2H), 3.11-2.97 (m, 2H), 2.43 (s, 3H), 2.40-2.30 (m, 2H), 2.30 (s, 3H), 2.25 9s, 3H), 1.60 (s, 9H)

Example 26

1-(3-(1-tert-butyl-5-p-tolyl-1H-pyrazol-3-yl)propyl)-4-(2,3-dimethylphenyl)piperazine (Compound 26)

82 mg (77%) of target compound was obtained by using a method same as in Example 1 by using 3-(1-tert-butyl-5-p-tolyl-1H-pyrazol-3-yl)propanal (60 mg, 0.222 mmol), 1-(2,3-dimethylphenyl)piperazine (42 mg, 0.222 mmol), DIPEA (0.06 mL, 0.333 mmol) and NaBH(OAc)$_3$ (141 mg, 0.666 mmol).

$^1$H NMR (400 MHz, DMSO-d$_6$) δ 11.04 (br s, 1H), 7.27-7.16 (m, 4H), 7.05 (t, 1H, J=7.5 Hz), 6.94-6.81 (m, 2H), 5.98 (s, 1H), 3.58-3.47 (m, 2H), 3.24-3.11 (m, 4H), 3.11-3.01 (m, 4H), 2.58 (t, 2H, J=7.1 Hz), 2.33 (s, 3H), 2.19 (s, 3H), 2.14 (s, 3H), 2.11-2.00 (m, 2H), 1.34 (s, 9H)

Example 27

1-(3-(1-tert-butyl-5-p-tolyl-1H-pyrazol-3-yl)propyl)-4-(4-methoxyphenyl)piperazine (Compound 27)

77 mg (72%) of target compound was obtained by using a method same as in Example 1 by using 3-(1-tert-butyl-5-p-tolyl-1H-pyrazol-3-yl)propanal (60 mg, 0.222 mmol), 1-(4-methoxyphenyl)piperazine (43 mg, 0.222 mmol), DIPEA (0.06 mL, 0.333 mmol) and NaBH(OAc)$_3$ (141 mg, 0.666 mmol).

$^1$H NMR (400 MHz, DMSO-d$_6$) δ 11.35 (br s, 1H), 9.72 (br s, 1H), 7.25-7.16 (m, 4H), 7.05 (d, 2H, J=8.2 Hz), 6.88 (d, 2H, J=8.4 Hz), 5.99 (s, 1H), 3.68 (s, 3H), 3.64-3.49 (m, 4H), 3.29-3.11 (m, 4H), 2.58 (t, 2H, J=6.9 Hz), 2.33 (s, 3H), 2.13-2.01 (m, 2H), 1.34 (s, 9H)

Example 28

4-(3-(1-tert-butyl-5-p-tolyl-1H-pyrazol-3-yl)propyl)-2-methyl-1-m-tolylpiperazine (Compound 28)

71 mg (66%) of target compound was obtained by using a method same as in Example 1 by using 3-(1-tert-butyl-5-p-tolyl-1H-pyrazol-3-yl)propanal (60 mg, 0.222 mmol), 2-methyl-1-m-tolylpiperazine (42 mg, 0.222 mmol), DIPEA (0.06 mL, 0.333 mmol) and NaBH(OAc)$_3$ (141 mg, 0.666 mmol).

$^1$H NMR (400 MHz, MeOH-d$_4$) δ 7.68-7.41 (m, 3H), 7.41-7.20 (m, 5H), 6.60 (s, 1H), 4.46 (bs, 1H), 4.28-4.10 (m, 1H), 4.06-3.76 (m, 4H), 6.76-3.60 (m, 1H), 3.60-3.33 (m, 2H), 3.13-2.92 (m, 2H), 2.53-2.20 (m, 2H), 2.24 (s, 6H), 1.59 (s, 9H), 1.27-1.10 (m, 3H)

Example 29

1-(3-(1-tert-butyl-5-p-tolyl-1H-pyrazol-3-yl)propyl)-4-(3,4-dichlorophenyl)piperazine (Compound 29)

99 mg (85%) of target compound was obtained by using a method same as in Example 1 by using 3-(1-tert-butyl-5-p-tolyl-1H-pyrazol-3-yl)propanal (60 mg, 0.222 mmol), 1-(3,4-dichlorophenyl)piperazine (51 mg, 0.222 mmol), DIPEA (0.06 mL, 0.333 mmol) and NaBH(OAc)$_3$ (141 mg, 0.666 mmol).

$^1$H NMR (400 MHz, DMSO-d$_6$) δ 11.87 (bs, 1H), 11.37 (bs, 1H), 7.43 (d, 1H, J=8.6 Hz), 7.26-7.13 (m, 5H), 6.98 (d, 1H, J=8.5 Hz), 3.90-3.78 (m, 2H), 3.56-3.43 (m, 2H), 3.30-3.19 (m, 2H), 3.19-2.98 (m, 4H), 2.60-2.49 (m, 2H), 2.48 (s, 3H), 2.33 (s, 3H), 2.12-1.97 (m, 2H), 1.34 (s, 9H)

Example 30

1-(3-(1-tert-butyl-5-p-tolyl-1H-pyrazol-3-yl)propyl)-4-(bis(4-fluorophenyl)methyl)piperazine (Compound 30)

111 mg (86%) of target compound was obtained by using a method same as in Example 1 by using 3-(1-tert-butyl-5-p-tolyl-1H-pyrazol-3-yl)propanal (60 mg, 0.222 mmol), 1-(bis(4-fluorophenyl)methyl)piperazine (64 mg, 0.222 mmol), DIPEA (0.06 mL, 0.333 mmol) and NaBH(OAc)$_3$ (141 mg, 0.666 mmol).

$^1$H NMR (400 MHz, DMSO-d$_6$) δ 8.30-7.59 (m, 4H), 7.36-7.10 (m, 8H), 5.94 (s, 1H), 4.01-2.88 (m, 10H), 2.62-2.49 (m, 2H), 2.48 (s, 3H), 2.32 (s, 3H), 2.02-1.91 (m, 2H), 1.32 (s, 9H)

Example 31

1-phenyl-4-(3-(1-phenyl-5-p-tolyl-1H-pyrazol-3-yl)propyl)piperazine (Compound 31)

116 mg (89%) of target compound was obtained by using a method same as in Example 1 by using 3-(1-phenyl-5-p-tolyl-1H-pyrazol-3-yl)propanal (80 mg, 0.276 mmol), 1-phenylpiperazine (0.041 mL, 0.276 mmol), DIPEA (0.072 mL, 0.414 mmol) and NaBH(OAc)$_3$ (175 mg, 0.828 mmol).

$^1$H NMR (400 MHz, MeOH-d$_4$) δ 7.62-7.44 (m, 5H), 7.41 (d, 2H, J=7.0 Hz), 7.32 (d, 2H, J=7.4 Hz), 7.25-7.11 (m, 5H), 6.95 (s, 1H), 3.98-3.53 (m, 8H), 3.52-3.40 (m, 2H), 3.11-2.98 (m, 2H), 2.53-2.38 (m, 2H), 2.34 (s, 3H)

Example 32

1-(2-fluorophenyl)-4-(3-(1-phenyl-5-p-tolyl-1H-pyrazol-3-yl)propyl)piperazine (Compound 32)

105 mg (77%) of target compound was obtained by using a method same as in Example 1 by using 3-(1-phenyl-5-p-tolyl-1H-pyrazol-3-yl)propanal (80 mg, 0.276 mmol), 1-(2-fluorophenyl)piperazine (50 mg, 0.276 mmol), DIPEA (0.072 mL, 0.414 mmol) and NaBH(OAc)$_3$ (175 mg, 0.828 mmol).

¹H NMR (400 MHz, DMSO-d₆) δ 11.18 (bs, 1H), 7.40-7.28 (m, 3H), 7.26-7.19 (m, 2H), 7.19-7.02 (m, 7H), 7.02-6.97 (m, 1H), 6.51 (s, 1H), 3.60-3.52 (m, 2H), 3.49-3.39 (m, 2H), 3.27-3.09 (m, 6H), 2.70 (t, 2H, J=7.3 Hz), 2.27 (s, 3H), 2.21-2.09 (m, 2H)

Example 33

1-(4-chlorophenyl)-4-(3-(1-phenyl-5-p-tolyl-1H-pyrazol-3-yl)propyl)piperazine (Compound 33)

73 mg (52%) of target compound was obtained by using a method same as in Example 1 by using 3-(1-phenyl-5-p-tolyl-1H-pyrazol-3-yl)propanal (80 mg, 0.276 mmol), 1-(4-chlorophenyl)piperazine (74 mg, 0.276 mmol), DIPEA (0.072 mL, 0.414 mmol) and NaBH(OAc)₃ (175 mg, 0.828 mmol).
¹H NMR (400 MHz, MeOH-d₄) δ 7.63-7.42 (m, 5H), 7.31-7.17 (m, 6H), 7.13-7.05 (m, 2H), 7.02 (s, 1H), 4.01-3.65 (m, 4H), 3.54-3.21 (m, 6H), 3.14-2.99 (m, 2H), 2.50-2.37 (m, 2H), 2.34 (s, 3H)

Example 34

1-(2,4-dimethylphenyl)-4-(3-(1-phenyl-5-p-tolyl-1H-pyrazol-3-yl)propyl)piperazine (Compound 34)

113 mg (82%) of target compound was obtained by using a method same as in Example 1 by using 3-(1-phenyl-5-p-tolyl-1H-pyrazol-3-yl)propanal (80 mg, 0.276 mmol), 1-(2,4-dimethylphenyl)piperazine (53 mg, 0.276 mmol), DIPEA (0.072 mL, 0.414 mmol) and NaBH(OAc)₃ (175 mg, 0.828 mmol).
¹H NMR (400 MHz, DMSO-d₆) δ 11.00 (bs, 1H), 7.40-7.30 (m, 3H), 7.23 (d, 2H, J=7.7 Hz), 7.14 (d, 2H, J=7.9 Hz), 7.08 (d, 2H, J=8.0 Hz), 7.00-6.88 (m, 3H), 6.51 (s, 1H), 3.60-3.48 (m, 2H), 3.28-3.09 (m, 4H), 3.09-2.09 (m, 4H), 2.71 (t, 2H, J=7.3 Hz), 2.27 (s, 3H), 2.22-2.03 (m, 2H), 2.20 (s, 6H)

Example 35

1-(3,4-dimethylphenyl)-4-(3-(1-phenyl-5-p-tolyl-1H-pyrazol-3-yl)propyl)piperazine (Compound 35)

118 mg (85%) of target compound was obtained by using a method same as in Example 1 by using 3-(1-phenyl-5-p-tolyl-1H-pyrazol-3-yl)propanal (80 mg, 0.276 mmol), 1-(3,4-dimethylphenyl)piperazine (53 mg, 0.276 mmol), DIPEA (0.072 mL, 0.414 mmol) and NaBH(OAc)₃ (175 mg, 0.828 mmol).
¹H NMR (400 MHz, DMSO-d₆) δ 11.20 (bs, 1H), 7.40-3.27 (m, 3H), 7.23-7.16 (m, 2H), 7.13 (d, 2H, J=7.8 Hz), 7.08 (d, 2H, J=7.7 Hz), 7.00 (d, 1H, J=8.1 Hz), 6.82 (s, 1H), 6.73 (d, 1H, J=7.5 Hz), 6.51 (s, 1H), 3.77-3.60 (m, 2H), 3.60-3.47 (m, 2H), 3.24-3.01 (m, 6H), 2.70 (t, 2H, J=7.0 Hz), 2.27 (s, 3H), 2.22-2.10 (m, 2H), 2.16 (s, 3H), 2.11 (s, 3H)

Example 36

1-(2,3-dimethylphenyl)-4-(3-(1-phenyl-5-p-tolyl-1H-pyrazol-3-yl)propyl)piperazine (Compound 36)

104 mg (75%) of target compound was obtained by using a method same as in Example 1 by using 3-(1-phenyl-5-p-tolyl-1H-pyrazol-3-yl)propanal (80 mg, 0.276 mmol), 1-(2,3-dimethylphenyl)piperazine (53 mg, 0.276 mmol), DIPEA (0.072 mL, 0.414 mmol) and NaBH(OAc)₃ (175 mg, 0.828 mmol).
¹H NMR (400 MHz, MeOH-d₄) δ 7.50-7.42 (m, 3H), 7.42-7.30 (m, 2H), 7.20-7.10 (m, 4H), 7.07 (t, 1H, J=7.5 Hz), 6.95 (d, 1H, J=7.3 Hz), 6.89 (d, 1H, J=7.6 Hz), 6.70 (s, 1H), 3.83-3.58 (m, 2H), 3.48-3.31 (m, 4H), 3.21-3.10 (m, 2H), 3.10-2.99 (m, 2H), 2.99-2.87 (m, 2H), 2.39-2.29 (m, 2H), 2.32 (s, 3H), 2.26 (s, 3H), 2.25 (s, 3H)

Example 37

1-(4-methoxyphenyl)-4-(3-(1-phenyl-5-p-tolyl-1H-pyrazol-3-yl)propyl)piperazine (Compound 37)

108 mg (78%) of target compound was obtained by using a method same as in Example 1 by using 3-(1-phenyl-5-p-tolyl-1H-pyrazol-3-yl)propanal (80 mg, 0.276 mmol), 1-(4-methoxyphenyl)piperazine (53 mg, 0.276 mmol), DIPEA (0.072 mL, 0.414 mmol) and NaBH(OAc)₃ (175 mg, 0.828 mmol).
¹H NMR (400 MHz, DMSO-d₆) δ 11.48 (bs, 1H), 7.44-7.26 (m, 3H), 7.22 (d, 2H, J=7.0 Hz), 7.17-6.99 (m, 6H), 6.89 (d, 2H, J=7.1 Hz), 6.51 (s, 1H), 3.69 (s, 3H), 3.61-3.50 (m, 4H), 3.38-3.12 (m, 6H), 2.80-2.60 (m, 2H), 2.26 (s, 3H), 2.20-2.08 (m, 2H)

Example 38

2-methyl-4-(3-(1-phenyl-5-p-tolyl-1H-pyrazol-3-yl)propyl)-1-m-tolylpiperazine (Compound 38)

112 mg (81%) of target compound was obtained by using a method same as in Example 1 by using 3-(1-phenyl-5-p-tolyl-1H-pyrazol-3-yl)propanal (80 mg, 0.276 mmol), 2-methyl-1-m-tolylpiperazine (53 mg, 0.276 mmol), DIPEA (0.072 mL, 0.414 mmol) and NaBH(OAc)₃ (175 mg, 0.828 mmol).
¹H NMR (400 MHz, DMSO-d₆) δ 7.50-7.40 (m, 2H), 7.40-7.24 (m, 4H), 7.22 (d, 2H, J=7.1 Hz), 7.13 (s, 2H, J=7.8 Hz), 7.08 (d, 2H, J=7.6 Hz), 6.51 (s, 1H), 4.47-4.20 (m, 1H), 4.13-3.83 (m, 2H), 3.83-3.71 (m, 1H), 3.71-3.49 (m, 3H), 3.49-3.10 (m, 4H), 2.80-2.62 (m, 2H), 2.34 (s, 3H), 2.26 (s, 6H)

Example 39

1-(3,4-dichlorophenyl)-4-(3-(1-phenyl-5-p-tolyl-1H-pyrazol-3-yl)propyl)piperazine (Compound 39)

114 mg (76%) of target compound was obtained by using a method same as in Example 1 by using 3-(1-phenyl-5-p-tolyl-1H-pyrazol-3-yl)propanal (80 mg, 0.276 mmol), 1-(3,4-dichlorophenyl)piperazine (64 mg, 0.276 mmol), DIPEA (0.072 mL, 0.414 mmol) and NaBH(OAc)₃ (175 mg, 0.828 mmol).
¹H NMR (400 MHz, DMSO-d₆) δ 11.37 (bs, 1H), 7.43 (d, 1H, J=8.8 Hz), 7.40-7.29 (m, 3H), 7.29-7.14 (m, 3H), 7.13 (d, 2H, J=7.6 Hz), 7.07 (d, 2H, J=7.8 Hz), 6.98 (d, 1H, J=8.8 Hz), 6.50 (s, 1H), 3.91-3.80 (m, 2H), 3.60-3.48 (m, 2H), 3.30-3.13 (m, 4H), 3.13-3.00 (m, 2H), 2.73-2.61 (m, 2H), 2.26 (s, 3H), 2.20-2.10 (m, 2H)

Example 40

1-(bis(4-fluorophenyl)methyl)-4-(3-(1-phenyl-5-p-tolyl-1H-pyrazol-3-yl)propyl)piperazine (Compound 40)

150 mg (91%) of target compound was obtained by using a method same as in Example 1 by using 3-(1-phenyl-5-p-tolyl-1H-pyrazol-3-yl)propanal (80 mg, 0.276 mmol), 1-(bis(4- fluorophenyl)methyl)piperazine (80 mg, 0.276 mmol), DIPEA (0.072 mL, 0.414 mmol) and NaBH(OAc)$_3$ (175 mg, 0.828 mmol).

$^1$H NMR (400 MHz, DMSO-d$_6$) δ 11.30 (bs, 1H), 7.39-7.14 (m, 6H), 7.14-7.00 (m, 8H), 7.00-6.95 (m, 2H), 6.90-6.80 (m, 1H), 6.51 (s, 1H), 6.48 (s, 1H), 3.84-3.50 (m, 4H), 3.50-3.29 (m, 2H), 3.29-3.03 (m, 4H), 2.79-2.60 (m, 3H), 2.26 (s, 3H), 2.21-2.02 (m, 2H)

Example 41

1-(3-(1-tert-butyl-5-(4-methoxyphenyl)-1H-pyrazol-3-yl)propyl)-4-phenylpiperazine (Compound 41)

125 mg (90%) of target compound was obtained by using a method same as in Example 1 by using 3-(1-tert-butyl-5-(4-methoxyphenyl)-1H-pyrazol-3-yl)propanal (85 mg, 0.297 mmol), 1-phenylpiperazine (0.045 mL, 0.297 mmol), DIPEA (0.078 mL, 0.446 mmol) and NaBH(OAc)$_3$ (189 mg, 0.891 mmol).

$^1$H NMR (400 MHz, MeOH-d$_4$) δ 7.29-7.17 (m, 4H), 7.00-6.90 (m, 4H), 6.86 (t, 1H, J=7.3 Hz), 6.23 (s, 1H), 3.90-3.46 (m, 4H), 3.78 (s, 3H), 3.40-2.99 (m, 6H), 2.80 (t, 2H, J=7.5 Hz), 2.22-2.10 (m, 2H), 1.44 (s, 9H)

Example 42

1-(3-(1-tert-butyl-5-(4-methoxyphenyl)-1H-pyrazol-3-yl)propyl)-4-(2-fluorophenyl)piperazine (Compound 42)

132 mg (91%) of target compound was obtained by using a method same as in Example 1 by using 3-(1-tert-butyl-5-(4-methoxyphenyl)-1H-pyrazol-3-yl)propanal (85 mg, 0.297 mmol), 1-(2-fluorophenyl)piperazine (54 mg, 0.297 mmol), DIPEA (0.078 mL, 0.446 mmol) and NaBH(OAc)$_3$ (189 mg, 0.891 mmol).

$^1$H NMR (400 MHz, MeOH-d$_4$) δ 7.43 (d, 2H, J=7.7 Hz), 7.18-7.00 (m, 6H), 6.62 (s, 1H), 3.87 (s, 3H), 3.80-3.69 (m, 2H), 3.65-3.52 (m, 2H), 3.40-3.18 (m, 6H), 2.32 (t, 2H, J=7.5 Hz), 1.61 (s, 9H)

Example 43

1-(3-(1-tert-butyl-5-(4-methoxyphenyl)-1H-pyrazol-3-yl)propyl)-4-(4-chlorophenyl)piperazine (Compound 43)

82 mg (55%) of target compound was obtained by using a method same as in Example 1 by using 3-(1-tert-butyl-5-(4-methoxyphenyl)-1H-pyrazol-3-yl)propanal (85 mg, 0.297 mmol), 1-(4-chlorophenyl)piperazine (80 mg, 0.297 mmol), DIPEA (0.078 mL, 0.446 mmol) and NaBH(OAc)$_3$ (189 mg, 0.891 mmol).

$^1$H NMR (400 MHz, MeOH-d$_4$) δ 7.41 (dd, 2H, J=6.7 Hz, J=2.1 Hz), 7.27 (dd, 2H, J=6.8 Hz, J=2.2 Hz), 7.08 (dd, 2H, J=6.7 Hz, J=2.1 Hz), 7.02 (dd, 2H, J=6.9 Hz, J=2.2 Hz), 6.60 (s, 1H), 3.88 (s, 3H), 3.88-3.61 (m, 4H), 3.40-3.11 (m, 6H), 3.01 (t, 2H, J=7.7 Hz), 2.38-2.26 (m, 2H), 1.60 (s, 9H)

Example 44

1-(3-(1-tert-butyl-5-(4-methoxyphenyl)-1H-pyrazol-3-yl)propyl)-4-(2,4-dimethylphenyl)piperazine (Compound 44)

109 mg (74%) of target compound was obtained by using a method same as in Example 1 by using 3-(1-tert-butyl-5-(4-methoxyphenyl)-1H-pyrazol-3-yl)propanal (85 mg, 0.297 mmol), 1-(2,4-dimethylphenyl)piperazine (57 mg, 0.297 mmol), DIPEA (0.078 mL, 0.446 mmol) and NaBH(OAc)$_3$ (189 mg, 0.891 mmol).

$^1$H NMR (400 MHz, MeOH-d$_4$) δ 7.29 (d, 2H, J=8.6 Hz), 7.05-6.92 (m, 5H), 6.20 (s, 1H), 3.84 (s, 3H), 3.72-3.60 (m, 2H), 3.39-3.25 (m, 4H), 2.83 (t, 2H, J=7.5 Hz), 2.28 (s, 3H), 2.25 (s, 3H), 2.22-2.12 (m, 2H), 1.48 (s, 9H)

Example 45

1-(3-(1-tert-butyl-5-(4-methoxyphenyl)-1H-pyrazol-3-yl)propyl)-4-(3,4-dimethylphenyl)piperazine (Compound 45)

118 mg (80%) of target compound was obtained by using a method same as in Example 1 by using 3-(1-tert-butyl-5-(4-methoxyphenyl)-1H-pyrazol-3-yl)propanal (85 mg, 0.297 mmol), 1-(3,4-dimethylphenyl)piperazine (57 mg, 0.297 mmol), DIPEA (0.078 mL, 0.446 mmol) and NaBH(OAc)$_3$ (189 mg, 0.891 mmol).

$^1$H NMR (400 MHz, MeOH-d$_4$) δ 7.38 (dd, 2H, J=6.7 Hz, J=2.0 Hz), 7.10 (d, 1H, J=8.3 Hz), 7.05 (d, 2H, J=6.8 Hz), 6.97 (s, 1H), 6.88 (d, 1H, J=8.2 Hz), 6.48 (s, 1H), 3.87 (s, 3H), 3.72-3.43 (m, 8H), 3.40-3.30 (m, 2H), 2.96 (t, 2H, J=7.6 Hz), 2.37-2.25 (m, 2H), 2.28 (s, 3H), 2.21 (s, 3H), 1.57 (s, 9H)

Example 46

1-(3-(1-tert-butyl-5-(4-methoxyphenyl)-1H-pyrazol-3-yl)propyl)-4-(2,3-dimethylphenyl)piperazine (Compound 46)

118 mg (80%) of target compound was obtained by using a method same as in Example 1 by using 3-(1-tert-butyl-5-(4-methoxyphenyl)-1H-pyrazol-3-yl)propanal (85 mg, 0.297 mmol), 1-(2,3-dimethylphenyl)piperazine (57 mg, 0.297 mmol), DIPEA (0.078 mL, 0.446 mmol) and NaBH(OAc)$_3$ (189 mg, 0.891 mmol).

$^1$H NMR (400 MHz, MeOH-d$_4$) δ 7.40-7.30 (m, 2H), 7.12-7.01 (m, 3H), 6.97 (t, 2H, J=7.1 Hz), 6.44 (s, 1H), 3.87 (s, 3H), 3.78-3.60 (m, 2H), 3.41-3.32 (m, 4H), 3.28-3.09 (m, 4H), 2.94 (t, 2H, J=7.6 Hz), 2.32-2.20 (m, 2H), 2.26 (s, 3H), 2.23 (s, 3H), 1.56 (s, 9H)

Example 47

1-(3-(1-tert-butyl-5-(4-methoxyphenyl)-1H-pyrazol-3-yl)propyl)-4-(4-methoxyphenyl)piperazine (Compound 47)

107 mg (73%) of target compound was obtained by using a method same as in Example 1 by using 3-(1-tert-butyl-5-(4-methoxyphenyl)-1H-pyrazol-3-yl)propanal (85 mg, 0.297 mmol), 1-(4-methoxyphenyl)piperazine (57 mg, 0.297 mmol), DIPEA (0.078 mL, 0.446 mmol) and NaBH(OAc)$_3$ (189 mg, 0.891 mmol).

$^1$H NMR (400 MHz, MeOH-d$_4$) δ 7.39 (d, 2H, J=6.7 Hz), 7.24 (d, 2H, J=9.0 Hz), 7.06 (d, 2H, J=6.8 Hz), 6.95 (d, 2H, J=6.9 Hz), 6.52 (s, 1H), 3.87 (s, 3H), 3.78 (s, 3H), 3.75-3.53 (m, 8H), 3.42-3.33 (m, 2H), 2.99 (t, 2H, J=7.6 Hz), 2.39-2.24 (2H), 1.58 (s, 9H)

Example 48

4-(3-(1-tert-butyl-5-(4-methoxyphenyl)-1H-pyrazol-3-yl)propyl)-2-methyl-1-m-tolylpiperazine (Compound 48)

136 mg (92%) of target compound was obtained by using a method same as in Example 1 by using 3-(1-tert-butyl-5-(4-methoxyphenyl)-1H-pyrazol-3-yl)propanal (85 mg, 0.297 mmol), 2-methyl-1-m-tolylpiperazine (57 mg, 0.297 mmol), DIPEA (0.078 mL, 0.446 mmol) and NaBH(OAc)$_3$ (189 mg, 0.891 mmol).

$^1$H NMR (400 MHz, MeOH-d$_4$) δ 7.48-7.29 (m, 5H), 7.29-7.11 (m, 1H), 7.04 (d, 2H, J=8.6 Hz), 6.41 (s, 1H), 4.33-4.17 (bs, 1H), 4.02-3.60 (m, 5H), 3.60-3.50 (m, 1H), 3.50-3.37 (m, 2H), 2.95 (t, 2H, J=7.4 Hz), 2.40 (s, 3H), 2.38-2.21 (m, 2H), 1.55 (s, 9H), 1.16 (d, 3H, J=6.4 Hz)

Example 49

1-(3-(1-tert-butyl-5-(4-methoxyphenyl)-1H-pyrazol-3-yl)propyl)-4-(3,4-dichlorophenyl)piperazine (Compound 49)

143 mg (89%) of target compound was obtained by using a method same as in Example 1 by using 3-(1-tert-butyl-5-(4-methoxyphenyl)-1H-pyrazol-3-yl)propanal (85 mg, 0.297 mmol), 1-(3,4-dichlorophenyl)piperazine (69 mg, 0.297 mmol), DIPEA (0.078 mL, 0.446 mmol) and NaBH(OAc)$_3$ (189 mg, 0.891 mmol).

$^1$H NMR (400 MHz, MeOH-d$_4$) δ 7.39 (d, 2H, J=8.9 Hz), 7.30-7.20 (m, 2H), 7.20-7.15 (m, 1H), 7.00-6.92 (m, 3H), 6.14 (s, 1H), 3.95-3.80 (m, 2H), 3.85 (s, 3H), 3.75-3.61 (m, 2H), 3.33-3.19 (m, 4H), 3.19-3.08 (m, 2H), 2.80 (t, 2H, J=7.4 Hz), 2.26-2.10 (m, 2H), 1.47 (s, 9H)

Example 50

1-(3-(1-tert-butyl-5-(4-methoxyphenyl)-1H-pyrazol-3-yl)propyl)-4-(bis(4-fluorophenyl)methyl)piperazine (Compound 50)

141 mg (80%) of target compound was obtained by using a method same as in Example 1 by using 3-(1-tert-butyl-5-(4-methoxyphenyl)-1H-pyrazol-3-yl)propanal (85 mg, 0.297 mmol), 1-(bis(4-fluorophenyl)methyl)piperazine (86 mg, 0.297 mmol), DIPEA (0.078 mL, 0.446 mmol) and NaBH(OAc)$_3$ (189 mg, 0.891 mmol).

$^1$H NMR (400 MHz, MeOH-d$_4$) δ 7.83-7.58 (m, 4H), 7.32 (d, 2H, J=6.7 Hz), 7.19-7.05 (m, 4H), 7.01 (d, 2H, J=8.7 Hz), 6.32 (s, 1H), 5.30-5.00 (bs, 1H), 3.85 (s, 3H), 3.78-3.52 (m, 4H), 3.40-3.00 (m, 6H), 2.87 (t, 2H, J=7.4 Hz), 2.28-2.10 (m, 2H), 1.51 (s, 9H)

Example 51

1-(3-(5-(4-methoxyphenyl)-1-phenyl-1H-pyrazol-3-yl)propyl)-4-phenylpiperazine (Compound 51)

88 mg (69%) of target compound was obtained by using a method same as in Example 1 by using 3-(5-(4-methoxyphenyl)-1-phenyl-1H-pyrazol-3-yl)propanal (80 mg, 0.261 mmol), 1-phenylpiperazine (0.039 mL, 0.261 mmol), DIPEA (0.068 mL, 0.392 mmol) and NaBH(OAc)$_3$ (166 mg, 0.783 mmol).

$^1$H NMR (400 MHz, MeOH-d$_4$) δ 7.61-7.40 (m, 5H), 7.40-7.29 (m, 2H), 7.29-7.18 (m, 2H), 7.14 (d, 2H, J=7.5 Hz), 7.07-6.96 (m, 1H), 6.90 (d, 2H, J=6.7 Hz), 6.82 (s, 1H), 3.79 (s, 3H), 3.98-3.09 (m, 10H), 3.07-2.89 (m, 2H), 2.47-2.24 (m, 2H)

Example 52

1-(2-fluorophenyl)-4-(3-(5-(4-methoxyphenyl)-1-phenyl-1H-pyrazol-3-yl)propyl)piperazine (Compound 52)

65 mg (53%) of target compound was obtained by using a method same as in Example 1 by using 3-(5-(4-methoxyphenyl)-1-phenyl-1H-pyrazol-3-yl)propanal (75 mg, 0.245 mmol), 1-(2-fluorophenyl)piperazine (44 mg, 0.245 mmol), DIPEA (0.064 mL, 0.368 mmol) and NaBH(OAc)$_3$ (156 mg, 0.735 mmol).

$^1$H NMR (400 MHz, DMSO-d$_6$) δ 10.78 (br s, 1H), 7.43-7.27 (m, 3H), 7.23 (d, 2H, J=6.0 Hz), 7.20-6.97 (m, 6H), 6.90 (d, 2H, J=6.9 Hz), 6.48 (s, 1H), 3.73 (s, 3H), 3.67-3.52 (m, 2H), 3.52-3.40 (m, 2H), 3.30-3.10 (m, 6H), 2.70 (t, 2H, J=7.1 Hz), 2.22-2.08 (m, 2H)

Example 53

1-(4-chlorophenyl)-4-(3-(5-(4-methoxyphenyl)-1-phenyl-1H-pyrazol-3-yl)propyl)piperazine (Compound 53)

112 mg (82%) of target compound was obtained by using a method same as in Example 1 by using 3-(5-(4-methoxyphenyl)-1-phenyl-1H-pyrazol-3-yl)propanal (80 mg, 0.261 mmol), 1-(4-chlorophenyl)piperazine (70 mg, 0.261 mmol), DIPEA (0.068 mL, 0.392 mmol) and NaBH(OAc)$_3$ (166 mg, 0.783 mmol).

$^1$H NMR (400 MHz, MeOH-d$_4$) δ 7.53-7.42 (m, 3H), 7.40-7.32 (m, 2H), 7.26 (d, 2H, J=8.7 Hz), 7.20 (d, 2H, J=8.6 Hz), 6.98 (d, 2H, J=8.8 Hz), 6.88 (d, 2H, J=8.4 Hz), 6.66 (s, 1H), 3.78 (s, 3H), 3.89-3.62 (m, 4H), 3.42-3.32 (m, 2H), 3.29-3.16 (m, 2H), 3.11-2.98 (m, 2H), 2.94 (t, 2H, J=6.5 Hz), 2.38-2.22 (m, 2H)

Example 54

1-(3-(5-(4-methoxyphenyl)-1-phenyl-1H-pyrazol-3-yl)propyl)-4-(2,4-dimethylphenyl)piperazine (Compound 54)

104 mg (77%) of target compound was obtained by using a method same as in Example 1 by using 3-(5-(4-methoxyphenyl)-1-phenyl-1H-pyrazol-3-yl)propanal (80 mg, 0.261 mmol), 1-(2,4-dimethylphenyl)piperazine (50 mg, 0.261 mmol), DIPEA (0.068 mL, 0.392 mmol) and NaBH(OAc)$_3$ (166 mg, 0.783 mmol).

$^1$H NMR (400 MHz, MeOH-d$_4$) δ 7.56-7.46 (m, 3H), 7.43-7.33 (m, 2H), 7.20 (d, 2H, J=8.6 Hz), 7.07-6.96 (m, 2H), 6.96-6.83 (m, 3H), 6.66 (s, 1H), 3.79 (s, 3H), 3.80-3.61 (m, 2H), 3.47-3.23 (m, 4H), 3.23-2.98 (m, 4H), 2.95 (t, 2H, J=6.5 Hz), 2.37-2.17 (m, 2H), 2.28 (s, 3H), 2.25 (s, 3H)

Example 55

1-(3-(5-(4-methoxyphenyl)-1-phenyl-1H-pyrazol-3-yl)propyl)-4-(3,4-dimethylphenyl)piperazine (Compound 55)

105 mg (82%) of target compound was obtained by using a method same as in Example 1 by using 3-(5-(4-methoxyphenyl)-1-phenyl-1H-pyrazol-3-yl)propanal (75 mg, 0.245 mmol), 1-(3,4-dimethylphenyl)piperazine (47 mg, 0.245 mmol), DIPEA (0.064 mL, 0.368 mmol) and NaBH(OAc)$_3$ (156 mg, 0.735 mmol).

$^1$H NMR (400 MHz, DMSO-d$_6$) δ 10.63 (br s, 1H), 7.42-7.29 (m, 3H), 7.24 (d, 2H, J=7.6 Hz), 7.13 (d, 2H, J=8.5 Hz), 7.06 (t, 1H, J=7.7 Hz), 6.94-6.79 (m, 4H), 6.48 (s, 1H), 3.73 (s, 3H), 3.67-3.50 (m, 2H), 3.32-3.12 (m, 4H), 3.12-2.98 (m, 4H), 2.71 (t, 2H, J=7.3 Hz), 2.28-2.09 (m, 2H), 2.20 (s, 3H), 2.15 (s, 3H)

Example 56

1-(3-(5-(4-methoxyphenyl)-1-phenyl-1H-pyrazol-3-yl)propyl)-4-(2,3-dimethylphenyl)piperazine (Compound 56)

117 mg (93%) of target compound was obtained by using a method same as in Example 1 by using 3-(5-(4-methoxyphenyl)-1-phenyl-1H-pyrazol-3-yl)propanal (75 mg, 0.245 mmol), 1-(2,3-dimethylphenyl)piperazine (47 mg, 0.245 mmol), DIPEA (0.064 mL, 0.368 mmol) and NaBH(OAc)$_3$ (156 mg, 0.735 mmol).

$^1$H NMR (400 MHz, MeOH-d$_4$) δ 7.56-7.30 (m, 5H), 7.30-7.10 (m, 2H), 7.10-7.00 (m, 1H), 7.00-6.80 (m, 4H), 6.68 (s, 1H), 3.77 (s, 3H), 3.75-3.58 (m, 2H), 3.49-3.23 (m, 4H), 3.23-3.01 (m, 4H), 3.00-2.85 (m, 2H), 2.42-2.26 (m, 2H), 2.25 (m, 6H)

Example 57

1-(4-methoxyphenyl)-4-(3-(5-(4-methoxyphenyl)-1-phenyl-1H-pyrazol-3-yl)propyl)piperazine (Compound 57)

81 mg (64%) of target compound was obtained by using a method same as in Example 1 by using 3-(5-(4-methoxyphenyl)-1-phenyl-1H-pyrazol-3-yl)propanal (75 mg, 0.245 mmol), 1-(4-methoxyphenyl)piperazine (47 mg, 0.245 mmol), DIPEA (0.064 mL, 0.368 mmol) and NaBH(OAc)$_3$ (156 mg, 0.735 mmol).

$^1$H NMR (400 MHz, MeOH-d$_4$) δ 7.64-7.48 (m, 7H), 7.34-7.21 (m, 2H), 7.14-7.03 (m, 2H), 6.95 (s, 1H), 6.93-6.80 (m, 2H), 4.08-3.88 (m, 8H), 3.83 (s, 3H), 3.79 (s, 3H), 3.59-3.42 (m, 2H), 3.12-2.99 (m, 2H), 2.52-2.34 (m, 2H)

Example 58

4-(3-(5-(4-methoxyphenyl)-1-phenyl-1H-pyrazol-3-yl)propyl)-2-methyl-1-m-tolylpiperazine (Compound 58)

120 mg (89%) of target compound was obtained by using a method same as in Example 1 by using 3-(5-(4-methoxyphenyl)-1-phenyl-1H-pyrazol-3-yl)propanal (80 mg, 0.261 mmol), 2-methyl-1-m-tolylpiperazine (50 mg, 0.261 mmol), DIPEA (0.068 mL, 0.392 mmol) and NaBH(OAc)$_3$ (166 mg, 0.783 mmol).

$^1$H NMR (400 MHz, MeOH-d$_4$) δ 7.54-7.34 (m, 8H), 7.34-7.28 (m, 1H), 7.20 (d, 2H, J=8.5 Hz), 6.89 (d, 2H, J=8.4 Hz), 6.68 (s, 1H), 4.32-4.19 (m, 1H), 4.03-3.92 (m, 2H), 3.92-3.72 (m, 3H), 3.79 (s, 3H), 3.65-3.52 (m, 1H), 3.52-3.42 (m, 2H), 3.07-2.91 (m, 2H), 2.42 (s, 3H), 2.41-2.29 (m, 2H), 1.17 (d, 3H, J=3.1 Hz)

Example 59

1-(3,4-dichlorophenyl)-4-(3-(5-(4-methoxyphenyl)-1-phenyl-1H-pyrazol-3-yl)propyl)piperazine (Compound 59)

104 mg (76%) of target compound was obtained by using a method same as in Example 1 by using 3-(5-(4-methoxyphenyl)-1-phenyl-1H-pyrazol-3-yl)propanal (75 mg, 0.245 mmol), 1-(3,4-dichlorophenyl)piperazine (57 mg, 0.245 mmol), DIPEA (0.064 mL, 0.368 mmol) and NaBH(OAc)$_3$ (156 mg, 0.735 mmol).

$^1$H NMR (400 MHz, DMSO-d$_6$) δ 10.64 (br s, 1H), 7.43-7.27 (m, 3H), 7.23 (d, 2H, J=6.0 Hz), 7.20-6.97 (m, 6H), 6.90 (d, 2H, J=6.9 Hz), 6.48 (s, 1H), 3.73 (s, 3H), 3.67-3.52 (m, 2H), 3.52-3.40 (m, 2H), 3.30-3.10 (m, 6H), 2.70 (t, 2H, J=7.1 Hz), 2.22-2.08 (m, 2H)

Example 60

1-(bis(4-fluorophenyl)methyl)-4-(3-(5-(4-methoxyphenyl)-1-phenyl-1H-pyrazol-3-yl)propyl)piperazine (Compound 60)

127 mg (80%) of target compound was obtained by using a method same as in Example 1 by using 3-(5-(4-methoxyphenyl)-1-phenyl-1H-pyrazol-3-yl)propanal (80 mg, 0.261 mmol), 1-(bis(4-fluorophenyl)methyl)piperazine (75 mg, 0.261 mmol), DIPEA (0.068 mL, 0.392 mmol) and NaBH(OAc)$_3$ (166 mg, 0.783 mmol).

$^1$H NMR (400 MHz, MeOH-d$_4$) δ 7.81-7.59 (m, 4H), 7.53-7.39 (m, 3H), 7.37-7.22 (m, 2H), 7.21-7.06 (m, 6H), 6.86 (d, 2H, J=8.4 Hz), 6.55 (s, 1H), 5.20-4.92 (bs, 1H), 3.77 (s, 3H), 3.73-3.52 (m, 4H), 3.41-2.98 (m, 6H), 2.88 (t, 2H, J=6.3 Hz), 2.32-2.16 (m, 2H)

Example 61

1-(3-(1-tert-butyl-5-(4-chlorophenyl)-1H-pyrazol-3-yl)propyl)-4-phenylpiperazine (Compound 61)

116 mg (89%) of target compound was obtained by using a method same as in Example 1 by using 3-(1-tert-butyl-5-(4-chlorophenyl)-1H-pyrazol-3-yl)propanal (80 mg, 0.275 mmol), 1-phenylpiperazine (0.041 mL, 0.275 mmol), DIPEA (0.072 mL, 0.413 mmol) and NaBH(OAc)$_3$ (175 mg, 0.825 mmol).

$^1$H NMR (400 MHz, MeOH-d$_4$) δ 7.47-7.37 (m, 4H), 7.25 (t, 2H, J=7.6 Hz), 7.11 (d, 2H J=8.2 Hz), 6.97 (t, 1H, J=7.2 Hz), 6.51 (s, 1H), 3.82-3.36 (m, 8H), 3.33-3.22 (m, 2H), 2.98-2.86 (m, 2H), 2.29-2.12 (m, 2H), 1.48 (s, 9H)

Example 62

1-(3-(1-tert-butyl-5-(4-chlorophenyl)-1H-pyrazol-3-yl)propyl)-4-(2-fluorophenyl)piperazine (Compound 62)

105 mg (78%) of target compound was obtained by using a method same as in Example 1 by using 3-(1-tert-butyl-5-(4-chlorophenyl)-1H-pyrazol-3-yl)propanal (80 mg, 0.275 mmol), 1-(2-fluorophenyl)piperazine (50 mg, 0.275 mmol), DIPEA (0.072 mL, 0.413 mmol) and NaBH(OAc)$_3$ (175 mg, 0.825 mmol).

$^1$H NMR (400 MHz, MeOH-d$_4$) δ 7.49-7.33 (m, 4H), 7.07-6.91 (m, 4H), 6.48 (s, 1H), 3.70-3.56 (m, 2H), 3.56-3.43 (m,

2H), 3.32-3.20 (m, 4H), 3.18-3.04 (m, 2H), 2.94-2.80 (m, 2H), 2.23-2.10 (m, 2H), 1.48 (s, 9H)

Example 63

1-(3-(1-tert-butyl-5-(4-chlorophenyl)-1H-pyrazol-3-yl)propyl)-4-(4-chlorophenyl)piperazine (Compound 63)

111 mg (80%) of target compound was obtained by using a method same as in Example 1 by using 3-(1-tert-butyl-5-(4-chlorophenyl)-1H-pyrazol-3-yl)propanal (80 mg, 0.275 mmol), 1-(4-chlorophenyl)piperazine (74 mg, 0.275 mmol), DIPEA (0.072 mL, 0.413 mmol) and NaBH(OAc)$_3$ (175 mg, 0.825 mmol).
$^1$H NMR (400 MHz, MeOH-d$_4$) δ 7.48-7.34 (m, 4H), 7.14 (d, 2H, J=8.6 Hz), 6.92 (d, 2H, J=8.7 Hz), 6.53 (s, 1H), 3.88-3.46 (m, 4H), 3.31-3.01 (m, 6H), 2.93-2.82 (m, 2H), 2.23-2.12 (m, 2H), 1.47 (s, 1H)

Example 64

1-(3-(1-tert-butyl-5-(4-chlorophenyl)-1H-pyrazol-3-yl)propyl)-4-(2,4-dimethylphenyl)piperazine (Compound 64)

115 mg (84%) of target compound was obtained by using a method same as in Example 1 by using 3-(1-tert-butyl-5-(4-chlorophenyl)-1H-pyrazol-3-yl)propanal (80 mg, 0.275 mmol), 1-(2,4-dimethylphenyl)piperazine (52 mg, 0.275 mmol), DIPEA (0.072 mL, 0.413 mmol) and NaBH(OAc)$_3$ (175 mg, 0.825 mmol).
$^1$H NMR (400 MHz, MeOH-d$_4$) δ 7.61-7.48 (m, 4H), 7.110-7.01 (m, 3H), 6.65 (s, 1H), 3.88-3.60 (m, 2H), 3.54-3.21 (m, 8H), 3.08-3.01 (m, 2H), 2.38-2.28 (m, 2H), 2.33 (s, 3H), 2.27 (s, 3H), 1.61 (s, 9H)

Example 65

1-(3-(1-tert-butyl-5-(4-chlorophenyl)-1H-pyrazol-3-yl)propyl)-4-(3,4-dimethylphenyl)piperazine (Compound 65)

199 mg (87%) of target compound was obtained by using a method same as in Example 1 by using 3-(1-tert-butyl-5-(4-chlorophenyl)-1H-pyrazol-3-yl)propanal (80 mg, 0.275 mmol), 1-(3,4-dimethylphenyl)piperazine (52 mg, 0.275 mmol), DIPEA (0.072 mL, 0.413 mmol) and NaBH(OAc)$_3$ (175 mg, 0.825 mmol).
$^1$H NMR (400 MHz, MeOH-d$_4$) δ 7.49-7.36 (m, 4H), 7.13-7.09 (m, 2H), 7.07-6.99 (m, 1H), 6.45 (s, 1H), 3.78-3.57 (m, 8H), 3.36-3.26 (m, 2H), 2.94-2.82 (m, 2H), 2.29-2.17 (m, 2H), 2.19 (s, 3H), 2.15 (s, 3H), 1.47 (s, 9H)

Example 66

1-(3-(1-tert-butyl-5-(4-chlorophenyl)-1H-pyrazol-3-yl)propyl)-4-(2,3-dimethylphenyl)piperazine (Compound 66)

118 mg (85%) of target compound was obtained by using a method same as in Example 1 by using 3-(1-tert-butyl-5-(4-chlorophenyl)-1H-pyrazol-3-yl)propanal (80 mg, 0.275 mmol), 1-(2,3-dimethylphenyl)piperazine (52 mg, 0.275 mmol), DIPEA (0.072 mL, 0.413 mmol) and NaBH(OAc)$_3$ (175 mg, 0.825 mmol).
$^1$H NMR (400 MHz, MeOH-d$_4$) δ 7.48-7.36 (m, 4H), 6.97 (t, 1H, J=7.7 Hz), 6.91-6.81 (m, 2H), 6.50 (s, 1H), 3.70-3.49 (m, 2H), 3.33-3.23 (m, 4H), 3.17-3.06 (m, 4H), 2.93-2.87 (m, 2H), 2.27-2.19 (m, 2H), 2.10 (s, 6H), 1.48 (s, 9H)

Example 67

1-(3-(1-tert-butyl-5-(4-chlorophenyl)-1H-pyrazol-3-yl)propyl)-4-(4-methoxyphenyl)piperazine (Compound 67)

104 mg (75%) of target compound was obtained by using a method same as in Example 1 by using 3-(1-tert-butyl-5-(4-chlorophenyl)-1H-pyrazol-3-yl)propanal (80 mg, 0.275 mmol), 1-(4-methoxyphenyl)piperazine (53 mg, 0.275 mmol), DIPEA (0.072 mL, 0.413 mmol) and NaBH(OAc)$_3$ (175 mg, 0.825 mmol).
$^1$H NMR (400 MHz, MeOH-d$_4$) δ 7.49 (d, 2H, J=7.8 Hz), 7.42 (d, 2H, J=8.1 Hz), 7.16 (d, 2H, J=8.5 Hz), 6.93 (d, 2H, J=8.8 Hz), 6.32 (s, 1H), 3.77 (s, 3H), 3.60-3.43 (m, 8H), 3.40-3.32 (m, 2H), 2.87 (t, 2H, J=6.6 Hz), 2.31-2.17 (m, 2H), 1.51 (s, 9H)

Example 68

4-(3-(1-tert-butyl-5-(4-chlorophenyl)-1H-pyrazol-3-yl)propyl)-2-methyl-1-m-tolylpiperazine (Compound 68)

106 mg (77%) of target compound was obtained by using a method same as in Example 1 by using 3-(1-tert-butyl-5-(4-chlorophenyl)-1H-pyrazol-3-yl)propanal (80 mg, 0.275 mmol), 2-methyl-1-m-tolylpiperazine (52 mg, 0.275 mmol), DIPEA (0.072 mL, 0.413 mmol) and NaBH(OAc)$_3$ (175 mg, 0.825 mmol).
$^1$H NMR (400 MHz, MeOH-d$_4$) δ 7.54-7.47 (m, 1H), 7.47-7.33 (m, 6H), 7.30-7.21 (m, 1H), 6.43 (s, 1H), 4.41-4.30 (m, 1H), 4.13-4.01 (m, 1H), 3.97-3.87 (m, 1H), 3.87-3.72 (m, 3H), 3.67-3.52 (m, 2H), 2.92-2.81 (m, 2H), 2.34 (s, 3H), 2.30-2.17 (m, 2H), 1.47 (s, 9H), 1.12 (d, 3H, J=6.0 Hz)

Example 69

1-(3-(1-tert-butyl-5-(4-chlorophenyl)-1H-pyrazol-3-yl)propyl)-4-(3,4-dichlorophenyl)piperazine (Compound 69)

134 mg (90%) of target compound was obtained by using a method same as in Example 1 by using 3-(1-tert-butyl-5-(4-chlorophenyl)-1H-pyrazol-3-yl)propanal (80 mg, 0.275 mmol), 1-(3,4-dichlorophenyl)piperazine (64 mg, 0.275 mmol), DIPEA (0.072 mL, 0.413 mmol) and NaBH(OAc)$_3$ (175 mg, 0.825 mmol).
$^1$H NMR (400 MHz, MeOH-d$_4$) δ 7.46-7.33 (m, 4H), 7.22 (d, 1H, J=8.8 Hz), 7.04 (s, 1H), 6.82 (d, 1H, J=8.9 Hz), 6.53 (s, 1H), 3.80-3.63 (m, 2H), 3.63-3.49 (m, 2H), 3.27-3.17 (m, 2H), 3.17-3.01 (m, 4H), 2.92-2.83 (m, 2H), 2.23-2.09 (m 2H), 1.46 (s, 9H)

Example 70

1-(3-(1-tert-butyl-5-(4-chlorophenyl)-1H-pyrazol-3-yl)propyl)-4-(bis(4-fluorophenyl)methyl)piperazine (Compound 70)

123 mg (75%) of target compound was obtained by using a method same as in Example 1 by using 3-(1-tert-butyl-5-(4- chlorophenyl)-1H-pyrazol-3-yl)propanal (80 mg, 0.275 mmol), 1-(bis(4-fluorophenyl)methyl)piperazine (79 mg, 0.275 mmol), DIPEA (0.072 mL, 0.413 mmol) and NaBH(OAc)$_3$ (175 mg, 0.825 mmol).

$^1$H NMR (400 MHz, MeOH-d$_4$) δ 7.84-7.73 (m, 4H), 7.43 (d, 2H, J=7.5 Hz), 7.38 (d, 2H, J=8.1 Hz), 7.17-7.05 (m, 4H), 6.42 (s, 1H), 5.57 (s, 1H), 3.80-3.64 (m, 4H), 3.50-3.38 (m, 4H), 3.33-3.21 (m, 2H), 2.91-2.80 (m, 2H), 2.23-2.07 (m, 2H), 1.45 (s, 9H)

Example 71

1-(3-(5-(4-chlorophenyl)-1-phenyl-1H-pyrazol-3-yl)propyl)-4-phenylpiperazine (Compound 71)

121 mg (80%) of target compound was obtained by using a method same as in Example 1 by using 3-(5-(4-chlorophenyl)-1-phenyl-1H-pyrazol-3-yl)-propanal (100 mg, 0.307 mmol), 1-phenylpiperazine (0.046 mL, 0.307 mmol), DIPEA (0.080 mL, 0.461 mmol) and NaBH(OAc)$_3$ (195 mg, 0.921 mmol).

$^1$H NMR (400 MHz, MeOH-d$_4$) δ 7.46-7.35 (m, 3H), 7.35-7.24 (m, 6H), 7.22 (d, 2H, J=8.5 Hz), 7.00 (d, 2H, J=8.6 Hz), 6.98-6.90 (m, 1H), 6.60 (s, 1H), 3.91-3.63 (m, 4H), 3.39-3.20 (m, 4H), 3.11-2.94 (m, 2H), 2.91 (t, 2H, J=7.1 Hz), 2.33-2.20 (m, 2H)

Example 72

1-(3-(5-(4-chlorophenyl)-1-phenyl-1H-pyrazol-3-yl)propyl)-4-(2-fluorophenyl)piperazine (Compound 72)

108 mg (83%) of target compound was obtained by using a method same as in Example 1 by using 3-(5-(4-chlorophenyl)-1-phenyl-1H-pyrazol-3-yl)-propanal (80 mg, 0.257 mmol), 1-(2-fluorophenyl)piperazine (46 mg, 0.257 mmol), DIPEA (0.070 mL, 0.386 mmol) and NaBH(OAc)$_3$ (163 mg, 0.771 mmol).

$^1$H NMR (400 MHz, MeOH-d$_4$) δ 7.39-7.33 (m, 3H), 7.33-7.24 (m, 2H), 7.22 (d, 2H, J=8.1 Hz), 7.15 (d, 2H, J=8.4 Hz), 7.01-7.86 (m, 4H), 6.72 (s, 1H), 3.63-3.52 (m, 2H), 3.47-3.39 (m, 2H), 3.30-3.17 (m, 4H), 3.09-2.06 (m, 2H), 2.84 (t, 2H, J=6.5 Hz), 2.27-2.11 (m, 2H)

Example 73

1-(4-chlorophenyl)-4-(3-(5-(4-chlorophenyl)-1-phenyl-1H-pyrazol-3-yl)propyl)piperazine (Compound 73)

77 mg (65%) of target compound was obtained by using a method same as in Example 1 by using 3-(5-(4-chlorophenyl)-1-phenyl-1H-pyrazol-3-yl)-propanal (70 mg, 0.225 mmol), 1-(4-chlorophenyl)piperazine (61 mg, 0.225 mmol), DIPEA (0.059 mL, 0.338 mmol) and NaBH(OAc)$_3$ (143 mg, 0.675 mmol).

$^1$H NMR (400 MHz, MeOH-d$_4$) δ 7.52-7.43 (m, 3H), 7.43-7.30 (m, 4H), 7.30-7.20 (m, 4H), 7.04 (d, 2H, J=9.0 Hz), 6.84 (s, 1H), 3.93-3.62 (m, 4H), 3.42-3.09 (m, 6H), 2.98 (t, 2H, J=7.3 Hz), 2.40-2.29 (m, 2H)

Example 74

1-(3-(5-(4-chlorophenyl)-1-phenyl-1H-pyrazol-3-yl)propyl)-4-(2,4-dimethylphenyl)piperazine (Compound 74)

99 mg (74%) of target compound was obtained by using a method same as in Example 1 by using 3-(5-(4-chlorophenyl)-1-phenyl-1H-pyrazol-3-yl)-propanal (80 mg, 0.257 mmol), 1-(2,4-dimethylphenyl)piperazine (49 mg, 0.257 mmol), DIPEA (0.070 mL, 0.386 mmol) and NaBH(OAc)$_3$ (163 mg, 0.771 mmol).

$^1$H NMR (400 MHz, MeOH-d$_4$) δ 7.52-7.41 (m, 3H), 7.39-7.28 (m, 4H), 7.25 (d, 2H, J=8.3 Hz), 7.07 (s, 1H), 7.00 (d, 1H, J=8.4 Hz), 6.94 (d, 1H, J=8.1 Hz), 6.71 (s, 1H), 3.80-3.61 (m, 2H), 3.44-3.31 (m, 4H), 3.26-3.04 (m, 4H), 2.94 (t, 2H, J=6.1 Hz), 3.47-3.25 (m, 2H), 2.29 (s, 3H), 2.26 (s, 3H)

Example 75

1-(3-(5-(4-chlorophenyl)-1-phenyl-1H-pyrazol-3-yl)propyl)-4-(3,4-dimethylphenyl)piperazine (Compound 75)

99 mg (84%) of target compound was obtained by using a method same as in Example 1 by using 3-(5-(4-chlorophenyl)-1-phenyl-1H-pyrazol-3-yl)-propanal (70 mg, 0.225 mmol), 1-(3,4-dimethylphenyl)piperazine (61 mg, 0.225 mmol), DIPEA (0.059 mL, 0.338 mmol) and NaBH(OAc)$_3$ (143 mg, 0.675 mmol).

$^1$H NMR (400 MHz, MeOH-d$_4$) δ 7.50-7.40 (m, 3H), 7.40-7.30 (m, 4H), 7.30-7.13 (m, 5H), 6.73 (s, 1H), 3.97-3.62 (m, 8H), 3.50-3.41 (m, 2H), 2.95 (t, 2H, J=7.2 Hz), 2.41-2.30 (m, 2H), 2.30 (s, 3H), 2.26 (s, 3H)

Example 76

1-(3-(5-(4-chlorophenyl)-1-phenyl-1H-pyrazol-3-yl)propyl)-4-(2,3-dimethylphenyl)piperazine (Compound 76)

89 mg (67%) of target compound was obtained by using a method same as in Example 1 by using 3-(5-(4-chlorophenyl)-1-phenyl-1H-pyrazol-3-yl)-propanal (80 mg, 0.257 mmol), 1-(2,3-dimethylphenyl)piperazine (49 mg, 0.257 mmol), DIPEA (0.070 mL, 0.386 mmol) and NaBH(OAc)$_3$ (163 mg, 0.771 mmol).

$^1$H NMR (400 MHz, MeOH-d$_4$) δ 7.40-7.32 (m, 3H), 7.28-7.19 (m, 4H), 7.14 (d, 2H, J=8.4 Hz), 6.98 (t, 1H, J=7.7 Hz), 6.87 (d, 1H, J=7.4 Hz), 6.78 (d, 1H, J=7.9 Hz), 6.54 (s, 1H), 3.68-3.52 (m, 2H), 3.34-3.21 (m, 4H), 3.14-3.02 (m, 2H), 2.98-2.88 (m, 2H), 2.84 (t, 2H, J=6.6 Hz), 2.28-2.20 (m, 2H), 2.18 (s, 3H), 2.16 (s, 3H)

Example 77

1-(3-(5-(4-chlorophenyl)-1-phenyl-1H-pyrazol-3-yl)propyl)-4-(4-methoxyphenyl)piperazine (Compound 77)

85 mg (63%) of target compound was obtained by using a method same as in Example 1 by using 3-(5-(4-chlorophenyl)-1-phenyl-1H-pyrazol-3-yl)-propanal (80 mg, 0.257 mmol), 1-(4-methoxyphenyl)piperazine (50 mg, 0.257 mmol), DIPEA (0.070 mL, 0.386 mmol) and NaBH(OAc)$_3$ (163 mg, 0.771 mmol).

$^1$H NMR (400 MHz, MeOH-d$_4$) δ 7.45 (d, 2H, J=8.8 Hz), 7.39-7.32 (m, 3H), 7.30-7.24 (m, 2H), 7.24 (d, 2H, J=8.0 hz), 7.16 (d, 2H, J=8.2 Hz), 6.95 (d, 2H, J=8.7 Hz), 6.69 (s, 1H), 3.89-3.71 (m, 8H), 3.70 (s, 3H), 3.43-3.28 (m, 2H), 2.91-2.77 (m, 2H), 2.32-2.16 (m, 2H)

Example 78

4-(3-(5-(4-chlorophenyl)-1-phenyl-1H-pyrazol-3-yl)propyl)-2-methyl-1-m-tolylpiperazine (Compound 78)

114 mg (85%) of target compound was obtained by using a method same as in Example 1 by using 3-(5-(4-chlorophenyl)-1-phenyl-1H-pyrazol-3-yl)-propanal (80 mg, 0.257 mmol), 2-methyl-1-m-tolylpiperazine (49 mg, 0.257 mmol), DIPEA (0.070 mL, 0.386 mmol) and NaBH(OAc)$_3$ (163 mg, 0.771 mmol).

$^1$H NMR (400 MHz, MeOH-d$_4$) δ 7.67 (s, 1H), 7.61 (d, 1H, J=8.0 Hz), 7.56-7.44 (m, 4H), 7.44-7.34 (m, 3H), 7.36 (d, 2H, J=8.3 Hz), 7.28 (d, 2H, J=8.4 Hz), 6.79 (s, 1H), 4.59 (m, 1H), 4.33-4.19 (m, 1H), 4.17-4.04 (m, 1H), 4.04-3.89 (m, 3H), 3.84-3.72 (m, 1H), 3.57-3.42 (m, 2H), 2.99 (t, 2H, J=6.3 Hz), 2.46 (s, 3H), 2.47-2.30 (m, 2H), 1.23 (d, 3H, J=6.1 Hz)

Example 79

1-(3,4-dichlorophenyl)-4-(3-(5-(4-chlorophenyl)-1-phenyl-1H-pyrazol-3-yl)propyl)piperazine (Compound 79)

125 mg (86%) of target compound was obtained by using a method same as in Example 1 by using 3-(5-(4-chlorophenyl)-1-phenyl-1H-pyrazol-3-yl)-propanal (80 mg, 0.257 mmol), 1-(3,4-dichlorophenyl)piperazine (60 mg, 0.257 mmol), DIPEA (0.070 mL, 0.386 mmol) and NaBH(OAc)$_3$ (163 mg, 0.771 mmol).

$^1$H NMR (400 MHz, MeOH-d$_4$) δ 7.39-7.30 (m, 3H), 7.30-7.22 (m, 2H), 7.22-7.17 (m, 3H), 7.14 (d, 2H, J=8.3 Hz), 6.99 (s, 1H), 6.79 (d, 1H, J=8.7 Hz), 6.73 (s, 1H), 3.78-3.61 (m 2H), 3.61-3.48 (m, 2H), 2.27-3.16 (m, 2H), 3.16-3.07 (m, 2H), 3.07-2.94 (m, 2H), 2.88-2.72 (m, 2H), 2.24-2.10 (m, 2H)

Example 80

1-(bis(4-fluorophenyl)methyl)-4-(3-(5-(4-chlorophenyl)-1-phenyl-1H-pyrazol-3-yl)propyl)piperazine (Compound 80)

158 mg (83%) of target compound was obtained by using a method same as in Example 1 by using 3-(5-(4-chlorophenyl)-1-phenyl-1H-pyrazol-3-yl)-propanal (100 mg, 0.307 mmol), 1-phenylpiperazine (88 mg, 0.307 mmol), DIPEA (0.080 mL, 0.461 mmol) and NaBH(OAc)$_3$ (195 mg, 0.921 mmol).

$^1$H NMR (400 MHz, MeOH-d$_4$) δ 7.78-759, (m, 4H), 7.49-7.40 (m, 3H), 7.32 (d, 2H, J=8.6 Hz), 7.29-7.24 (m, 2H), 7.20 (d, 2H, J=8.7 Hz), 7.18-7.08 (m, 4H), 6.57 (s, 1H), 7.02-7.80 (bs, 1H), 3.78-3.48 (m, 4H), 3.39-3.32 (m, 2H), 3.26-2.93 (m, 4H), 2.87 (t, 2H, J=7.1 Hz), 2.31-2.15 (m, 2H)

Example 81

1-(3-(1-tert-butyl-5-(4-fluorophenyl)-1H-pyrazol-3-yl)propyl)-4-phenylpiperazine (Compound 81)

134 mg (80%) of target compound was obtained by using a method same as in Example 1 by using 3-(1-tert-butyl-5-(4-fluorophenyl)-1H-pyrazol-3-yl)propanal (100 mg, 0.365 mmol), 1-phenylpiperazine (0.055 mL, 0.365 mmol), DIPEA (0.1 mL, 0.548 mmol) and NaBH(OAc)$_3$ (232 mg, 1.095 mmol).

$^1$H NMR (400 MHz, MeOH-d$_4$) δ 7.59-4.48 (m, 2H), 7.37-7.21 (m, 4H), 7.13-7.08 (m, 2H), 7.03-6.97 (m, 1H), 6.55 (s, 1H), 3.93-3.40 (m, 8H), 3.40-3.34 (m, 2H), 2.99 (t, 2H, J=7.6 Hz), 2.38-2.23 (m, 2H), 1.58 (s, 9H)

Example 82

1-(3-(1-tert-butyl-5-(4-fluorophenyl)-1H-pyrazol-3-yl)propyl)-4-(2-fluorophenyl)piperazine (Compound 82)

142 mg (82%) of target compound was obtained by using a method same as in Example 1 by using 3-(1-tert-butyl-5-(4-fluorophenyl)-1H-pyrazol-3-yl)propanal (100 mg, 0.365 mmol), 1-(2-fluorophenyl)piperazine (66 mg, 0.365 mmol), DIPEA (0.1 mL, 0.548 mmol) and NaBH(OAc)$_3$ (232 mg, 1.095 mmol).

$^1$H NMR (400 MHz, MeOH-d$_4$) δ 7.62-7.53 (m, 2H), 7.30 (t, 2H, J=8.7 Hz), 7.18-7.03 (m, 4H), 6.69 (s, 1H), 3.79-3.69 (m, 2H), 3.66-3.57 (m, 2H), 3.43-3.36 (m, 4H), 3.35-3.21 (m, 2H), 3.05 (t, 2H, J=7.7 Hz), 2.39-2.28 (m, 2H), 1.62 (s, 9H)

Example 83

1-(3-(1-tert-butyl-5-(4-fluorophenyl)-1H-pyrazol-3-yl)propyl)-4-(4-chlorophenyl)piperazine (Compound 83)

108 mg (60%) of target compound was obtained by using a method same as in Example 1 by using 3-(1-tert-butyl-5-(4-fluorophenyl)-1H-pyrazol-3-yl)propanal (100 mg, 0.365 mmol), 1-(4-chlorophenyl)piperazine (98 mg, 0.365 mmol), DIPEA (0.1 mL, 0.548 mmol) and NaBH(OAc)$_3$ (232 mg, 1.095 mmol).

$^1$H NMR (400 MHz, MeOH-d$_4$) δ 7.61-7.53 (m, 2H), 7.34-7.23 (m, 4H), 7.09-7.00 (m, 2H), 6.65 (s, 1H), 3.98-3.58 (m, 4H), 3.41-3.13 (m, 6H), 3.03 (t, 2H, J=7.6 Hz), 2.39-2.23 (m, 2H), 1.60 (s, 9H)

Example 84

1-(3-(1-tert-butyl-5-(4-fluorophenyl)-1H-pyrazol-3-yl)propyl)-4-(2,4-dimethylphenyl)piperazine (Compound 84)

139 mg (79%) of target compound was obtained by using a method same as in Example 1 by using 3-(1-tert-butyl-5-(4-fluorophenyl)-1H-pyrazol-3-yl)propanal (100 mg, 0.365 mmol), 1-(2,4-dimethylphenyl)piperazine (69 mg, 0.365 mmol), DIPEA (0.1 mL, 0.548 mmol) and NaBH(OAc)$_3$ (232 mg, 1.095 mmol).

$^1$H NMR (400 MHz, MeOH-d$_4$) δ 7.63-7.53 (m, 2H), 7.30 (t, 2H, J=8.6 Hz), 7.12-6.08 (m, 3H), 6.67 (s, 1H), 3.84-3.44 (m, 4H), 3.44-3.22 (m, 6H), 3.05 (t, 2H, J=7.5 Hz), 2.40-2.30 (m, 2H), 2.34 (s, 3H), 2.27 (s, 3H), 1.66 (s, 9H)

Example 85

1-(3-(1-tert-butyl-5-(4-fluorophenyl)-1H-pyrazol-3-yl)propyl)-4-(3,4-dimethylphenyl)piperazine (Compound 85)

126 mg (71%) of target compound was obtained by using a method same as in Example 1 by using 3-(1-tert-butyl-5-(4-fluorophenyl)-1H-pyrazol-3-yl)propanal (100 mg, 0.365 mmol), 1-(3,4-dimethylphenyl)piperazine (69 mg, 0.365 mmol), DIPEA (0.1 mL, 0.548 mmol) and NaBH(OAc)$_3$ (232 mg, 1.095 mmol).

$^1$H NMR (400 MHz, MeOH-d$_4$) δ 7.60-7.49 (m, 2H), 7.32-7.22 (m, 2H), 7.20-7.12 (m, 2H), 7.10-7.03 (m, 1H), 6.56 (s, 1H), 3.80-3.62 (m, 8H), 3.48-3.37 (m, 2H), 3.00 (t, 2H, J=7.6 Hz), 2.38-2.28 (m, 2H), 2.29 (s, 3H), 2.25 (s, 3H), 1.58 (s, 9H)

Example 86

1-(3-(1-tert-butyl-5-(4-fluorophenyl)-1H-pyrazol-3-yl)propyl)-4-(2,3-dimethylphenyl)piperazine (Compound 86)

133 mg (75%) of target compound was obtained by using a method same as in Example 1 by using 3-(1-tert-butyl-5-(4-fluorophenyl)-1H-pyrazol-3-yl)propanal (100 mg, 0.365 mmol), 1-(2,3-dimethylphenyl)piperazine (69 mg, 0.365 mmol), DIPEA (0.1 mL, 0.548 mmol) and NaBH(OAc)$_3$ (232 mg, 1.095 mmol).

$^1$H NMR (400 MHz, MeOH-d$_4$) δ 7.47-7.38 (m, 2H), 7.23-7.17 (m, 2H), 7.09-7.03 (m, 1H), 6.99-6.93 (m, 2H), 6.23 (s, 1H), 3.73-3.62 (m, 2H), 3.42-3.18 (m, 6H), 3.18-3.06 (m, 2H), 2.84 (t, 2H, J=7.4 Hz), 2.27 (s, 3H), 2.26 (s, 3H), 2.24-2.13 (m, 2H), 1.49 (s, 9H)

Example 87

1-(3-(1-tert-butyl-5-(4-fluorophenyl)-1H-pyrazol-3-yl)propyl)-4-(4-methoxyphenyl)piperazine (Compound 87)

102 mg (58%) of target compound was obtained by using a method same as in Example 1 by using 3-(1-tert-butyl-5-(4-fluorophenyl)-1H-pyrazol-3-yl)propanal (100 mg, 0.365 mmol), 1-(4-methoxyphenyl)piperazine (71 mg, 0.365 mmol), DIPEA (0.1 mL, 0.548 mmol) and NaBH(OAc)$_3$ (232 mg, 1.095 mmol).

$^1$H NMR (400 MHz, MeOH-d$_4$) δ 7.60-7.49 (m, 2H), 7.41-7.33 (m, 2H), 7.30-7.21 (m, 2H), 7.07-6.98 (m, 2H), 6.56 (s, 1H), 3.81 (s, 1H), 3.80-3.69 (m, 8H), 3.47-3.39 (m, 2H) 3.00 (t, 2H, J=7.5 Hz), 2.39-2.23 (m, 2H), 1.58 (s, 9H)

Example 88

4-(3-(1-tert-butyl-5-(4-fluorophenyl)-1H-pyrazol-3-yl)propyl)-2-methyl-1-m-tolylpiperazine (Compound 88)

143 mg (81%) of target compound was obtained by using a method same as in Example 1 by using 3-(1-tert-butyl-5-(4-fluorophenyl)-1H-pyrazol-3-yl)propanal (100 mg, 0.365 mmol), 2-methyl-1-m-tolylpiperazine (69 mg, 0.365 mmol), DIPEA (0.1 mL, 0.548 mmol) and NaBH(OAc)$_3$ (232 mg, 1.095 mmol).

$^1$H NMR (400 MHz, MeOH-d$_4$) δ 7.56-7.47 (m, 3H), 7.47-7.38 (m, 2H), 7.35-7.29 (m, 1H), 7.29-7.20 (m, 2H), 6.45 (s, 1H), 4.36 (bs, 1H), 4.13-3.93 (m, 2H), 3.93-3.74 (m, 3H), 3.69-3.56 (m, 1H), 3.51-3.40 (m, 2H), 2.96 (t, 2H, J=7.5 Hz), 2.43 (s, 3H), 2.38-2.23 (m, 2H), 1.55 (s, 9H), 1.19 (d, 3H, J=6.5 Hz)

Example 89

1-(3-(1-tert-butyl-5-(4-fluorophenyl)-1H-pyrazol-3-yl)propyl)-4-(3,4-dichlorophenyl)piperazine (Compound 89)

162 mg (85%) of target compound was obtained by using a method same as in Example 1 by using 3-(1-tert-butyl-5-(4-fluorophenyl)-1H-pyrazol-3-yl)propanal (100 mg, 0.365 mmol), 1-(3,4-dichlorophenyl)piperazine (84 mg, 0.365 mmol), DIPEA (0.1 mL, 0.548 mmol) and NaBH(OAc)$_3$ (232 mg, 1.095 mmol).

$^1$H NMR (400 MHz, MeOH-d$_4$) δ 7.51-7.43 (m, 2H), 7.39 (d, 1H, J=8.9 Hz), 7.26-7.14 (m, 3H), 7.00-6.91 (m, 1H), 6.38 (s, 1H), 3.92-3.81 (m, 2H), 3.77-3.68 (m, 2H), 3.38-3.31 (m, 2H), 3.29-3.12 (m, 4H), 2.90 (t, 2H, J=7.5 Hz), 2.40-2.20 (m, 2H), 1.53 (s, 9H)

Example 90

1-(3-(1-tert-butyl-5-(4-fluorophenyl)-1H-pyrazol-3-yl)propyl)-4-(bis(4-fluorophenyl)methyl)piperazine (Compound 90)

172 mg (81%) of target compound was obtained by using a method same as in Example 1 by using 3-(1-tert-butyl-5-(4-fluorophenyl)-1H-pyrazol-3-yl)propanal (100 mg, 0.365 mmol), 1-(bis(4-fluorophenyl)methyl)piperazine (105 mg, 0.365 mmol), DIPEA (0.1 mL, 0.548 mmol) and NaBH(OAc)$_3$ (232 mg, 1.095 mmol).

$^1$H NMR (400 MHz, MeOH-d$_4$) δ 7.92-7.70 (m, 4H), 7.51-7.40 (m, 2H), 2.27-7.10 (m, 6H), 6.40 (s, 1H), 5.42 (bs, 1H), 3.83-3.61 (m, 4H), 3.49-3.22 (m, 6H), 2.90 (t, 2H, J=7.5 Hz), 2.30-2.12 (m, 2H), 1.52 (s, 9H)

Example 91

1-(3-(5-(4-fluorophenyl)-1-phenyl-1H-pyrazol-3-yl)propyl)-4-phenylpiperazine (Compound 91)

49 mg (62%) of target compound was obtained by using a method same as in Example 1 by using 3-(5-(4-fluorophenyl)-1-phenyl-1H-pyrazol-3-yl)-propanal (55 mg, 0.187 mmol), 1-phenylpiperazine (0.026 mL, 0.170 mmol), DIPEA (0.030 mL, 0.170 mmol) and NaBH(OAc)$_3$ (108 mg, 0.510 mmol).

$^1$H NMR (400 MHz, MeOH-d$_4$) δ 7.48-7.40 (m, 2H), 7.37-7.28 (m, 6H), 7.12-7.04 (m, 3H), 7.04-7.01 (m, 1H), 7.01-6.96 (m, 2H), 6.68 (s, 1H), 3.88-3.63 (m, 4H), 3.44-3.30 (m, 4H), 3.28-3.08 (m, 2H), 2.93 (t, 2H, J=7.1 hz), 2.31 (t, 2H, J=7.6 Hz)

Example 92

1-(2-fluorophenyl)-4-(3-(5-(4-fluorophenyl)-1-phenyl-1H-pyrazol-3-yl)propyl)piperazine (Compound 92)

57 mg (70%) of target compound was obtained by using a method same as in Example 1 by using 3-(5-(4-fluorophenyl)-1-phenyl-1H-pyrazol-3-yl)-propanal (55 mg, 0.187 mmol), 1-(2-fluorophenyl)piperazine (0.027 mL, 0.170 mmol), DIPEA (0.030 mL, 0.170 mmol) and NaBH(OAc)$_3$ (108 mg, 0.510 mmol).

$^1$H NMR (400 MHz, MeOH-d$_4$) δ 7.51-7.48 (m, 3H), 7.46-7.42 (m, 2H), 7.40-7.34 (m, 2H), 7.13-7.08 (m, 6H), 6.85 (s, 1H), 3.83-3.68 (m, 2H), 3.64-3.52 (m, 2H), 3.45-3.33 (m, 4H), 3.27-3.13 (m, 2H), 3.00 (t, 2H, J=9.7 Hz), 2.43-2.28 (m, 2H)

Example 93

1-(4-chlorophenyl)-4-(3-(5-(4-fluorophenyl)-1-phenyl-1H-pyrazol-3-yl)propyl)piperazine (Compound 93)

100 mg (72%) of target compound was obtained by using a method same as in Example 1 by using 3-(5-(4-fluorophenyl)-1-phenyl-1H-pyrazol-3-yl)-propanal (80 mg, 0.272 mmol), 1-(4-chlorophenyl)piperazine (73 mg, 0.272 mmol), DIPEA (0.071 mL, 0.408 mmol) and NaBH(OAc)$_3$ (173 mg, 0.816 mmol).

$^1$H NMR (400 MHz, MeOH-d$_4$) δ 7.53-7.44 (m, 3H), 7.41-7.34 (m, 2H), 3.34-2.98 (m, 2H), 7.27 (d, 2H, J=8.8 Hz), 7.13-7.05 (m, 2H), 7.01 (d, 2H, J=8.9 Hz), 6.76 (s, 1H), 3.91-3.55 (m, 4H), 3.42-3.23 (m, 4H), 3.19-3.01 (m, 2H), 2.96 (t, 2H, J=6.6 Hz), 2.39-2.23 (m, 2H)

Example 94

1-(3-(5-(4-fluorophenyl)-1-phenyl-1H-pyrazol-3-yl) propyl)-4-(2,4-dimethylphenyl)piperazine (Compound 94)

96 mg (70%) of target compound was obtained by using a method same as in Example 1 by using 3-(5-(4-fluorophenyl)-1-phenyl-1H-pyrazol-3-yl)-propanal (80 mg, 0.272 mmol), 1-(2,4-dimethylphenyl)piperazine (52 mg, 0.272 mmol), DIPEA (0.071 mL, 0.408 mmol) and NaBH(OAc)$_3$ (173 mg, 0.816 mmol).

$^1$H NMR (400 MHz, MeOH-d$_4$) δ 7.51-7.13 (m, 3H), 7.38-7.24 (m, 4H), 7.12-7.03 (m, 2H), 7.03-6.93 (m, 2H), 6.91 (d, 1H, J=8.1 Hz), 6.66 (s, 1H), 3.83-3.57 (m, 2H), 3.43-3.12 (m, 6H), 3.12-2.98 (m, 2H), 2.94 (t, 2H, J=6.5 Hz), 2.38-2.23 (m, 2H), 2.28 (s, 3H), 2.25 (s, 3H)

Example 95

1-(3-(5-(4-fluorophenyl)-1-phenyl-1H-pyrazol-3-yl) propyl)-4-(3,4-dimethylphenyl)piperazine (Compound 95)

60 mg (71%) of target compound was obtained by using a method same as in Example 1 by using 3-(5-(4-fluorophenyl)-1-phenyl-1H-pyrazol-3-yl)-propanal (50 mg, 0.170 mmol), 1-(3,4-dimethylphenyl)piperazine (32 mg, 0.170 mmol), DIPEA (0.030 mL, 0.170 mmol) and NaBH(OAc)$_3$ (108 mg, 0.510 mmol).

$^1$H NMR (400 MHz, MeOH-d$_4$) δ 7.50-7.44 (m, 3H), 7.41-7.34 (m, 2H), 7.34-7.28 (m, 3H), 7.27-7.20 (m, 2H), 7.13-7.03 (m, 2H), 6.78 (s, 1H), 3.98-3.70 (m, 8H), 3.52-3.40 (m, 2H), 2.98 (t, 2H, J=7.3 Hz), 2.41-2.32 (m, 2H), 2.32 (s, 3H), 2.23 (s, 3H)

Example 96

1-(3-(5-(4-fluorophenyl)-1-phenyl-1H-pyrazol-3-yl) propyl)-4-(2,3-dimethylphenyl)piperazine (Compound 96)

42 mg (50%) of target compound was obtained by using a method same as in Example 1 by using 3-(5-(4-fluorophenyl)-1-phenyl-1H-pyrazol-3-yl)-propanal (50 mg, 0.170 mmol), 1-(2,3-dimethylphenyl)piperazine (32 mg, 0.170 mmol), DIPEA (0.030 mL, 0.170 mmol) and NaBH(OAc)$_3$ (108 mg, 0.510 mmol).

$^1$H NMR (400 MHz, MeOH-d$_4$) δ 7.47-7.38 (m, 3H), 7.34-7.20 (m, 4H), 7.10-7.00 (m, 3H), 6.94 (d, 1H, J=7.3 Hz), 6.85 (d, 1H, J=7.8 Hz), 6.55 (s, 1H), 3.78-3.60 (m, 2H), 3.40-3.20 (m, 4H), 3.20-3.09 (m, 2H), 3.06-2.91 (m, 2H), 2.90 (t, 2H, J=6.7 Hz), 2.31-2.26 (m, 2H), 2.26 (s, 3H), 2.23 (s, 3H)

Example 97

1-(3-(5-(4-fluorophenyl)-1-phenyl-1H-pyrazol-3-yl) propyl)-4-(4-methoxyphenyl)piperazine (Compound 97)

80 mg (58%) of target compound was obtained by using a method same as in Example 1 by using 3-(5-(4-fluorophenyl)-1-phenyl-1H-pyrazol-3-yl)-propanal (80 mg, 0.272 mmol), 1-(4-methoxyphenyl)piperazine (72 mg, 0.272 mmol), DIPEA (0.071 mL, 0.408 mmol) and NaBH(OAc)$_3$ (173 mg, 0.816 mmol).

$^1$H NMR (400 MHz, MeOH-d$_4$) δ 7.50-7.40 (m, 5H), 7.40-7.34 (m, 2H), 7.34-7.26 (m, 2H), 7.12-7.00 (m, 4H), 6.75 (s, 1H), 3.98-3.59 (m, 8H), 3.82 (s, 3H), 3.52-3.38 (m, 2H), 3.02-2.88 (m, 2H), 2.42-2.27 (m, 2H)

Example 98

4-(3-(5-(4-fluorophenyl)-1-phenyl-1H-pyrazol-3-yl) propyl)-2-methyl-1-m-tolylpiperazine (Compound 98)

54 mg (65%) of target compound was obtained by using a method same as in Example 1 by using 3-(5-(4-fluorophenyl)-1-phenyl-1H-pyrazol-3-yl)-propanal (53 mg, 0.179 mmol), 2-methyl-1-m-tolylpiperazine (32 mg, 0.179 mmol), DIPEA (0.033 mL, 0.187 mmol) and NaBH(OAc)$_3$ (108 mg, 0.510 mmol).

$^1$H NMR (400 MHz, MeOH-d$_4$) δ 7.53-7.20 (m, 10H), 7.10-6.90 (m, 3H), 6.72 (s, 1H), 4.36 (bs, 1H), 4.14-3.74 (m, 7H), 3.74-3.60 (m, 2H), 3.54-3.38 (m, 3H), 3.22-2.86 (m, 4H), 2.42 (s, 3H), 2.40-2.20 (m, 2H), 1.26-0.98 (m, 3H)

Example 99

1-(3,4-dichlorophenyl)-4-(3-(5-(4-fluorophenyl)-1-phenyl-1H-pyrazol-3-yl)propyl)piperazine (Compound 99)

90 mg (61%) of target compound was obtained by using a method same as in Example 1 by using 3-(5-(4-fluorophenyl)-1-phenyl-1H-pyrazol-3-yl)-propanal (80 mg, 0.272 mmol), 1-(3,4-dichlorophenyl)piperazine (63 mg, 0.272 mmol), DIPEA (0.071 mL, 0.408 mmol) and NaBH(OAc)$_3$ (173 mg, 0.816 mmol).

$^1$H NMR (400 MHz, MeOH-d$_4$) δ 7.49-7.21 (m, 8H), 7.13 (s, 1H), 7.08 (t, 2H, J=8.2 Hz), 6.93 (d, 2H, J=8.9 Hz), 6.65 (s, 1H), 3.90-3.78 (m, 2H), 3.78-3.62 (m, 2H), 3.41-3.18 (m, 4H), 3.04 (t, 2H, J=11.99 Hz), 2.97-2.86 (m, 2H), 2.37-2.20 (m, 2H)

Example 100

1-(bis(4-fluorophenyl)methyl)-4-(3-(5-(4-fluorophenyl)-1-phenyl-1H-pyrazol-3-yl)propyl)piperazine (Compound 100)

113 mg (69%) of target compound was obtained by using a method same as in Example 1 by using 3-(5-(4-fluorophenyl)-1-phenyl-1H-pyrazol-3-yl)-propanal (80 mg, 0.272 mmol), 1-(bis(4-fluorophenyl)methyl)piperazine (78 mg, 0.272 mmol), DIPEA (0.071 mL, 0.408 mmol) and NaBH (OAc)$_3$ (173 mg, 0.816 mmol).

$^1$H NMR (400 MHz, MeOH-d$_4$) δ 7.90-7.66 (m, 4H), 7.49-7.39 (m, 3H), 7.33-7.21 (m, 4H), 7.21-7.10 (m, 4H), 7.06 (t,

2H, J=8.6 Hz), 6.58 (s, 1H), 5.26 (bs, 1H), 3.89-3.59 (m, 4H), 3.42-3.14 (m, 6H), 2.88 (t, 2H, J=6.6 Hz), 2.31-2.19 (m, 2H)

Example 101

1-(3-(1-tert-butyl-5-(thiophene-2-yl)-1H-pyrazol-3-yl)propyl)-4-phenylpiperazine (Compound 101)

81 mg (95%) of target compound was obtained by using a method same as in Example 1 by using 3-(1-tert-butyl-5-(thiophene-2-yl)-1H-pyrazol-3-yl)propanal (50 mg, 0.191 mmol), 1-phenylpiperazine (0.029 mL, 0.191 mmol), DIPEA (0.050 mL, 0.287 mmol) and NaBH(OAc)$_3$ (121 mg, 0.573 mmol).
$^1$H NMR (400 MHz, MeOH-d$_4$) δ 7.75 (d, 1H, J=4.9 Hz), 7.49-7.33 (m, 3H), 7.31 (d, 2H, J=7.9 Hz), 7.21-7.18 (m, 1H), 7.15 (t, 1H, J=7.2 Hz), 6.68 (s, 1H), 3.93-3.52 (m, 8H), 3.43-3.37 (m, 2H), 3.04-2.91 (m, 2H), 2.39-2.21 (m, 2H) 1.65 (s, 9H)

Example 102

1-(3-(1-tert-butyl-5-(thiophene-2-yl)-1H-pyrazol-3-yl)propyl)-4-(2-fluorophenyl)piperazine (Compound 102)

77 mg (73%) of target compound was obtained by using a method same as in Example 1 by using 3-(1-tert-butyl-5-(thiophene-2-yl)-1H-pyrazol-3-yl)propanal (50 mg, 0.191 mmol), 1-(2-fluorophenyl)piperazine (34 mg, 0.191 mmol), DIPEA (0.050 mL, 0.287 mmol) and NaBH(OAc)$_3$ (121 mg, 0.573 mmol).
$^1$H NMR (400 MHz, MeOH-d$_4$) δ 7.73 (d, 1H, J=5.0 Hz), 7.38-7.30 (m, 1H), 7.21-7.17 (m, 1H), 7.17-7.03 (m, 4H), 6.62 (s, 1H), 3.80-3.67 (m, 2H), 3.67-3.54 (m, 2H), 3.42-3.31 (m, 4H), 3.28-3.18 (m, 2H), 3.01-2.90 (m, 2H), 2.39-2.20 (m, 2H), 1.63 (s, 9H)

Example 103

1-(3-(1-tert-butyl-5-(thiophene-2-yl)-1H-pyrazol-3-yl)propyl)-4-(4-chlorophenyl)piperazine (Compound 103)

77 mg (73%) of target compound was obtained by using a method same as in Example 1 by using 3-(1-tert-butyl-5-(thiophene-2-yl)-1H-pyrazol-3-yl)propanal (50 mg, 0.191 mmol), 1-(4-chlorophenyl)piperazine (34 mg, 0.191 mmol), DIPEA (0.050 mL, 0.287 mmol) and NaBH(OAc)$_3$ (121 mg, 0.573 mmol).
$^1$H NMR (400 MHz, MeOH-d$_4$) δ 7.75 (d, 1H, J=5.0 Hz), 7.41-7.32 (m, 1H), 7.28 (d, 2H, J=8.4 Hz), 7.21-7.15 (m, 1H), 7.05 (d, 2H, J=8.6 Hz), 6.66 (s, 1H), 3.96-3.59 (m, 4H), 3.45-3.12 (m, 6H), 3.02-2.90 (m, 2H), 2.39-2.23 (m, 2H), 1.64 (s, 9H)

Example 104

1-(3-(1-tert-butyl-5-(thiophene-2-yl)-1H-pyrazol-3-yl)propyl)-4-(2,4-dimethylphenyl)piperazine (Compound 104)

79 mg (87%) of target compound was obtained by using a method same as in Example 1 by using 3-(1-tert-butyl-5-(thiophene-2-yl)-1H-pyrazol-3-yl)propanal (50 mg, 0.191 mmol), 1-(2,4-dimethylphenyl)piperazine (36 mg, 0.191 mmol), DIPEA (0.050 mL, 0.287 mmol) and NaBH(OAc)$_3$ (121 mg, 0.573 mmol).
$^1$H NMR (400 MHz, MeOH-d$_4$) δ 7.71 (d, 1H, J=5.0 Hz), 7.34-7.28 (m, 1H), 7.21-7.13 (m, 1H), 7.07-6.94 (m, 3H), 6.58 (s, 1H), 3.83-3.57 (m, 2H), 3.50-3.17 (m, 8H), 2.98-2.85 (m, 2H), 2.36-2.19 (m, 2H), 2.31 (s, 3H), 2.26 (s, 3H), 1.67 (s, 9H)

Example 105

1-(3-(1-tert-butyl-5-(thiophene-2-yl)-1H-pyrazol-3-yl)propyl)-4-(3,4-dimethylphenyl)piperazine (Compound 105)

79 mg (88%) of target compound was obtained by using a method same as in Example 1 by using 3-(1-tert-butyl-5-(thiophene-2-yl)-1H-pyrazol-3-yl) (50 mg, 0.191 mmol), 1-(3,4-dimethylphenyl)piperazine (36 mg, 0.191 mmol), DIPEA (0.050 mL, 0.287 mmol) and NaBH(OAc)$_3$ (121 mg, 0.573 mmol).
$^1$H NMR (400 MHz, MeOH-d$_4$) δ 7.73 (d, 1H, J=5.0 Hz), 7.38-7.29 (m, 2H), 7.29-7.23 (m, 2H), 7.21-7.16 (m, 1H), 6.63 (s, 1H), 4.00-3.88 (m, 4H), 3.88-3.71 (m, 4H), 3.50-3.39 (m, 2H), 3.03-2.91 (m, 2H), 2.38-2.21 (m, 2H), 2.23 (s, 3H), 2.28 (s, 3H), 1.63 (s, 9H)

Example 106

1-(3-(1-tert-butyl-5-(thiophene-2-yl)-1H-pyrazol-3-yl)propyl)-4-(2,3-dimethylphenyl)piperazine (Compound 106)

86 mg (96%) of target compound was obtained by using a method same as in Example 1 by using 3-(1-tert-butyl-5-(thiophene-2-yl)-1H-pyrazol-3-yl)propanal (50 mg, 0.191 mmol), 1-(2,3-dimethylphenyl)piperazine (36 mg, 0.191 mmol), DIPEA (0.050 mL, 0.287 mmol) and NaBH(OAc)$_3$ (121 mg, 0.573 mmol).
$^1$H NMR (400 MHz, MeOH-d$_4$) δ 7.73 (d, 1H, J=5.0 Hz), 7.39-7.30 (m, 1H), 7.21-7.14 (m, 1H), 7.11-7.02 (m, 1H), 7.02-6.92 (m, 2H), 6.64 (s, 1H), 3.80-3.59 (m, 2H), 3.49-3.31 (m, 4H), 3.28-3.12 (m, 4H), 3.00-3.88 (m, 2H), 2.38-2.23 (m, 2H), 2.27 (s, 6H), 1.64 (s, 9H)

Example 107

1-(3-(1-tert-butyl-5-(thiophene-2-yl)-1H-pyrazol-3-yl)propyl)-4-(4-methoxyphenyl)piperazine (Compound 107)

60 mg (66%) of target compound was obtained by using a method same as in Example 1 by using 3-(1-tert-butyl-5-(thiophene-2-yl)-1H-pyrazol-3-yl)propanal (50 mg, 0.191 mmol), 1-(4-methoxyphenyl)piperazine (40 mg, 0.191 mmol), DIPEA (0.050 mL, 0.287 mmol) and NaBH(OAc)$_3$ (121 mg, 0.573 mmol).
$^1$H NMR (400 MHz, MeOH-d$_4$) δ 7.78 (d, 1H, J=4.7 Hz), 7.57 (d, 2H, J=8.4 Hz), 7.38-7.28 (m, 1H), 7.21-7.13 (m, 1H), 7.07 (d, 2H, J=8.3 Hz), 6.23 (s, 1H), 4.02-3.91 (m, 4H), 3.91-3.82 (m, 4H), 3.83 (s, 3H), 3.50-3.39 (m, 2H), 3.02-2.90 (m, 2H), 2.40-2.23 (m, 2H), 1.63 (s, 9H)

Example 108

4-(3-(1-tert-butyl-5-(thiophene-2-yl)-1H-pyrazol-3-yl)propyl)-2-methyl-1-m-tolylpiperazine (Compound 108)

89 mg (99%) of target compound was obtained by using a method same as in Example 1 by using 3-(1-tert-butyl-5-(thiophene-2-yl)-1H-pyrazol-3-yl)propanal (50 mg, 0.191 mmol), 2-methyl-1-m-tolylpiperazine (36 mg, 0.191 mmol), DIPEA (0.050 mL, 0.287 mmol) and NaBH(OAc)$_3$ (121 mg, 0.573 mmol).

$^1$H NMR (400 MHz, MeOH-d$_4$) δ 7.69 (d, 1H, J=5.1 Hz), 7.68-7.62 (m, 1H), 7.61-7.53 (m, 1H), 7.51 (t, 1H, J=7.8 Hz), 7.41-7.34 (m, 1H), 7.31-7.23 (m, 1H), 7.18-7.11 (m, 1H), 6.54 (s, 1H), 4.59-4.43 (m, 1H), 4.31-4.17 (m, 1H), 4.11-4.00 (m, 1H), 4.00-3.86 (m, 3H), 3.80-3.69 (m, 1H), 3.48 (t, 2H, J=7.0 Hz), 2.99-2.88 (m, 2H), 2.45 (s, 3H), 2.39-2.23 (m, 2H), 1.60 (s, 9H), 1.23 (d, 3H, J=5.8 Hz)

Example 109

1-(3-(1-tert-butyl-5-(thiophene-2-yl)-1H-pyrazol-3-yl)propyl)-4-(3,4-dichlorophenyl)piperazine (Compound 109)

92 mg (94%) of target compound was obtained by using a method same as in Example 1 by using 3-(1-tert-butyl-5-(thiophene-2-yl)-1H-pyrazol-3-yl)propanal (50 mg, 0.191 mmol), 1-(3,4-dichlorophenyl)piperazine (44 mg, 0.191 mmol), DIPEA (0.050 mL, 0.287 mmol) and NaBH(OAc)$_3$ (121 mg, 0.573 mmol).

$^1$H NMR (400 MHz, MeOH-d$_4$) δ 7.78 (d, 1H, J=5.0 Hz), 7.43-7.36 (m, 2H), 7.23-7.18 (m, 2H), 7.01-6.92 (m, 1H), 6.75 (s, 1H), 3.97-3.80 (m, 2H), 3.80-3.67 (m, 2H), 3.40-3.18 (m, 6H), 3.08-2.93 (m, 2H), 2.39-2.21 (m, 2H), 1.67 (s, 9H)

Example 110

1-(3-(1-tert-butyl-5-(thiophene-2-yl)-1H-pyrazol-3-yl)propyl)-4-(bis(4-fluorophenyl)methyl)piperazine (Compound 110)

92 mg (84%) of target compound was obtained by using a method same as in Example 1 by using 3-(1-tert-butyl-5-(thiophene-2-yl)-1H-pyrazol-3-yl)propanal (50 mg, 0.191 mmol), 1-(bis(4-fluorophenyl)methyl)piperazine (55 mg, 0.191 mmol), DIPEA (0.050 mL, 0.287 mmol) and NaBH(OAc)$_3$ (121 mg, 0.573 mmol).

$^1$H NMR (400 MHz, MeOH-d$_4$) δ 8.07-7.88 (m, 4H), 7.66 (d, 1H, J=4.5 Hz), 7.32-7.21 (m, 4H), 7.16 (d, 1H, J=2.8 Hz), 7.08 (t, 1H, J=7.9 Hz), 6.15 (s, 1H), 3.80-3.56 (m, 5H), 3.43-3.29 (m, 4H), 3.29-3.11 (m, 2H), 2.55 (t, 2H, J=7.2 Hz), 2.10-1.91 (m, 2H), 1.39 (s, 9H)

Example 111

1-phenyl-4-(3-(1-phenyl-5-(thiophene-2-yl)-1H-pyrazol-3-yl)propyl)piperazine (Compound 111)

63 mg (96%) of target compound was obtained by using a method same as in Example 1 by using 3-(1-phenyl-5-(thiophene2-yl)-1H-pyrazol-3-yl)-propanal (40 mg, 0.142 mmol), 1-phenylpiperazine (0.021 mL, 0.142 mmol), DIPEA (0.040 mL, 0.213 mmol) and NaBH(OAc)$_3$ (90 mg, 0.426 mmol).

$^1$H NMR (400 MHz, MeOH-d$_4$) δ 7.68-7.52 (m, 6H), 7.44 (t, 2H, J=7.8 Hz), 7.37 (d, 2H, J=8.0 Hz), 7.21-7.13 (m, 2H), 7.08-7.01 (m, 1H), 6.99 (s, 1H), 3.99-3.55 (m, 8H), 3.49-3.99 (m, 2H), 2.99 (t, 2H, J=6.3 Hz), 2.43-2.29 (m, 2H)

Example 112

1-(2-fluorophenyl)-4-(3-(1-phenyl-5-(thiophene-2-yl)-1H-pyrazol-3-yl)propyl)piperazine (Compound 112)

62 mg (91%) of target compound was obtained by using a method same as in Example 1 by using 3-(1-phenyl-5-(thiophene-2-yl)-1H-pyrazol-3-yl)-propanal (40 mg, 0.142 mmol), 1-(2-fluorophenyl)piperazine (26 mg, 0.142 mmol), DIPEA (0.040 mL, 0.213 mmol) and NaBH(OAc)$_3$ (90 mg, 0.573 mmol).

$^1$H NMR (400 MHz, MeOH-d$_4$) δ 7.60-7.51 (m, 3H), 7.51-7.47 (m, 3H), 7.14-7.00 (m, 6H), 6.85 (s, 1H), 3.80-3.67 (m, 2H), 3.62-3.52 (m, 2H), 3.40-3.27 (m, 4H), 3.20-3.08 (m, 2H), 2.95 (t, 2H, J=6.1 Hz), 2.39-2.23 (m, 2H)

Example 113

1-(4-chlorophenyl)-4-(3-(1-phenyl-5-(thiophene-2-yl)-1H-pyrazol-3-yl)propyl)piperazine (Compound 113)

55 mg (78%) of target compound was obtained by using a method same as in Example 1 by using 3-(1-phenyl-5-(thiophene-2-yl)-1H-pyrazol-3-yl)-propanal (40 mg, 0.142 mmol), 1-(4-chlorophenyl)piperazine (38 mg, 0.142 mmol), DIPEA (0.040 mL, 0.213 mmol) and NaBH(OAc)$_3$ (90 mg, 0.573 mmol).

$^1$H NMR (400 MHz, MeOH-d$_4$) δ 7.66-7.52 (m, 2H), 7.29 (d, 2H, J=8.9 Hz), 7.21-7.17 (m, 1H), 7.09-7.00 (m, 3H), 6.99 (s, 1H), 3.92-3.64 (m, 4H), 3.42-3.13 (m, 6H), 2.98 (t, 2H, J=7.2 Hz), 2.42-2.26 (m, 2H)

Example 114

1-(2,4-dimethylphenyl)-4-(3-(1-phenyl-5-(thiophene-2-yl)-1H-pyrazol-3-yl)propyl)piperazine (Compound 114)

66 mg (95%) of target compound was obtained by using a method same as in Example 1 by using 3-(1-phenyl-5-(thiophene-2-yl)-1H-pyrazol-3-yl)-propanal (40 mg, 0.142 mmol), 1-(2,4-dimethylphenyl)piperazine (27 mg, 0.142 mmol), DIPEA (0.040 mL, 0.213 mmol) and NaBH(OAc)$_3$ (90 mg, 0.573 mmol).

$^1$H NMR (400 MHz, MeOH-d$_4$) δ 7.70-7.58 (m, 5H), 7.58-7.51 (m, 1H), 7.27-7.19 (m, 1H), 7.17-7.10 (m, 1H), 7.10-7.01 (m, 3H), 7.01 (s, 1H), 3.90-3.68 (m, 2H), 3.65-3.51 (m, 2H), 3.48-3.36 (m, 6H), 3.08-2.93 (m, 2H), 2.41-2.30 (m, 2H), 2.38 (s, 3H), 2.28 (s, 3H)

Example 115

1-(3,4-dimethylphenyl)-4-(3-(1-phenyl-5-(thiophene-2-yl)-1H-pyrazol-3-yl)propyl)piperazine (Compound 115)

54 mg (77%) of target compound was obtained by using a method same as in Example 1 by using 3-(1-phenyl-5-(thiophene-2-yl)-1H-pyrazol-3-yl)-propanal (40 mg, 0.142 mmol), 1-(3,4-dimethylphenyl)piperazine (27 mg, 0.142 mmol), DIPEA (0.040 mL, 0.213 mmol) and NaBH(OAc)$_3$ (90 mg, 0.573 mmol).

$^1$H NMR (400 MHz, MeOH-d$_4$) δ 7.60-7.52 (m, 3H), 7.52-7.37 (m, 3H), 7.28 (s, 1H), 7.26-7.13 (m, 2H), 7.06 (d, 1H, J=3.1 Hz), 7.02 (d, 1H, J=3.7 Hz), 6.83 (s, 1H), 3.92-3.70 (m, 8H), 3.51-3.40 (m, 2H), 3.00-3.89 (m, 2H), 3.39-3.29 (m, 2H), 2.31 (s, 3H), 2.27 (s, 3H)

Example 116

1-(2,3-dimethylphenyl)-4-(3-(1-phenyl-5-(thiophene-2-yl)-1H-pyrazol-3-yl)propyl)piperazine (Compound 116)

50 mg (71%) of target compound was obtained by using a method same as in Example 1 by using 3-(1-phenyl-5-(thiophene-2-yl)-1H-pyrazol-3-yl)-propanal (40 mg, 0.142 mmol), 1-(2,3-dimethylphenyl)piperazine (27 mg, 0.142 mmol), DIPEA (0.040 mL, 0.213 mmol) and NaBH(OAc)$_3$ (90 mg, 0.573 mmol).

$^1$H NMR (400 MHz, MeOH-d$_4$) δ 7.60-7.52 (m, 3H), 7.52-7.43 (m, 3H), 7.10-7.00 (m, 3H), 6.96 (d, 1H, J=7.4 Hz), 6.90 (d, 1H, J=7.8 Hz), 6.79 (s, 1H), 3.80-3.63 (m, 2H), 3.46-3.37 (m, 4H), 3.30-3.18 (m, 2H), 3.18-3.03 (m, 2H), 2.99-2.90 (m, 2H), 2.38-2.30 (m, 2H), 2.26 (s, 3H), 2.25 (s, 3H)

Example 117

1-(4-methoxyphenyl)-4-(3-(1-phenyl-5-(thiophene-2-yl)-1H-pyrazol-3-yl)propyl)piperazine (Compound 117)

53 mg (76%) of target compound was obtained by using a method same as in Example 1 by using 3-(1-phenyl-5-(thiophene-2-yl)-1H-pyrazol-3-yl)-propanal (40 mg, 0.142 mmol), 1-(4-methoxyphenyl)piperazine (27 mg, 0.142 mmol), DIPEA (0.040 mL, 0.213 mmol) and NaBH(OAc)$_3$ (90 mg, 0.573 mmol).

$^1$H NMR (400 MHz, MeOH-d$_4$) δ 7.59-7.51 (m, 3H), 7.51-7.42 (m, 3H), 7.39 (d, 2H, J=8.7 Hz), 7.04-6.97 (m, 3H), 6.77 (s, 1H), 3.81 (s, 3H), 3.80-3.60 (m, 8H), 3.48-3.39 (m, 2H), 2.98-2.88 (m, 2H), 2.40-2.24 (m, 2H)

Example 118

2-methyl-4-(3-(1-phenyl-5-(thiophene-2-yl)-1H-pyrazol-3-yl)propyl)-1-m-tolylpiperazine (Compound 118)

55 mg (79%) of target compound was obtained by using a method same as in Example 1 by using 3-(1-phenyl-5-(thiophene-2-yl)-1H-pyrazol-3-yl)-propanal (40 mg, 0.142 mmol), 2-methyl-1-m-tolylpiperazine (27 mg, 0.142 mmol), DIPEA (0.040 mL, 0.213 mmol) and NaBH(OAc)$_3$ (90 mg, 0.573 mmol).

$^1$H NMR (400 MHz, MeOH-d$_4$) δ 7.54 (s, 1H), 7.50-7.31 (m, 8H), 7.30-7.25 (m, 1H), 6.97-6.90 (m, 1H), 6.90-6.83 (m, 1H), 6.72 (s, 1H), 4.46-7.30 (m, 1H), 4.20-4.08 (m, 1H), 4.01-3.91 (m, 1H), 3.91-3.76 (m, 3H), 3.72-3.60 (m, 2H), 3.36 (t, 2H, J=6.8 Hz), 2.90-2.78 (m, 2H), 2.32 (s, 3H), 2.30-2.20 (m, 2H), 1.10 (d, 3H, J=4.9 Hz)

Example 119

1-(3,4-dichlorophenyl)-4-(3-(1-phenyl-5-(thiophene-2-yl)-1H-pyrazol-3-yl)propyl)piperazine (Compound 119)

51 mg (68%) of target compound was obtained by using a method same as in Example 1 by using 3-(1-phenyl-5-(thiophene-2-yl)-1H-pyrazol-3-yl)-propanal (40 mg, 0.142 mmol), 1-(3,4-dichlorophenyl)piperazine (33 mg, 0.142 mmol), DIPEA (0.040 mL, 0.213 mmol) and NaBH(OAc)$_3$ (90 mg, 0.573 mmol).

$^1$H NMR (400 MHz, MeOH-d$_4$) δ 7.64-7.55 (m, 5H), 7.55 (d, 1H, J=4.9 Hz), 7.38 (d, 1H, J=8.8 Hz), 7.17 (s, 1H), 7.08-7.02 (m, 1H), 6.95 (s, 1H), 3.93-3.80 (m, 2H), 3.80-3.68 (m, 2H), 3.40-3.22 (m, 4H), 3.20-3.08 (m, 2H), 3.01-2.90 (m, 2H), 2.40-2.27 (m, 2H)

Example 120

1-(bis(4-fluorophenyl)methyl)-4-(3-(1-phenyl-5-(thiophene-2-yl)-1H-pyrazol-3-yl)propyl)piperazine (Compound 120)

65 mg (78%) of target compound was obtained by using a method same as in Example 1 by using 3-(1-phenyl-5-(thiophene-2-yl)-1H-pyrazol-3-yl)-propanal (40 mg, 0.142 mmol), 1-(bis(4-fluorophenyl)methyl)piperazine (41 mg, 0.142 mmol), DIPEA (0.040 mL, 0.213 mmol) and NaBH(OAc)$_3$ (90 mg, 0.573 mmol).

$^1$H NMR (400 MHz, MeOH-d$_4$) δ 7.97-7.75 (m, 4H), 7.59-7.49 (m, 3H), 7.49-7.34 (m, 3H), 7.27-7.10 (m, 4H), 7.01-6.91 (m, 2H), 6.70 (s, 1H), 5.52 (bs, 1H), 3.89-3.68 (m, 4H), 3.52-3.32 (m, 6H), 2.98-2.78 (m, 2H), 2.31-1.13 (m, 2H)

Example 121

1-phenyl-4-(3-(1-phenyl-3-methyl-1H-pyrazol-5-yl)propyl)piperazine (Compound 121)

60 mg (81%) of target compound was obtained by using a method same as in Example 1 by using 3-(1-phenyl-3-methyl-1H-pyrazol-5-yl)propanal (44 mg, 0.206 mmol), 1-phenylpiperazine (0.031 mL, 0.206 mmol), DIPEA (0.054 mL, 0.310 mmol) and NaBH(OAc)$_3$ (131 mg, 0.621 mmol).

$^1$H NMR (300 MHz, MeOH-d$_4$) δ 7.57-7.42 (m, 5H), 7.26-7.21 (m, 2H), 6.96 (d, 2H, J=7.9 Hz), 6.85 (t, 1H, J=7.3 Hz), 6.17 (s, 1H), 3.17-3.14 (m, 4H), 2.71 (t, 2H, J=7.6 Hz), 2.64-2.60 (m, 4H), 2.47-2.42 (m, 2H), 2.28 (s, 3H), 1.86-1.76 (m, 2H)

Example 122

1-(2-fluorophenyl)-4-(3-(1-phenyl-3-methyl-1H-pyrazol-5-yl)propyl)piperazine (Compound 122)

85 mg (83%) of target compound was obtained by using a method same as in Example 1 by using 3-(1-phenyl-3-methyl-1H-pyrazol-5-yl)propanal (58 mg, 0.268 mmol), 1-(2-fluorophenyl)piperazine (52 mg, 0.289 mmol), DIPEA (0.070 mL, 0.403 mmol) and NaBH(OAc)$_3$ (171 mg, 0.805 mmol).

$^1$H NMR (300 MHz, MeOH-d$_4$) δ 7.55-7.42 (m, 5H), 7.07-6.99 (m, 4H), 6.17 (s, 1H), 3.09-3.06 (m, 4H), 2.74-2.68 (m, 2H), 2.66-2.63 (m, 4H), 2.49-2.44 (m, 2H), 2.27 (s, 3H), 1.86-1.76 (m, 2H)

Example 123

1-phenyl-4-(3-(1-phenyl-3-ethyl-1H-pyrazol-5-yl)propyl)piperazine (Compound 123)

41 mg (80%) of target compound was obtained by using a method same as in Example 1 by using 3-(1-phenyl-3-ethyl-1H-pyrazol-5-yl)propanal (31 mg, 0.138 mmol), 1-phenylpiperazine (0.021 mL, 0.138 mmol), DIPEA (0.036 mL, 0.206 mmol) and NaBH(OAc)$_3$ (88 mg, 0.414 mmol).

$^1$H NMR (300 MHz, MeOH-d$_4$) δ 7.58-7.43 (m, 5H), 7.27-7.21 (m, 2H), 6.98-6.95 (m, 2H), 6.88-6.83 (m, 1H), 6.21 (s, 1H), 3.18-3.15 (m, 4H), 2.74-2.62 (m, 8H), 2.50-2.45 (m, 2H), 1.88-1.78 (m, 2H), 1.28 (t, 3H, J=7.6 Hz)

Example 124

1-(2-fluorophenyl)-4-(3-(1-phenyl-3-ethyl-1H-pyrazol-5-yl)propyl)piperazine (Compound 124)

53 mg (98%) of target compound was obtained by using a method same as in Example 1 by using 3-(1-phenyl-3-ethyl-1H-pyrazol-5-yl)propanal (31 mg, 0.138 mmol), 1-(2-fluorophenyl)piperazine (28 mg, 0.154 mmol), DIPEA (0.036 mL, 0.206 mmol) and NaBH(OAc)$_3$ (89 mg, 0.418 mmol).

$^1$H NMR (300 MHz, MeOH-d$_4$) δ 7.58-7.44 (m, 5H), 7.10-6.94 (m, 4H), 6.21 (s, 1H), 3.09-3.06 (m, 4H), 2.74-2.62 (m, 8H), 2.49-2.44 (m, 2H), 1.86-1.76 (m, 2H), 1.28 (t, 3H, J=7.6 Hz)

Example 125

1-(3-(1-tert-butyl-5-propyl-1H-pyrazol-3-yl)propyl)-4-phenylpiperazine (Compound 125)

90 mg (98%) of target compound was obtained by using a method same as in Example 1 by using 3-(1-tert-butyl-5-propyl-1H-pyrazol-3-yl)propanal (50 mg, 0.225 mmol), 1-phenylpiperazine (0.034 mL, 0.225 mmol), DIPEA (0.060 mL, 0338 mmol) and NaBH(OAc)$_3$ (143 mg, 0.675 mmol).

$^1$H NMR (400 MHz, MeOH-d$_4$) δ 7.50-7.40 (m, 2H), 7.40-7.32 (m, 2H), 7.21 (t, 1H, J=7.2 Hz), 6.74 (s, 1H), 3.99-3.50 (m, 10H), 3.43-3.31 (m, 2H), 3.06-3.91 (m, 4H), 2.38-2.24 (m, 2H), 1.91-1.78 (m, 2H), 1.83 (s, 9H), 1.18 (t, 3H, J=7.0 Hz)

Example 126

1-(3-(1-tert-butyl-5-propyl-1H-pyrazol-3-yl)propyl)-4-(2-fluorophenyl)piperazine (Compound 126)

93 mg (97%) of target compound was obtained by using a method same as in Example 1 by using 3-(1-tert-butyl-5-propyl-1H-pyrazol-3-yl)propanal (50 mg, 0.225 mmol), 1-(2-fluorophenyl)piperazine (41 mg, 0.225 mmol), DIPEA (0.060 mL, 0.338 mmol) and NaBH(OAc)$_3$ (143 mg, 0.675 mmol).

$^1$H NMR (400 MHz, MeOH-d$_4$) δ 7.18-7.01 (m, 4H), 6.74 (s, 1H), 3.80-3.66 (m, 2H), 3.66-3.53 (m, 2H), 3.42-3.20 (m, 6H), 3.06-2.89 (m, 4H), 2.38-2.21 (m, 2H), 1.92-1.77 (m, 2H), 1.83 (s, 9H), 0.95 (t, 3H, J=7.4 Hz)

Example 127

1-(3-(1-tert-butyl-5-propyl-1H-pyrazol-3-yl)propyl)-4-(4-chlorophenyl)piperazine (Compound 127)

62 mg (63%) of target compound was obtained by using a method same as in Example 1 by using 3-(1-tert-butyl-5-propyl-1H-pyrazol-3-yl)propanal (50 mg, 0.225 mmol), 1-(4-chlorophenyl)piperazine (0.034 mg, 0.225 mmol), DIPEA (0.060 mL, 0338 mmol) and NaBH(OAc)$_3$ (143 mg, 0.675 mmol).

$^1$H NMR (400 MHz, MeOH-d$_4$) δ 7.29 (d, 2H, J=7.5 Hz), 7.07 (d, 2H, J=7.7 Hz), 6.74 (s, 1H), 3.97-3.58 (m, 4H), 3.48-3.18 (m, 6H), 3.09-2.90 (m, 4H), 2.39-2.21 (m, 2H), 1.93-1.74 (m, 2H), 1.83 (s, 9H), 1.13-1.02 (m, 3H)

Example 128

1-(3-(1-tert-butyl-5-propyl-1H-pyrazol-3-yl)propyl)-4-(2,4-dimethylphenyl)piperazine (Compound 128)

96 mg (98%) of target compound was obtained by using a method same as in Example 1 by using 3-(1-tert-butyl-5-propyl-1H-pyrazol-3-yl)propanal (50 mg, 0.225 mmol), 1-(2,4-dimethylphenyl)piperazine (43 mg, 0.225 mmol), DIPEA (0.060 mL, 0338 mmol) and NaBH(OAc)$_3$ (143 mg, 0.675 mmol).

$^1$H NMR (400 MHz, MeOH-d$_4$) δ 7.23-7.13 (m, 1H), 7.13-7.02 (m, 2H), 6.75 (s, 1H), 3.93-3.64 (m, 2H), 3.64-3.40 (m, 6H), 3.40-3.30 (m, 2H), 3.08-3.90 (m, 4H), 2.39 (s, 3H), 2.38-2.21 (m, 2H), 2.28 (s, 3H), 1.94-1.72 (m, 2H), 1.83 (s, 9H), 1.20-1.06 (m, 3H)

Example 129

1-(3-(1-tert-butyl-5-propyl-1H-pyrazol-3-yl)propyl)-4-(3,4-dimethylphenyl)piperazine (Compound 129)

95 mg (98%) of target compound was obtained by using a method same as in Example 1 by using 3-(1-tert-butyl-5-propyl-1H-pyrazol-3-yl)propanal (50 mg, 0.225 mmol), 1-(3,4-dimethylphenyl)piperazine (43 mg, 0.225 mmol), DIPEA (0.060 mL, 0338 mmol) and NaBH(OAc)$_3$ (143 mg, 0.675 mmol).

$^1$H NMR (400 MHz, MeOH-d$_4$) δ 7.40 (s, 1H), 7.38-7.23 (m, 2H), 6.75 (s, 1H), 4.06-3.91 (m, 4H), 3.91-3.70 (m, 4H), 3.50-3.37 (m, 2H), 3.10-2.94 (m, 4H), 2.40-2.29 (m, 2H), 2.33 (s, 3H), 2.29 (s, 3H), 1.94-1.78 (m, 2H), 1.83 (s, 9H), 1.17-1.04 (m, 3H)

Example 130

1-(3-(1-tert-butyl-5-propyl-1H-pyrazol-3-yl)propyl)-4-(2,3-dimethylphenyl)piperazine (Compound 130)

92 mg (94%) of target compound was obtained by using a method same as in Example 1 by using 3-(1-tert-butyl-5-propyl-1H-pyrazol-3-yl)propanal (50 mg, 0.225 mmol), 1-(2,3-dimethylphenyl)piperazine (43 mg, 0.225 mmol), DIPEA (0.060 mL, 0338 mmol) and NaBH(OAc)$_3$ (143 mg, 0.675 mmol).

$^1$H NMR (400 MHz, MeOH-d$_4$) δ 7.14-7.04 (m, 1H), 7.04-6.92 (m, 2H), 6.74 (s, 1H), 3.80-3.61 (m, 2H), 3.50-3.30 (m, 4H), 3.29-3.19 (m, 4H), 3.03-2.90 (m, 4H), 2.38-2.21 (m, 8H), 1.88-1.74 (m, 11H), 1.16-1.03 (m, 3H)

Example 131

1-(3-(1-tert-butyl-5-propyl-1H-pyrazol-3-yl)propyl)-4-(4-methoxyphenyl)piperazine (Compound 131)

70 mg (71%) of target compound was obtained by using a method same as in Example 1 by using 3-(1-tert-butyl-5-propyl-1H-pyrazol-3-yl)propanal (50 mg, 0.225 mmol), 1-(4-methoxyphenyl)piperazine (44 mg, 0.225 mmol), DIPEA (0.060 mL, 0338 mmol) and NaBH(OAc)$_3$ (143 mg, 0.675 mmol).

$^1$H NMR (400 MHz, MeOH-d$_4$) δ 7.55 (d, 2H, J=8.5 Hz), 7.07 (d, 2H, J=8.3 Hz), 6.74 (s, 1H), 4.01-3.90 (m, 4H), 3.90-3.79 (m, 4H), 3.83 (s, 3H), 3.47-3.36 (m, 2H), 3.06-2.91 (m, 4H), 2.40-2.23 (m, 2H), 1.90-1.73 (m, 2H), 1.83 (s, 9H), 1.12-1.03 (m, 3H)

Example 132

4-(3-(1-tert-butyl-5-propyl-1H-pyrazol-3-yl)propyl)-2-methyl-1-m-tolylpiperazine (Compound 132)

93 mg (95%) of target compound was obtained by using a method same as in Example 1 by using 3-(1-tert-butyl-5-propyl-1H-pyrazol-3-yl)propanal (50 mg, 0.225 mmol), 2-methyl-1-m-tolylpiperazine (43 mg, 0.225 mmol), DIPEA (0.060 mL, 0338 mmol) and NaBH(OAc)$_3$ (143 mg, 0.675 mmol).

$^1$H NMR (400 MHz, MeOH-d$_4$) δ 7.68-7.43 (m, 3H), 7.41-7.30 (m, 1H), 6.74 (s, 1H), 4.50 (bs, 1H), 4.30-4.16 (m, 1H), 4.08-3.98 (m, 1H), 3.98-3.82 (m, 3H), 3.79-3.69 (m, 1H), 3.52-3.40 (m, 3H), 3.09-2.93 (m, 4H), 2.45 (s, 3H), 2.40-2.27 (m, 2H), 1.90-1.77 (m, 2H), 1.83 (s, 9H), 1.22 (d, 3H, J=16.1 Hz), 1.11 (t, 3H, J=7.0 Hz)

Example 133

1-(3-(1-tert-butyl-5-propyl-1H-pyrazol-3-yl)propyl)-4-(3,4-dichlorophenyl)piperazine (Compound 133)

103 mg (97%) of target compound was obtained by using a method same as in Example 1 by using 3-(1-tert-butyl-5-propyl-1H-pyrazol-3-yl)propanal (50 mg, 0.225 mmol), 1-(3,4-dichlorophenyl)piperazine (52 mg, 0.225 mmol), DIPEA (0.060 mL, 0338 mmol) and NaBH(OAc)$_3$ (143 mg, 0.675 mmol).

$^1$H NMR (400 MHz, MeOH-d$_4$) δ 7.40 (d, 1H, J=8.6 Hz), 7.22 (s, 1H), 7.00 (d, 1H, J=8.2 Hz), 6.75 (s, 1H), 3.98-3.82 (m, 2H), 3.79-3.66 (m, 2H), 3.40-3.20 (m, 6H), 3.08-2.98 (m, 4H), 2.39-2.22 (m, 2H), 1.90-1.76 (m, 2H), 1.84 (s, 9H), 1.20 (t, 3H, J=7.0 Hz)

Example 134

1-(3-(1-tert-butyl-5-propyl-1H-pyrazol-3-yl)propyl)-4-(bis(4-fluorophenyl)methyl)piperazine (Compound 134)

107 mg (90%) of target compound was obtained by using a method same as in Example 1 by using 3-(1-tert-butyl-5-propyl-1H-pyrazol-3-yl)propanal (50 mg, 0.225 mmol), 1-(bis(4-fluorophenyl)methyl)piperazine (65 mg, 0.225 mmol), DIPEA (0.060 mL, 0338 mmol) and NaBH(OAc)$_3$ (143 mg, 0.675 mmol).

$^1$H NMR (400 MHz, MeOH-d$_4$) δ 8.02-7.80 (m, 4H), 7.30-7.17 (m, 4H), 6.71 (s, 1H), 5.65 (bs, 1H), 3.93-3.76 (m, 4H), 3.64-3.49 (m, 4H), 3.45-3.34 (m, 2H), 3.05-2.90 (m, 4H), 2.36-2.19 (m, 2H), 1.90-1.74 (m, 2H), 1.82 (s, 9H), 1.11 (t, 3H, J=6.4 Hz)

Example 135

1-(3-(1-tert-butyl-3-propyl-1H-pyrazol-5-yl)propyl)-4-phenylpiperazine (Compound 135)

132 mg (73%) of target compound was obtained by using a method same as in Example 1 by using 3-(1-tert-butyl-3-propyl-1H-pyrazol-5-yl)propanal (100 mg, 0.450 mmol), 1-phenylpiperazine (0.067 mL, 0.450 mmol), DIPEA (0.118 mL, 0.675 mmol) and NaBH(OAc)$_3$ (286 mg, 1.350 mmol).

$^1$H NMR (400 MHz, MeOH-d$_4$) δ 7.45-7.34 (m, 4H), 7.19 (t, 1H, J=7.1 Hz), 6.77 (s, 1H), 4.01-3.79 (m, 4H), 3.80-3.50 (m, 4H), 3.50-3.38 (m, 2H), 3.26-3.11 (m, 2H), 2.80 (t, 2H, J=7.4 Hz), 2.46-2.28 (m, 2H), 1.83 (s, 9H), 1.87-1.68 (m, 2H), 1.03 (t, 3H, J=7.2 Hz)

Example 136

1-(3-(1-tert-butyl-3-propyl-1H-pyrazol-5-yl)propyl)-4-(2-fluorophenyl)piperazine (Compound 136)

171 mg (90%) of target compound was obtained by using a method same as in Example 1 by using 3-(1-tert-butyl-3-propyl-1H-pyrazol-5-yl)propanal (100 mg, 0.450 mmol), 1-(2-fluorophenyl)piperazine (81 mg, 0.450 mmol), DIPEA (0.118 mL, 0.675 mmol) and NaBH(OAc)$_3$ (286 mg, 1.350 mmol).

$^1$H NMR (400 MHz, MeOH-d$_4$) δ 7.19-7.02 (m, 4H), 6.77 (s, 1H), 3.82-3.74 (m, 2H), 3.68-3.52 (m, 2H), 3.49-3.38 (m, 6H), 3.23-3.09 (m, 2H), 2.80 (t, 2H, J=7.6 Hz), 2.42-2.29 (m, 2H), 1.83 (s, 9H), 1.87-1.69 (m, 2H), 1.03 (t, 3H, J=7.3 Hz)

Example 137

1-(3-(1-tert-butyl-3-propyl-1H-pyrazol-5-yl)propyl)-4-(4-chlorophenyl)piperazine (Compound 137)

171 mg (87%) of target compound was obtained by using a method same as in Example 1 by using 3-(1-tert-butyl-3-propyl-1H-pyrazol-5-yl)propanal (100 mg, 0.450 mmol), 1-(4-chlorophenyl)piperazine (121 mg, 0.450 mmol), DIPEA (0.118 mL, 0.675 mmol) and NaBH(OAc)$_3$ (286 mg, 1.350 mmol).

$^1$H NMR (400 MHz, MeOH-d$_4$) δ 7.28 (d, 2H, J=8.8 Hz), 7.06 (d, 2H, J=9.0 Hz), 6.76 (s, 1H), 3.90-3.71 (m, 4H), 3.43-3.21 (m, 6H), 3.21-3.11 (m, 2H), 2.80 (t, 2H, J=7.6 Hz), 2.41-2.30 (m, 2H), 1.82 (s, 9H), 1.88-1.72 (m, 2H), 1.03 (t, 3H, J=7.3 Hz)

Example 138

1-(3-(1-tert-butyl-3-propyl-1H-pyrazol-5-yl)propyl)-4-(2,4-dimethylphenyl)piperazine (Compound 138)

164 mg (84%) of target compound was obtained by using a method same as in Example 1 by using 3-(1-tert-butyl-3-propyl-1H-pyrazol-5-yl)propanal (100 mg, 0.450 mmol), 1-(2,4-dimethylphenyl)piperazine (86 mg, 0.450 mmol), DIPEA (0.118 mL, 0.675 mmol) and NaBH(OAc)$_3$ (286 mg, 1.350 mmol).

$^1$H NMR (400 MHz, MeOH-d$_4$) δ 7.13-7.01 (m, 3H), 6.77 (s, 1H), 3.82-3.69 (m, 2H), 3.50-3.28 (m, 8H), 2.82-2.14 (m, 2H), 2.80 (t, 2H, J=7.2 Hz), 2.34 (s, 3H), 2.43-2.32 (m, 2H), 2.27 (s, 3H), 1.83 (s, 9H), 1.86-1.71 (m, 2H), 1.03 (t, 3H, J=7.1 Hz)

Example 139

1-(3-(1-tert-butyl-3-propyl-1H-pyrazol-5-yl)propyl)-4-(3,4-dimethylphenyl)piperazine (Compound 139)

135 mg (69%) of target compound was obtained by using a method same as in Example 1 by using 3-(1-tert-butyl-3-propyl-1H-pyrazol-5-yl)propanal (100 mg, 0.450 mmol), 1-(3,4-dimethylphenyl)piperazine (86 mg, 0.450 mmol), DIPEA (0.118 mL, 0.675 mmol) and NaBH(OAc)$_3$ (286 mg, 1.350 mmol).

$^1$H NMR (400 MHz, MeOH-d$_4$) δ 7.41 (s, 1H), 7.36-7.23 (m, 2H), 6.77 (s, 1H), 4.08-3.71 (m, 8H), 3.60-3.46 (m, 2H), 3.28-3.16 (m, 2H), 2.80 (t, 2H, J=7.4 Hz), 2.42-2.31 (m, 2H), 2.34 (s, 3H), 2.29 (s, 3H), 1.83 (s, 9H), 1.86-1.70 (m, 2H), 1.03 (t, 3H, J=7.2 Hz)

Example 140

1-(3-(1-tert-butyl-3-propyl-1H-pyrazol-5-yl)propyl)-4-(2,3-dimethylphenyl)piperazine (Compound 140)

158 mg (81%) of target compound was obtained by using a method same as in Example 1 by using 3-(1-tert-butyl-3-propyl-1H-pyrazol-5-yl)propanal (100 mg, 0.450 mmol), 1-(2,3-dimethylphenyl)piperazine (86 mg, 0.450 mmol), DIPEA (0.118 mL, 0.675 mmol) and NaBH(OAc)$_3$ (286 mg, 1.350 mmol).

$^1$H NMR (400 MHz, MeOH-d$_4$) δ 7.09 (t, 1H, J=7.7 Hz), 7.02-6.93 (m, 2H), 6.77 (s, 1H), 3.79-3.70 (m, 2H), 3.49-3.34 (m, 4H), 3.37-3.29 (m, 4H), 3.29-3.21 (m, 2H), 2.80 (t, 2H, J=7.4 Hz), 2.42-2.32 (m, 2H), 2.28 (2s, 6H), 1.83 (s, 9H), 1.88-1.74 (m, 2H), 1.04 (t, 3H, J=7.2 Hz)

Example 141

1-(3-(1-tert-butyl-3-propyl-1H-pyrazol-5-yl)propyl)-4-(4-methoxyphenyl)piperazine (Compound 141)

162 mg (83%) of target compound was obtained by using a method same as in Example 1 by using 3-(1-tert-butyl-3-propyl-1H-pyrazol-5-yl)propanal (100 mg, 0.450 mmol), 1-(4-methoxyphenyl)piperazine (87 mg, 0.450 mmol), DIPEA (0.118 mL, 0.675 mmol) and NaBH(OAc)$_3$ (286 mg, 1.350 mmol).

$^1$H NMR (400 MHz, MeOH-d$_4$) δ 7.59 (d, 2H, J=8.8 Hz), 7.08 (d, 2H, J=8.8 Hz), 6.77 (s, 1H), 4.06-3.93 (m, 4H), 3.93-3.76 (m, 4H), 3.57-3.46 (m, 2H), 3.28-3.17 (m, 2H), 2.81 (t, 2H, J=7.2 Hz), 2.46-2.31 (m, 2H), 1.83 (s, 9H), 1.88-1.71 (m, 2H), 1.03 (t, 3H, J=7.1 Hz)

Example 142

4-(3-(1-tert-butyl-3-propyl-1H-pyrazol-5-yl)propyl)-2-methyl-1-m-tolylpiperazine (Compound 142)

190 mg (98%) of target compound was obtained by using a method same as in Example 1 by using 3-(1-tert-butyl-3-propyl-1H-pyrazol-5-yl)propanal (100 mg, 0.450 mmol), 2-methyl-1-m-tolylpiperazine (86 mg, 0.450 mmol), DIPEA (0.118 mL, 0.675 mmol) and NaBH(OAc)$_3$ (286 mg, 1.350 mmol).

$^1$H NMR (400 MHz, MeOH-d$_4$) δ 7.73-7.34 (m, 4H), 6.77 (s, 1H), 4.60-4.48 (m, 1H), 4.42-4.21 (m, 1H), 4.18-3.88 (m, 4H), 3.82-3.70 (m, 1H), 3.61-3.49 (m, 2H), 3.28-3.18 (m, 2H), 2.80 (t, 2H, J=7.6 Hz), 2.45 (s, 3H), 2.47-2.46 (m, 2H), 1.84 (s, 9H), 1.89-1.73 (m, 2H), 1.24 (d, 3H, J=6.4 Hz), 1.04 (t, 3H, J=7.3 Hz)

Example 143

1-(3-(1-tert-butyl-3-propyl-1H-pyrazol-5-yl)propyl)-4-(3,4-dichlorophenyl)piperazine (Compound 143)

199 mg (93%) of target compound was obtained by using a method same as in Example 1 by using 3-(1-tert-butyl-3-propyl-1H-pyrazol-5-yl)propanal (100 mg, 0.450 mmol), 1-(3,4-dichlorophenyl)piperazine (104 mg, 0.450 mmol), DIPEA (0.118 mL, 0.675 mmol) and NaBH(OAc)$_3$ (286 mg, 1.350 mmol).

$^1$H NMR (400 MHz, MeOH-d$_4$) δ 7.39 (d, 1H, J=8.4 Hz), 7.20 (s, 1H), 6.97 (d, 1H, J=8.3 Hz), 6.74 (s, 1H), 3.97-3.80 (m, 2H), 3.80-3.68 (m, 2H), 3.47-3.35 (m, 2H), 3.35-3.23 (m, 4H), 3.23-3.10 (m, 2H), 2.86-2.72 (m, 2H), 2.42-2.24 (m, 2H), 1.82 (s, 9H), 1.89-1.69 (m, 2H), 1.03 (t, 3H, J=6.6 Hz)

Example 144

1-(3-(1-tert-butyl-3-propyl-1H-pyrazol-5-yl)propyl)-4-(bis(4-fluorophenyl)methyl)piperazine (Compound 144)

239 mg (97%) of target compound was obtained by using a method same as in Example 1 by using 3-(1-tert-butyl-3-propyl-1H-pyrazol-5-yl)propanal (100 mg, 0.450 mmol), 1-(bis(4-fluorophenyl)methyl)piperazine (130 mg, 0.450 mmol), DIPEA (0.118 mL, 0.675 mmol) and NaBH(OAc)$_3$ (286 mg, 1.350 mmol).

$^1$H NMR (400 MHz, MeOH-d$_4$) δ 7.94-7.81 (m, 4H), 7.32-7.14 (m, 4H), 6.71 (s, 1H), 5.60 (br s, 1H), 4.93-4.76 (m, 4H), 3.65-3.50 (m, 4H), 3.50-3.40 (m, 2H), 3.21-3.10 (m, 2H), 2.78 (t, 2H, J=7.6 Hz), 2.40-2.24 (m, 2H), 1.81 (s, 9H), 1.88-1.70 (m, 2H), 1.01 (t, 3H, J=7.3 Hz)

Example 145

1-phenyl-4-(3-(1-phenyl-5-propyl-1H-pyrazol-3-yl)propyl)piperazine (Compound 145)

96 mg (69%) of target compound was obtained by using a method same as in Example 1 by using 3-(1-phenyl-5-propyl-1H-pyrazol-3-yl)propanal (80 mg, 0.330 mmol), 1-phenylpiperazine (0.050 mL, 0.330 mmol), DIPEA (0.090 mL, 0.495 mmol) and NaBH(OAc)$_3$ (210 mg, 0.990 mmol).

$^1$H NMR (400 MHz, MeOH-d$_4$) δ 7.78-7.63 (m, 5H), 7.42 (t, 2H, J=4.1 Hz), 7.33 (d, 2H J=3.9 Hz), 7.17 (t, 1H, J=7.3 Hz), 6.84 (s, 1H), 3.97-3.55 (m, 8H), 3.50-3.40 (m, 2H), 3.03 (t, 2H J=7.4 Hz), 2.68 (t, 2H, J=7.7 Hz), 2.44-2.30 (m, 2H), 1.79-1.64 (m, 2H), 0.95 (t, 3H, J=7.3 Hz)

Example 146

1-(2-fluorophenyl)-4-(3-(1-phenyl-5-propyl-1H-pyrazol-3-yl)propyl)piperazine (Compound 146)

96 mg (66%) of target compound was obtained by using a method same as in Example 1 by using 3-(1-phenyl-5-propyl-1H-pyrazol-3-yl)propanal (80 mg, 0.330 mmol), 1-(2-fluorophenyl)piperazine (59 mg, 0.330 mmol), DIPEA (0.090 mL, 0.495 mmol) and NaBH(OAc)$_3$ (210 mg, 0.990 mmol).

$^1$H NMR (400 MHz, MeOH-d$_4$) δ 7.78-7.60 (m, 5H), 7.20-7.02 (m, 4H), 6.76 (s, 1H), 3.82-3.68 (m, 2H), 3.68-3.53 (m, 2H), 3.43-3.30 (m, 4H), 3.30-3.16 (m, 2H), 2.99 (t, 2H, J=7.3 Hz), 2.67 (t, 2H, J=7.6 Hz), 2.40-2.26 (m, 2H), 1.78-1.62 (m, 2H), 0.95 (t, 3H, J=7.3 Hz)

Example 147

1-(4-chlorophenyl)-4-(3-(1-phenyl-5-propyl-1H-pyrazol-3-yl)propyl)piperazine (Compound 147)

69 mg (45%) of target compound was obtained by using a method same as in Example 1 by using 3-(1-phenyl-5-propyl- 1H-pyrazol-3-yl)propanal (80 mg, 0.330 mmol), 1-(4-chlorophenyl)piperazine (89 mg, 0.330 mmol), DIPEA (0.090 mL, 0.495 mmol) and NaBH(OAc)$_3$ (210 mg, 0.990 mmol).

$^1$H NMR (400 MHz, MeOH-d$_4$) δ 7.78-7.63 (m, 5H), 7.29 (d, 2H, J=3.4 Hz), 7.06 (d, 2H, J=3.4 Hz), 6.82 (s, 1H), 3.98-3.60 (m, 4H), 3.48-3.14 (m, 6H), 3.01 (t, 2H, J=7.6 Hz), 2.67 (t, 2H, J=7.7 Hz), 2.39-2.28 (m, 2H), 1.79-1.62 (m, 2H), 0.95 (t, 3H, J=7.4 Hz)

Example 148

1-(2,4-dimethylphenyl)-4-(3-(1-phenyl-5-propyl-1H-pyrazol-3-yl)propyl)piperazine (Compound 148)

73 mg (49%) of target compound was obtained by using a method same as in Example 1 by using 3-(1-phenyl-5-propyl-1H-pyrazol-3-yl)propanal (80 mg, 0.330 mmol), 1-(2,4-dimethylphenyl)piperazine (63 mg, 0.330 mmol), DIPEA (0.090 mL, 0.495 mmol) and NaBH(OAc)$_3$ (210 mg, 0.990 mmol).

$^1$H NMR (400 MHz, MeOH-d$_4$) δ 7.70-7.49 (m, 5H), 7.06-6.82 (m, 3H), 6.51 (s, 1H), 3.80-3.51 (m, 2H), 3.44-2.97 (m, 6H), 2.97-2.83 (m, 2H), 2.64 (t, 2H, J=7.5 Hz), 2.38-2.16 (m, 2H), 2.28 (s, 3H), 2.25 (s, 3H), 1.75-1.60 (m, 2H), 0.93 (t, 3H, J=7.2 Hz)

Example 149

1-(3,4-dimethylphenyl)-4-(3-(1-phenyl-5-propyl-1H-pyrazol-3-yl)propyl)piperazine (Compound 149)

159 mg (85%) of target compound was obtained by using a method same as in Example 1 by using 3-(1-phenyl-5-propyl-1H-pyrazol-3-yl)propanal (100 mg, 0.413 mmol), 1-(3,4-dimethylphenyl)piperazine (79 mg, 0.413 mmol), DIPEA (0.110 mL, 0.620 mmol) and NaBH(OAc)$_3$ (263 mg, 1.239 mmol).

$^1$H NMR (400 MHz, MeOH-d$_4$) δ 7.61-7.42 (m, 5H), 7.05 (d, 1H, J=8.2 Hz), 6.84 (s, 1H), 6.76 (d, 1H, J=2.5 Hz), 6.34 (s, 1H), 3.80-3.10 (m, 10H), 2.87 (t, 2H, J=7.2 Hz), 2.62 (t, 2H, J=7.7 Hz), 2.31-2.12 (m, 2H), 2.23 (s, 3H), 2.19 (s, 3H), 1.70-1.50 (m, 2H), 0.91 (t, 3H, J=7.4 Hz)

Example 150

1-(2,3-dimethylphenyl)-4-(3-(1-phenyl-5-propyl-1H-pyrazol-3-yl)propyl)piperazine (Compound 150)

124 mg (66%) of target compound was obtained by using a method same as in Example 1 by using 3-(1-phenyl-5-propyl-1H-pyrazol-3-yl)propanal (100 mg, 0.413 mmol), 1-(2,3-dimethylphenyl)piperazine (79 mg, 0.413 mmol), DIPEA (0.110 mL, 0.620 mmol) and NaBH(OAc)$_3$ (263 mg, 1.239 mmol).

$^1$H NMR (400 MHz, MeOH-d$_4$) δ 7.67-7.47 (m, 5H), 7.07 (t, 1H, J=7.7 Hz), 6.95 (d, 1H, J=7.4 Hz), 6.84 (d, 1H, J=7.9 Hz), 6.44 (s, 1H), 3.74-3.55 (m, 2H), 3.50-3.23 (m, 4H), 3.23-3.10 (m, 2H), 3.10-2.96 (m, 2H), 2.91 (t, 2H, J=7.1 Hz), 2.63 (t, 2H, J=7.6 Hz), 2.31-2.18 (m, 2H), 2.62 (s, 3H), 2.24 (s, 3H), 1.71-1.57 (m, 2H), 0.92 (t, 3H, J=7.3 Hz)

Example 151

1-(4-methoxyphenyl)-4-(3-(1-phenyl-5-propyl-1H-pyrazol-3-yl)propyl)piperazine (Compound 151)

42 mg (28%) of target compound was obtained by using a method same as in Example 1 by using 3-(1-phenyl-5-propyl-1H-pyrazol-3-yl)propanal (80 mg, 0.330 mmol), 1-(4-methoxyphenyl)piperazine (64 mg, 0.330 mmol), DIPEA (0.090 mL, 0.495 mmol) and NaBH(OAc)$_3$ (210 mg, 0.990 mmol).

$^1$H NMR (400 MHz, MeOH-d$_4$) δ 7.68-7.51 (m, 5H), 7.17 (d, 2H, J=8.7 Hz), 6.95 (d, 2H, J=8.6 Hz), 6.60 (s, 1H), 3.79 (s, 3H), 3.68-3.43 (m, 8H), 3.40-3.31 (m, 2H), 2.95 (t, 2H, J=7.0 Hz), 2.65 (t, 2H, J=7.5 Hz), 2.36-2.24 (m, 2H), 1.70-1.59 (m, 2H), 0.94 (t, 3H, J=7.2 Hz)

Example 152

2-methyl-4-(3-(1-phenyl-5-propyl-1H-pyrazol-3-yl)propyl)-1-m-tolylpiperazine (Compound 152)

68 mg (45%) of target compound was obtained by using a method same as in Example 1 by using 3-(1-phenyl-5-propyl-1H-pyrazol-3-yl)propanal (80 mg, 0.330 mmol), 2-methyl-1-m-tolylpiperazine (63 mg, 0.330 mmol), DIPEA (0.090 mL, 0.495 mmol) and NaBH(OAc)$_3$ (210 mg, 0.990 mmol).

$^1$H NMR (400 MHz, MeOH-d$_4$) δ 7.70-7.53 (m, 5H), 7.53-7.39 (m, 3H), 7.33 (s, 1H), 6.63 (s, 1H), 4.42-4.29 (m, 1H), 4.42-4.21 (m, 1H), 4.13-3.74 (m, 4H), 3.69-3.50 (m, 1H), 3.52-3.40 (m, 2H), 2.97 (t, 2H, J=7.3 Hz), 2.66 (t, 2H, J=7.7 Hz), 2.43 (s, 3H), 2.42-2.30 (m, 2H), 2.76-2.64 (m, 2H), 1.19 (d, 3H, J=6.5 Hz), 0.94 (t, 3H, J=7.3 Hz)

Example 153

1-(3,4-dichlorophenyl)-4-(3-(1-phenyl-5-propyl-1H-pyrazol-3-yl)propyl)piperazine (Compound 153)

77 mg (47%) of target compound was obtained by using a method same as in Example 1 by using 3-(1-phenyl-5-propyl-1H-pyrazol-3-yl)propanal (80 mg, 0.330 mmol), 1-(3,4-dichlorophenyl)piperazine (76 mg, 0.330 mmol), DIPEA (0.090 mL, 0.495 mmol) and NaBH(OAc)$_3$ (210 mg, 0.990 mmol).

$^1$H NMR (400 MHz, MeOH-d$_4$) δ 7.63-43 (m, 5H), 7.38 (d, 1H, J=8.9 Hz), 7.11 (s, 1H), 6.92 (d, 1H, J=4.5 Hz), 6.34 (s, 1H), 3.91-3.80 (m, 2H), 3.80-3.69 (m, 2H), 3.29-3.17 (m, 2H), 3.06-2.93 (m, 2H), 2.87 (t, 2H, J=7.0 Hz), 2.61 (t, 2H, J=7.6 Hz), 2.30-2.17 (m, 2H), 1.67-1.52 (m, 2H), 0.91 (t, 3H, J=7.4 Hz)

Example 154

1-(bis(4-fluorophenyl)methyl)-4-(3-(1-phenyl-5-propyl-1H-pyrazol-3-yl)propyl)piperazine (Compound 154)

128 mg (71%) of target compound was obtained by using a method same as in Example 1 by using 3-(1-phenyl-5-propyl-1H-pyrazol-3-yl)propanal (80 mg, 0.330 mmol), 1-(bis(4-fluorophenyl)methyl)piperazine (95 mg, 0.330 mmol), DIPEA (0.090 mL, 0.495 mmol) and NaBH(OAc)$_3$ (210 mg, 0.990 mmol).

$^1$H NMR (400 MHz, MeOH-d$_4$) δ 7.96-7.76 (m, 4H), 7.72-7.52 (m, 5H), 7.28-7.14 (m, 4H), 6.59 (s, 1H), 5.50 (br s, 1H), 3.88-3.69 (m, 4H), 3.57-3.36 (m, 6H), 2.92 (t, 2H, J=7.3 Hz), 2.63 (t, 2H, J=7.6 Hz), 2.35-2.20 (m, 2H), 1.69-1.56 (m, 2H), 0.92 (t, 3H, J=7.3 Hz)

Example 155

1-phenyl-4-(3-(1-phenyl-3-propyl-1H-pyrazol-5-yl)propyl)piperazine (Compound 155)

153 mg (87%) of target compound was obtained by using a method same as in Example 1 by using 3-(1-phenyl-3-propyl- 1H-pyrazol-5-yl)propanal (100 mg, 0.413 mmol), 1-phenylpiperazine (0.062 mL, 0.413 mmol), DIPEA (0.110 mL, 0.620 mmol) and NaBH(OAc)$_3$ (263 mg, 1.239 mmol).

$^1$H NMR (400 MHz, DMSO-d$_6$) δ 10.93 (br s, 1H), 7.54-7.32 (m, 5H), 7.24 (t, 2H, J=7.3 Hz), 6.98 (d, 2H, J=8.2 Hz), 6.90-6.79 (m, 1H), 6.24 (s, 1H), 3.86-3.68 (m, 2H), 3.58-3.44 (m, 2H), 3.20-3.01 (m, 6H), 2.71 (t, 2H, J=7.5 Hz), 2.61-2.43 (m, 2H), 2.16-2.02 (m, 2H), 1.71-1.55 (m, 2H), 0.94 (t, 3H, J=7.3 Hz)

Example 156

1-(2-fluorophenyl)-4-(3-(1-phenyl-3-propyl-1H-pyrazol-5-yl)propyl)piperazine (Compound 156)

151 mg (82%) of target compound was obtained by using a method same as in Example 1 by using 3-(1-phenyl-3-propyl-1H-pyrazol-5-yl)propanal (100 mg, 0.413 mmol), 1-(2-fluorophenyl)piperazine (74 mg, 0.413 mmol), DIPEA (0.110 mL, 0.620 mmol) and NaBH(OAc)$_3$ (263 mg, 1.239 mmol).

$^1$H NMR (400 MHz, MeOH-d$_4$) δ 7.58-7.39 (m, 5H), 7.08-6.92 (m, 4H), 6.36 (s, 1H), 3.62-3.45 (m, 4H), 3.20-3.01 (m, 6H), 2.80-2.68 (m, 2H), 2.59 (t, 2H, J=7.5 Hz), 2.16-1.99 (m, 2H), 1.74-1.59 (m, 2H), 0.94 (t, 3H, J=7.3 Hz)

Example 157

1-(4-chlorophenyl)-4-(3-(1-phenyl-3-propyl-1H-pyrazol-5-yl)propyl)piperazine (Compound 157)

118 mg (83%) of target compound was obtained by using a method same as in Example 1 by using 3-(1-phenyl-3-propyl-1H-pyrazol-5-yl)propanal (75 mg, 0.310 mmol), 1-(4-chlorophenyl)piperazine (83 mg, 0.310 mmol), DIPEA (0.081 mL, 0.465 mmol) and NaBH(OAc)$_3$ (197 mg, 0.930 mmol).

$^1$H NMR (400 MHz, MeOH-d$_4$) δ 7.57-7.42 (m, 5H), 7.18 (d, 2H, J=9.0 Hz), 6.91 (d, 2H, J=9.0 Hz), 6.44 (s, 1H), 3.77-3.67 (m, 2H), 3.60-3.50 (m, 2H), 3.18-2.98 (m, 6H), 2.72 (t, 2H, J=7.7 Hz), 2.62 (t, 2H, J=7.6 Hz), 2.12-2.00 (m, 2H), 2.73-2.60 (m, 2H), 0.95 (t, 3H, J=7.4 Hz)

Example 158

1-(2,4-dimethylphenyl)-4-(3-(1-phenyl-3-propyl-1H-pyrazol-5-yl)propyl)piperazine (Compound 158)

134 mg (95%) of target compound was obtained by using a method same as in Example 1 by using 3-(1-phenyl-3-propyl-1H-pyrazol-5-yl)propanal (75 mg, 0.310 mmol), 1-(2,4-dimethylphenyl)piperazine (59 mg, 0.310 mmol), DIPEA (0.081 mL, 0.465 mmol) and NaBH(OAc)$_3$ (197 mg, 0.930 mmol).

$^1$H NMR (400 MHz, MeOH-d$_4$) δ 7.60-7.40 (m, 5H), 7.05-6.90 (m, 3H), 6.31 (s, 1H), 3.67-3.50 (m, 2H), 3.28-3.03 (m, 8H), 2.83-2.72 (m, 2H), 2.62 (t, 2H, J=7.6 Hz), 2.27 (s, 3H), 2.25 (s, 3H), 2.18-2.02 (m, 2H), 1.76-1.63 (m, 2H), 1.00 (t, 3H, J=7.4 Hz)

Example 159

1-(3,4-dimethylphenyl)-4-(3-(1-phenyl-3-propyl-1H-pyrazol-5-yl)propyl)piperazine (Compound 159)

172 mg (92%) of target compound was obtained by using a method same as in Example 1 by using 3-(1-phenyl-3-propyl-1H-pyrazol-5-yl)propanal (100 mg, 0.413 mmol), 1-(3,4-dimethylphenyl)piperazine (79 mg, 0.413 mmol), DIPEA (0.110 mL, 0.620 mmol) and NaBH(OAc)$_3$ (263 mg, 1.239 mmol).

$^1$H NMR (400 MHz, DMSO-d$_6$) δ 10.94 (br s, 1H), 7.57-7.30 (m, 5H), 6.99 (d, 1H, J=8.2 Hz), 6.78 (s, 1H), 6.69 (d, 1H, J=4.2 Hz), 6.24 (s, 1H), 3.79-3.60 (m, 2H), 3.60-3.40 (m, 2H), 3.20-2.94 (m, 6H), 2.78-2.62 (m, 2H), 2.58-2.40 (m, 2H), 2.16 (s, 3H), 2.11 (s, 3H), 2.11-1.98 (m, 2H), 1.69-1.57 (m, 2H), 0.94 (t, 3H, J=7.3 Hz)

Example 160

1-(2,3-dimethylphenyl)-4-(3-(1-phenyl-3-propyl-1H-pyrazol-5-yl)propyl)piperazine (Compound 160)

146 mg (78%) of target compound was obtained by using a method same as in Example 1 by using 3-(1-phenyl-3-propyl-1H-pyrazol-5-yl)propanal (100 mg, 0.413 mmol), 1-(2,3-dimethylphenyl)piperazine (79 mg, 0.413 mmol), DIPEA (0.110 mL, 0.620 mmol) and NaBH(OAc)$_3$ (263 mg, 1.239 mmol).

$^1$H NMR (400 MHz, DMSO-d$_6$) δ 10.75 (br s, 1H), 7.57-7.34 (m, 5H), 7.12-6.98 (m, 1H), 6.94-6.81 (m, 2H), 6.24 (s, 1H), 3.58-3.40 (m, 2H), 3.24-3.00 (m, 8H), 2.71 (t, 2H, J=7.4 Hz), 2.59-2.48 (m, 2H), 2.20 (s, 3H), 2.14 (s, 3H), 2.12-2.00 (m, 2H), 1.70-1.58 (m, 2H), 0.94 (t, 3H, J=7.4 Hz)

Example 161

1-(4-methoxyphenyl)-4-(3-(1-phenyl-3-propyl-1H-pyrazol-5-yl)propyl)piperazine (Compound 161)

122 mg (65%) of target compound was obtained by using a method same as in Example 1 by using 3-(1-phenyl-3-propyl-1H-pyrazol-5-yl)propanal (100 mg, 0.413 mmol), 1-(4-methoxyphenyl)piperazine (80 mg, 0.413 mmol), DIPEA (0.110 mL, 0.620 mmol) and NaBH(OAc)$_3$ (263 mg, 1.239 mmol).

$^1$H NMR (400 MHz, DMSO-d$_6$) δ 10.79 (br s, 1H), 7.57-7.28 (m, 5H), 6.94 (d, 2H, J=8.6 Hz), 6.84 (d, 2H, J=8.9 Hz), 6.23 (s, 1H), 3.68 (s, 3H), 3.64-3.44 (m, 4H), 3.19-2.93 (m, 6H), 2.78-2.62 (m, 2H), 2.59-2.40 (m, 2H), 2.13-1.97 (m, 2H), 1.70-1.52 (m, 2H), 0.94 (t, 3H, J=7.3 Hz)

Example 162

2-methyl-4-(3-(1-phenyl-3-propyl-1H-pyrazol-5-yl)propyl)-1-m-tolylpiperazine (Compound 162)

132 mg (94%) of target compound was obtained by using a method same as in Example 1 by using 3-(1-phenyl-3-propyl-1H-pyrazol-5-yl)propanal (75 mg, 0.310 mmol), 2-methyl-1-m-tolylpiperazine (59 mg, 0.310 mmol), DIPEA (0.081 mL, 0.465 mmol) and NaBH(OAc)$_3$ (197 mg, 0.930 mmol).

$^1$H NMR (400 MHz, MeOH-d$_4$) δ 7.73-7.55 (m, 5H), 7.55-7.10 (m, 3H), 6.66 (s, 1H), 4.24 (bs, 1H), 4.10-3.77 (m, 2H), 3.77-3.58 (m, 2H), 3.58-3.39 (m, 1H), 2.85 (t, 2H, J=7.2 Hz), 2.75 (t, 2H, J=7.5 Hz), 2.40 (s, 3H), 2.31-2.16 (m, 2H), 1.87-1.70 (m, 2H), 1.14 (d, 3H, J=6.1 Hz), 1.04 (t, 3H, J=7.3 Hz)

Example 163

1-(3,4-dichlorophenyl)-4-(3-(1-phenyl-3-propyl-1H-pyrazol-5-yl)propyl)piperazine (Compound 163)

192 mg (94%) of target compound was obtained by using a method same as in Example 1 by using 3-(1-phenyl-3-propyl- 1H-pyrazol-5-yl)propanal (100 mg, 0.413 mmol), 1-(3,4-dichlorophenyl)piperazine (95 mg, 0.413 mmol), DIPEA (0.110 mL, 0.620 mmol) and NaBH(OAc)₃ (263 mg, 1.239 mmol).

¹H NMR (400 MHz, DMSO-d₆) δ 11.12 (br s, 1H), 7.59-7.35 (m, 6H), 7.23 (s, 1H), 6.98 (d, 1H, J=4.5 Hz), 6.23 (s, 1H), 3.93-3.77 (m, 2H), 3.58-3.43 (m, 2H), 3.26-3.13 (m, 2H), 3.13-2.94 (m, 4H), 2.77-2.63 (m, 2H), 2.55-2.40 (m, 2H), 2.13-1.98 (m, 2H), 1.69-1.52 (m, 2H), 0.93 (t, 3H, J=7.3 Hz)

Example 164

1-(bis(4-fluorophenyl)methyl)-4-(3-(1-phenyl-3-propyl-1H-pyrazol-5-yl)propyl)piperazine (Compound 164)

157 mg (92%) of target compound was obtained by using a method same as in Example 1 by using 3-(1-phenyl-3-propyl-1H-pyrazol-5-yl)propanal (75 mg, 0.310 mmol), 1-(bis(4-fluorophenyl)methyl)piperazine (89 mg, 0.310 mmol), DIPEA (0.081 mL, 0.465 mmol) and NaBH(OAc)₃ (197 mg, 0.930 mmol).

¹H NMR (400 MHz, MeOH-d₄) δ 7.83-7.66 (m, 4H), 7.66-7.50 (m, 5H), 7.21-7.03 (m, 4H), 6.60 (s, 1H), 5.30-5.10 (bs, 1H), 3.74-3.47 (m, 4H), 3.28-3.10 (m, 4H), 2.79 (t, 2H, J=7.5 Hz), 2.73 (t, 2H, J=7.6 Hz), 2.21-2.08 (m, 2H), 1.83-1.68 (m, 2H), 1.02 (t, 3H, J=7.3 Hz)

Example 165

1-(2-fluorophenyl)-4-(3-(1-(3-chlorophenyl)-3-propyl-1H-pyrazol-5-yl)propyl)piperazine (Compound 165)

91.87 mg (46.19%) of target compound was obtained by using a method same as in Example 1 by using 3-(1-(3-chlorophenyl)-3-propyl-1H-pyrazol-5-yl)propanal (124.75 mg, 0.451 mmol), 1-(2-fluorophenyl)piperazine (92 mL, 0.586 mmol), and NaCNBH3 (85.02 mg, 1.353 mmol).

¹H NMR (300 MHz, CDCl₃) δ 7.48 (d, 1H), 7.36-7.31 (m, 3H), 7.03-6.87 (m, 4H), 6.04 (s, 1H), 3.07 (t, 4H), 2.69 (t, 2H), 2.66-2.57 (m, 6H), 2.02-1.76 (m, 2H), 1.74-1.62 (m, 2H), 0.97 (t, 3H)

Example 166

1-(2-fluorophenyl)-4-(3-(1-(4-methoxyphenyl)-3-propyl-1H-pyrazol-5-yl)propyl)piperazine (Compound 166)

114 mg (66.0%) of target compound was obtained by using a method same as in Example 1 by using 3-(1-(4-methoxyphenyl)-3-propyl-1H-pyrazol-5-yl)propanal (107.73 mg, 0.396 mmol), 1-(2-fluorophenyl)piperazine (82.22 mL, 0.514 mmol), and NaCNBH3 (74.58 mg, 1.187 mmol).

¹H NMR (300 MHz, CDCl₃) δ 7.31-7.29 (m, 2H), 7.04-6.89 (m, 6H), 6.00 (s, 1H), 3.81 (s, 3H), 3.07 (t, 4H), 2.63-2.57 (m, 8H), 2.38 (t, 2H), 1.83-1.78 (m, 2H), 1.75-1.61 (m, 2H), 0.97 (t, 3H)

Example 167

1-(2-fluorophenyl)-4-(3-(1-(4-methylphenyl)-3-propyl-1H-pyrazol-5-yl)propyl)piperazine (Compound 167)

93 mg (59.7%) of target compound was obtained by using a method same as in Example 1 by using 3-(1-(4-methylphenyl)-3-propyl-1H-pyrazol-5-yl)propanal (95 mg, 0.371 mmol), 1-(2-fluorophenyl)piperazine (76 mL, 0.482 mmol), and NaCNBH3 (70 mg, 1.112 mmol).

¹H NMR (300 MHz, CDCl₃) δ 7.28 (d, 2H), 7.21 (d, 2H), 7.06-6.87 (m, 4H), 6.01 (s, 1H), 3.06 (t, 4H), 2.67-2.58 (m, 4H), 2.54 (t, 3H), 2.36 (t, 5H), 2.40-2.35 (m, 5H), 1.83-1.75 (m, 2H), 1.72-1.62 (m, 2H), 0.98 (t, 3H)

Example 168

1-(2-fluorophenyl)-4-(3-(1-(4-fluorophenyl)-3-propyl-1H-pyrazol-5-yl)propyl)piperazine (Compound 168)

119 mg (65.0%) of target compound was obtained by using a method same as in Example 1 by using 3-(1-(4-fluorophenyl)-3-propyl-1H-pyrazol-5-yl)propanal (112.3 mg, 0.431 mmol), 1-(2-fluorophenyl)piperazine (102.22 mL, 0.647 mmol), and NaCNBH3 (274.29 mg, 1.294 mmol).

¹H NMR (300 MHz, CDCl₃) δ 7.39-7.34 (m, 2H), 7.14-7.08 (m, 2H), 7.03-6.88 (m, 4H), 6.02 (s, 1H), 3.10 (t, 4H), 2.68 (t, 4H), 2.64-2.57 (m, 4H), 2.50-2.45 (m, 2H), 1.85-1.80 (m, 2H), 1.71-1.64 (m, 2H), 0.97 (t, 3H)

Example 169

1-(2-fluorophenyl)-4-(3-(1-(4-chlorophenyl)-3-propyl-1H-pyrazol-5-yl)propyl)piperazine (Compound 169)

60 mg (82.3%) of target compound was obtained by using a method same as in Example 1 by using 3-(1-(4-chlorophenyl)-3-propyl-1H-pyrazol-5-yl)propanal (45.74 mg, 0.165 mmol), 1-(2-fluorophenyl)piperazine (39.16 mL, 0.247 mmol), and NaBH(OAc)₃ (198 mg, 0.936 mmol).

¹H NMR (300 MHz, CDCl₃) δ 7.42-7.34 (m, 4H), 7.04-6.88 (m, 4H), 6.04 (s, 1H), 3.08 (t, 4H), 2.68-2.57 (m, 8H), 2.41 (t, 2H), 1.86-1.78 (m, 2H), 1.76-1.62 (m, 2H), 0.97 (t, 3H)

Example 170

1-(2-fluorophenyl)-4-(3-(1-(4-trifluorophenyl)-3-propyl-1H-pyrazol-5-yl)propyl)piperazine (Compound 170)

140 mg (84.8%) of target compound was obtained by using a method same as in Example 1 by using 3-(1-(4-trifluorophenyl)-3-propyl-1H-pyrazol-5-yl)propanal (108 mg, 0.348 mmol), 1-(2-fluorophenyl)piperazine (82.5 mL, 0.522 mmol), and NaBH(OAc)₃ (198 mg, 0.936 mmol).

¹H NMR (300 MHz, CDCl₃) δ 7.69 (d, 2H), 7.56 (d, 2H), 7.01-6.98 (m, 2H), 6.94-6.87 (m, 2H), 6.08 (s, 1H), 3.08 (t, 4H), 2.71 (t, 2H), 2.63-2.58 (m, 6H), 2.45 (t, 2H), 1.89-1.82 (m, 2H), 1.72-1.62 (m, 2H), 0.97 (t, 3H)

Example 171

1-(2-fluorophenyl)-4-(3-(1-(4-trifluoromethoxyphenyl)-3-propyl-1H-pyrazol-5-yl)propyl)piperazine (Compound 171)

100 mg (80.6%) of target compound was obtained by using a method same as in Example 1 by using 3-(1-(4-trifluoromethoxyphenyl)-3-propyl-1H-pyrazol-5-yl)propanal (82.5 mg, 0.253 mmol), 1-(2-fluorophenyl)piperazine (60 mL, 0.379 mmol), and NaBH(OAc)₃ (198 mg, 0.936 mmol).

¹H NMR (300 MHz, CDCl₃) δ 7.47-7.44 (m, 2H), 7.29-7.26 (m, 2H), 7.02-6.88 (m, 4H), 6.04 (s, 1H), 3.05 (t, 4H), 2.67 (t, 2H), 2.60 (t, 2H), 2.56-2.53 (m, 4H), 1.85-1.80 (m, 2H), 1.77-1.62 (m, 2H), 0.97 (t, 3H)

Example 172

1-(2-fluorophenyl)-4-(3-(1-(4-nitrophenyl)-3-propyl-1H-pyrazol-5-yl)propyl)piperazine (Compound 172)

70 mg (82.5%) of target compound was obtained by using a method same as in Example 1 by using 3-(1-(4-nitrophenyl)-3-propyl-1H-pyrazol-5-yl)propanal 54 mg, 0.188 mmol), 1-(2-fluorophenyl)piperazine (39 mL, 0.244 mmol), and NaBH(OAc)₃ (198 mg, 0.936 mmol).
¹H NMR (300 MHz, CDCl₃) δ 8.28 (d, 2H), 7.66 (d, 2H0, 7.03-6.89 (m, 4H), 6.12 (s, 1H), 3.08 (m, 4H), 2.77 (t, 2H), 2.61 (m, 6H), 2.45 (t, 2H), 1.96-1.82 (m, 2H), 1.74-1.62 (m, 2H), 0.98 (t, 3H)

Example 173

1-(2-fluorophenyl)-4-(3-(1-benzyl-3-propyl-1H-pyrazol-5-yl)propyl)piperazine (Compound 173)

86 mg (84.5%) of target compound was obtained by using a method same as in Example 1 by using 3-(1-benzyl-3-propyl-1H-pyrazol-5-yl)propanal (62 mg, 0.242 mmol), 1-(2-fluorophenyl)piperazine (76 mL, 0.484 mmol), and NaBH(OAc)₃ (198 mg, 0.936 mmol).
¹H NMR (300 MHz, CDCl₃) δ 7.29-7.20 (m, 3H), 7.03-6.88 (m, 6H), 5.89 (s, 1H), 5.25 (s, 2H), 3.05 (t, 4H), 2.58 (t, 2H), 2.52-2.48 (m, 6H), 2.33 (t, 2H), 1.78-1.60 (m, 4H), 0.96 (s, 3H)

Example 174

1-(2-fluorophenyl)-4-(3-(1-(3-nitrophenyl)-3-propyl-1H-pyrazol-5-yl)propyl)piperazine (Compound 174)

67 mg (83.6%) of target compound was obtained by using a method same as in Example 1 by using 3-(1-(3-nitrophenyl)-3-propyl-1H-pyrazol-5-yl)propanal (51 mg, 0.178 mmol), 1-(2-fluorophenyl)piperazine (42 mL, 0.266 mmol), and NaBH(OAc)₃ (198 mg, 0.936 mmol).
¹H NMR (300 MHz, CDCl₃) δ 8.32 (t, 1H), 8.16 (m, 1H), 7.82 (m, 1H), 7.61 (t, 1H), 7.00-6.93 (m, 2H), 6.91-6.88 (m, 2H), 6.10 (s, 1H), 3.06 (t, 4H), 2.74 (t, 2H), 2.63-2.38 (m, 6H), 2.43 (t, 2H), 1.91-1.81 (m, 2H), 1.75-1.63 (m, 2H), 0.98 (t, 3H)

Example 175

1-(2-fluorophenyl)-4-(3-(1-(2'-pyridyl)-3-propyl-1H-pyrazol-5-yl)propyl)piperazine (Compound 175)

100 mg (90.5%) of target compound was obtained by using a method same as in Example 1 by using 3-(1-(2'-pyridyl)-3-propyl-1H-pyrazol-5-yl)propanal (66 mg, 0.271 mmol), 1-(2-fluorophenyl)piperazine (86 mL, 0.543 mmol), and NaBH(OAc)₃ (198 mg, 0.936 mmol).
¹H NMR (300 MHz, CDCl₃) δ 8.39-8.37 (m, 1H), 7.83 (d, 1H), 7.77-7.74 (m, 1H), 7.12 (m, 1H), 7.03-6.90 (m, 4H), 6.04 (s, 1H), 3.15-3.09 (m, 6H), 2.65-2.58 (m, 6H), 2.49 (t, 2H), 2.02-1.87 (m, 2H), 1.72-1.65 (m, 2H), 0.98 (t, 3H)

Example 176

1-phenyl-4-(3-(1-phenyl-3-isopropyl-1H-pyrazol-5-yl)propyl)piperazine (Compound 176)

36 mg (86%) of target compound was obtained by using a method same as in Example 1 by using 3-(1-phenyl-3-isopropyl-1H-pyrazol-5-yl)propanal (26 mg, 0.108 mmol), 1-phenylpiperazine (0.016 mL, 0.108 mmol), DIPEA (0.028 mL, 0.162 mmol) and NaBH(OAc)₃ (69 mg, 0.325 mmol).
¹H NMR (300 MHz, MeOH-d₄) δ 7.57-7.43 (m, 5H), 7.26-7.21 (m, 2H), 6.96 (d, 2H, J=7.9 Hz), 6.85 (t, 1H, J=7.3 Hz), 6.22 (s, 1H), 3.18-3.15 (m, 4H), 3.00-2.95 (m, 1H), 2.74-2.68 (m, 2H), 2.66-2.63 (m, 4H), 2.49-2.45 (m, 2H), 1.85-1.79 (m, 2H), 1.29 (d, 6H, J=6.9 Hz)

Example 177

1-(2-fluorophenyl)-4-(3-(1-phenyl-3-isopropyl-1H-pyrazol-5-yl)propyl)piperazine (Compound 177)

143 mg (99%) of target compound was obtained by using a method same as in Example 1 by using 3-(1-phenyl-3-isopropyl-1H-pyrazol-5-yl)propanal (86 mg, 0.357 mmol), 1-(2-fluorophenyl)piperazine (65 mg, 0.362 mmol), DIPEA (0.094 mL, 0.540 mmol) and NaBH(OAc)₃ (237 mg, 1.118 mmol).
¹H NMR (300 MHz, MeOH-d₄) δ 7.58-7.44 (m, 5H), 7.07-6.97 (m, 4H), 6.22 (s, 1H), 3.11-3.08 (m, 4H), 3.03-2.93 (m, 1H), 2.74-2.69 (m, 6H), 2.54-2.40 (m, 2H), 1.89-1.78 (m, 2H), 1.29 (d, 3H, J=6.9 Hz)

Example 178

1-phenyl-4-(3-(1-phenyl-3-butyl-1H-pyrazol-5-yl)propyl)piperazine (Compound 178)

100 mg (80%) of target compound was obtained by using a method same as in Example 1 by using 3-(1-phenyl-3-butyl-1H-pyrazol-5-yl)propanal (80 mg, 0.312 mmol), 1-phenylpiperazine (0.047 mL, 0.312 mmol), DIPEA (0.081 mL, 0.468 mmol) and NaBH(OAc)₃ (198 mg, 0.936 mmol).
¹H NMR (300 MHz, MeOH-d₄) δ 7.58-7.43 (m, 5H), 7.27-7.21 (m, 2H), 6.98-6.95 (m, 2H), 6.88-6.83 (m, 1H), 6.24 (s, 1H), 3.62-3.45 (m, 4H), 3.20-3.01 (m, 8H), 2.80-2.68 (m, 2H), 2.59 (t, 2H, J=7.5 Hz), 2.16-1.99 (m, 2H), 1.74-1.59 (m, 2H), 0.94 (t, 3H, J=7.3 Hz)

Example 179

1-(2-fluorophenyl)-4-(3-(1-phenyl-3-butyl-1H-pyrazol-5-yl)propyl)piperazine (Compound 179)

196.6 mg (86%) of target compound was obtained by using a method same as in Example 1 by using 3-(1-phenyl-3-butyl-1H-pyrazol-5-yl)propanal (140 mg, 0.546 mmol), 1-(2-fluorophenyl)piperazine (130 mL, 0.819 mmol), and NaBH(OAc)₃ (excess amount).
¹H NMR (300 MHz, CDCl₃) δ 7.42-7.39 (m, 5H), 7.03-6.89 (m, 4H), 6.03 (s, 1H), 3.06 (t, 4H), 2.70-2.61 (m, 4H), 2.54 (t, 4H), 2.38 (t, 2H), 1.81-1.76 (m, 2H), 1.68-1.63 (m, 2H), 1.44-1.36 (m, 2H), 0.93 (t, 3H)

Example 180

1-(2-fluorophenyl)-4-(3-(1-(3-chlorophenyl)-3-butyl-1H-pyrazol-5-yl)propyl)piperazine (Compound 180)

312 mg (84.2%) of target compound was obtained by using a method same as in Example 1 by using 3-(1-(3-chlorophenyl)-3-butyl-1H-pyrazol-5-yl)propanal (236.75 mg, 0.814 mmol), 1-(2-fluorophenyl)piperazine (192.9 mL, 1.221 mmol), and NaBH(OAc)$_3$ (198 mg, 0.936 mmol).

$^1$H NMR (300 MHz, CDCl$_3$) δ 7.29-7.20 (m, 3H), 7.03-6.89 (m, 6H), 5.89 (s, 1H), 5.25 (s, 2H), 3.06 (t, 4H), 2.60 (t, 2H), 2.53-2.48 (m, 6H), 2.34 (t, 2H), 1.76-1.71 (m, 2H), 1.65-1.58 (m, 2H), 1.42-1.35 (m, 2H), 0.92 (t, 3H)

Example 181

1-(2-fluorophenyl)-4-(3-(1-(4-methoxyphenyl)-3-butyl-1H-pyrazol-5-yl)propyl)piperazine (Compound 181)

308 mg (78%) of target compound was obtained by using a method same as in Example 1 by using 3-(1-(4-methoxyphenyl)-3-butyl-1H-pyrazol-5-yl)propanal (251 mg, 0.876 mmol), 1-(2-fluorophenyl)piperazine (208 mL, 1.314 mmol), and NaBH(OAc)$_3$ (198 mg, 0.936 mmol).

$^1$H NMR (300 MHz, CDCl$_3$) δ 7.31-7.29 (m, 2H), 7.04-6.90 (m, 6H), 6.00 (s, 1H), 3.82 (s, 3H), 3.07 (m, 4H), 2.64-2.57 (m, 8H), 2.38 (m, 2H), 1.81-1.76 (m, 2H), 1.69-1.59 (m, 2H), 1.45-1.35 (m, 2H), 0.92 (t, 3H)

Example 182

1-(2-fluorophenyl)-4-(3-(1-(4-methylphenyl)-3-butyl-1H-pyrazol-5-yl)propyl)piperazine (Compound 182)

297 mg (70.6%) of target compound was obtained by using a method same as in Example 1 by using 3-(1-(4-methylphenyl)-3-butyl-1H-pyrazol-5-yl)propanal (248 mg, 0.968 mmol), 1-(2-fluorophenyl)piperazine (229 mL, 1.451 mmol), and NaBH(OAc)$_3$ (198 mg, 0.936 mmol).

$^1$H NMR (300 MHz, CDCl$_3$) δ 7.28-7.26 (m, 2H), 7.18 (d, 2H), 6.99-6.92 (m, 2H), 6.92-6.83 (m, 2H), 6.00 (s, 1H), 3.03 (t, 4H), 2.65-2.60 (m, 4H), 2.50 (t, 4H), 2.36-2.32 (m, 5H), 1.78-1.67 (m, 2H), 1.65-1.59 (m, 2H), 1.43-1.44 (m, 2H), 0.91 (t, 3H)

Example 183

1-(2-fluorophenyl)-4-(3-(1-(4-fluorophenyl)-3-butyl-1H-pyrazol-5-yl)propyl)piperazine (Compound 183)

218 mg (87.5%) of target compound was obtained by using a method same as in Example 1 by using 3-(1-(4-fluorophenyl)-3-butyl-1H-pyrazol-5-yl)propanal (155.9 mg, 0.568 mmol), 1-(2-fluorophenyl)piperazine (106 mL, 0.852 mmol), and NaBH(OAc)$_3$ (198 mg, 0.936 mmol).

$^1$H NMR (300 MHz, CDCl$_3$) δ 7.40-7.35 (m, 2H), 7.13-7.08 (m, 2H), 7.03-6.88 (m, 4H), 6.02 (s, 1H), 3.06 (t, 4H), 2.64-2.59 (m, 4H), 2.54 (t, 4H), 2.37 (t, 2H), 1.80-1.67 (m, 2H), 1.66-1.59 (m, 2H), 1.43-1.36 (m, 2H), 0.92 (t, 3H)

Example 184

1-(2-fluorophenyl)-4-(3-(1-(4-chlorophenyl)-3-butyl-1H-pyrazol-5-yl)propyl)piperazine (Compound 184)

98.4 mg (78.5%) of target compound was obtained by using a method same as in Example 1 by using 3-(1-(4-chlorophenyl)-3-butyl-1H-pyrazol-5-yl)propanal (80.1 mg, 0.275 mmol), 1-(2-fluorophenyl)piperazine (65 mL, 0.413 mmol), and NaBH(OAc)$_3$ (198 mg, 0.936 mmol).

$^1$H NMR (300 MHz, CDCl$_3$) δ 7.38-7.34 (m, 4H), 7.02-6.87 (m, 4H), 6.03 (s, 1H), 3.05 (t, 4H), 2.67-2.59 (m, 4H), 2.54 (t, 4H), 2.37 (t, 2H), 1.83-1.75 (m, 2H), 1.69-1.59 (m, 2H), 1.43-1.35 (m, 2H), 0.92 (t, 3H)

Example 185

1-(2-fluorophenyl)-4-(3-(1-(4-trifluoromethylphenyl)-3-butyl-1H-pyrazol-5-yl)propyl)piperazine (Compound 185)

258.6 mg (84.7%) of target compound was obtained by using a method same as in Example 1 by using 3-(1-(4-trifluoromethylphenyl)-3-butyl-1H-pyrazol-5-yl)propanal (202.6 mg, 0.625 mmol), 1-(2-fluorophenyl)piperazine (148 mL, 0.937 mmol), and NaBH(OAc)$_3$ (198 mg, 0.936 mmol).

$^1$H NMR (300 MHz, CDCl$_3$) δ 7.70 (d, 2H), 7.58 (d, 2H), 7.04-7.00 (m, 2H), 6.96-6.88 (m, 2H), 6.08 (s, 1H), 3.06 (t, 4H), 2.72 (t, 2H), 2.64 (t, 2H), 2.56 (t, 4H), 2.40 (t, 2H), 1.85-1.80 (m, 2H), 1.68-1.63 (m, 2H), 1.44-1.37 (m, 2H), 0.93 (t, 3H)

Example 186

1-(2-fluorophenyl)-4-(3-(1-(4-nitrophenyl)-3-butyl-1H-pyrazol-5-yl)propyl)piperazine (Compound 186)

260 mg (90.0%) of target compound was obtained by using a method same as in Example 1 by using 3-(1-(4-nitrophenyl)-3-butyl-1H-pyrazol-5-yl)propanal (187 mg, 0.625 mmol), 1-(2-fluorophenyl)piperazine (148 mL, 0.937 mmol), and NaBH(OAc)$_3$ (198 mg, 0.936 mmol).

$^1$H NMR (300 MHz, CDCl$_3$) δ 8.30-8.27 (m, 2H), 7.67-7.64 (m, 2H), 7.02-6.88 (m, 4H), 6.11 (s, 1H), 3.05 (t, 4H), 2.77 (t, 2H), 2.64 (t, 2H), 2.56 (t, 4H), 2.41 (t, 2H), 1.87-1.82 (m, 2H), 1.67-1.58 (m, 2H), 1.42-1.35 (m, 2H), 0.92 (t, 3H)

Example 187

1-(2-fluorophenyl)-4-(3-(1-benzyl-3-butyl-4H-pyrazol-5-yl)propyl)piperazine (Compound 187)

180 mg (84.2%) of target compound was obtained by using a method same as in Example 1 by using 3-(1-benzyl-3-butyl-1H-pyrazol-5-yl)propanal (133 mg, 0.492 mmol), 1-(2-fluorophenyl)piperazine (155 mL, 0.984 mmol), and NaBH(OAc)$_3$ (198 mg, 0.936 mmol).

$^1$H NMR (300 MHz, CDCl$_3$) δ 7.42-7.32 (m, 5H), 7.01-6.89 (m, 4H), 6.03 (s, 1H), 3.06 (t, 4H), 2.70-2.61 (m, 4H), 2.54 (t, 4H), 2.38 (t, 2H), 1.81-1.76 (m, 2H), 1.68-1.63 (m, 2H), 1.44-1.36 (m, 2H), 0.93 (t, 3H)

Example 188

1-(2-fluorophenyl)-4-(3-(1-(3-nitrophenyl)-3-butyl-1H-pyrazol-5-yl)propyl)piperazine (Compound 188)

218 mg (66.2%) of target compound was obtained by using a method same as in Example 1 by using 3-(1-(3-nitrophenyl)-3-butyl-1H-pyrazol-5-yl)propanal (213 mg, 0.707 mmol), 1-(2-fluorophenyl)piperazine (167 mL, 1.060 mmol), and NaBH(OAc)$_3$ (198 mg, 0.936 mmol).

$^1$H NMR (300 MHz, CDCl$_3$) δ 8.29 (s, 1H), 8.14 (d, 1H), 7.79 (d, 1H), 7.57 (t, 1H), 7.01-6.82 (m, 4H), 6.08 (s, 1H), 3.02 (m, 4H), 2.71 (t, 2H), 2.63-2.56 (m, 6H), 2.41 (t, 2H), 1.88-1.81 (m, 2H), 1.65-1.57 (m, 2H), 1.41-1.33 (m, 2H), 0.90 (t, 3H)

Example 189

1-(2-fluorophenyl)-4-(3-(1-(2'-pyridyl)-3-butyl-1H-pyrazol-5-yl)propyl)piperazine (Compound 189)

90 mg (78.5%) of target compound was obtained by using a method same as in Example 1 by using 3-(1-(2'-pyridyl)-3-butyl-1H-pyrazol-5-yl)propanal (70 mg, 0.272 mmol), 1-(2-fluorophenyl)piperazine (65 mL, 0.408 mmol), and NaBH(OAc)$_3$ (198 mg, 0.936 mmol).
$^1$H NMR (300 MHz, CDCl$_3$) δ 8.38-8.36 (m, 1H), 7.83 (d, 1H), 7.75-7.72 (m, 1H), 7.10-7.02 (m, 1H), 7.00-6.89 (m, 4H), 6.04 (s, 1H), 3.15-3.07 (m, 6H), 2.66-2.61 (m, 6H), 2.45 (t, 2H), 1.91-1.86 (m, 2H), 1.67-1.62 (m, 2H), 1.43-1.39 (m, 2H), 0.93 (t, 3H)

Example 190

1-phenyl-4-(3-(1-phenyl-3-isobutyl-1H-pyrazol-5-yl)propyl)piperazine (Compound 190)

120 mg (95%) of target compound was obtained by using a method same as in Example 1 by using 3-(1-phenyl-3-isobutyl-1H-pyrazol-5-yl)propanal (80 mg, 0.312 mmol), 1-phenylpiperazine (0.047 mL, 0.312 mmol), DIPEA (0.081 mL, 0.468 mmol) and NaBH(OAc)$_3$ (198 mg, 0.936 mmol).
$^1$H NMR (300 MHz, MeOH-d$_4$) δ 7.57-7.43 (m, 5H), 7.26-7.21 (m, 2H), 6.96 (d, 2H, J=7.9 Hz), 6.85 (t, 1H, J=7.3 Hz), 6.22 (s, 1H), 3.18-3.15 (m, 4H), 3.00-2.95 (m, 1H), 2.74-2.68 (m, 4H), 2.66-2.63 (m, 4H), 2.49-2.45 (m, 2H), 1.85-1.79 (m, 2H), 1.29 (d, 6H, J=6.9 Hz)

Example 191

1-(2-fluorophenyl)-4-(3-(1-phenyl-3-isobutyl-1H-pyrazol-5-yl)propyl)piperazine (Compound 191)

121 mg (92%) of target compound was obtained by using a method same as in Example 1 by using 3-(1-phenyl-3-isobutyl-1H-pyrazol-5-yl)propanal (80 mg, 0.312 mmol), 1-(2-fluorophenyl)piperazine (56 mg, 0.312 mmol), DIPEA (0.082 mL, 0.468 mmol) and NaBH(OAc)$_3$ (198 mg, 0.936 mmol).
$^1$H NMR (300 MHz, MeOH-d$_4$) δ 7.58-7.44 (m, 5H), 7.07-6.97 (m, 4H), 6.22 (s, 1H), 3.11-3.08 (m, 4H), 3.03-2.93 (m, 1H), 2.74-2.69 (m, 8H), 2.54-2.40 (m, 2H), 1.89-1.78 (m, 2H), 1.29 (d, 3H, J=6.9 Hz)

REFERENCE EXAMPLES

The following reference examples are embodiments of methods for preparing the compound represented by the above formula 2 according to the reaction scheme II, however, they should not be construed as limiting the scope of the present invention.

Reference Example 1

1-(4-chlorophenyl)-6-hydroxyhexane-1,3-dione (Formula 5)

To 60 mL of benzene was added NaOMe (5.4 g, 99.612 mmol) under nitrogen atmosphere and stirred. The above mixture was added then with 30 mL of 4-chloroacetophenone (5.9 mL, 45.278 mmol) after mixing it with 30 mL of benzene and stirred for 30 min at 40° C. Then, γ-butyrolactone (7.0 mL, 90.556 mmol), after mixing it with 30 mL of benzene, was slowly added thereto and stirred for 16 hrs at 40° C. The progress and completion of the reaction were confirmed by means of TLC. Upon completion of the reaction, the reaction mixture was cooled down to room temperature and the solvent was removed from the reaction mixture under reduced pressure. The reaction mixture was diluted with EtOAc, and added with water. The aqueous layer was extracted with EtOAc and the organic layer was dried with anhydrous MgSO$_4$ and filtered. The resulting filtrate was concentrated under reduced pressure and the resulting concentrate was passed through column chromatography (EtOAc:Hexane=1:1, v/v) to obtain 5.9 g (54%) of target compound.
$^1$H NMR (400 MHz, CDCl$_3$) δ 7.87-7.74 (m, 2H), 7.42-7.31 (m, 2H), 6.47 (s, 1H), 4.31 (t, 2H, J=7.0 Hz), 3.31-3.23 (m, 2H), 2.21-2.10 (m, 2H)

Reference Example 2

3-(1-tert-butyl-5-(4-chlorophenyl)-1H-pyrazol-3-yl)propane-1-ol (Formula 6a)

1-(4-chlorophenyl)-6-hydroxyhexane-1,3-dione (2.0 g, 8.310 mmol) was dissolved in 15 mL of methanol. t-BuNHNH$_2$.HCl (2.1 g, 16.620 mmol) was dissolved in 15 mL of methanol and then added with triethylamine (TEA; 2.3 mL, 16.620 mmol). After they were all dissolved, the mixture was added into a solution of 1-(4-chlorophenyl)-6-hydroxyhexane-1,3-dione, and then stirred for 14 hours at 40° C. The reaction progress and completion were confirmed by TLC. Upon completion of the reaction, while the temperature was kept at room temperature, the solvent was removed under reduced pressure. The reaction residue was diluted with EtOAc, and added with water. The aqueous layer was extracted with EtOAc and the organic layer was dried with anhydrous MgSO$_4$ and filtered and concentrated under reduced pressure. The concentrate was separated by column chromatography (EtOAc:Hexane=2:3, v/v) to obtain 1.57 g (64%) of target compound.
$^1$H NMR (400 MHz, CDCl$_3$) δ 7.36 (d, 2H, J=8.1 Hz), 7.26 (d, 2H, J=8.3 Hz), 5.93 (s, 1H), 3.76 (t, 2H, J=5.7 Hz), 2.78 (t, 2H, J=6.7 Hz), 1.97-1.90 (m, 2H), 1.43 (s, 9H)

Reference Example 3

3-(1-tert-butyl-5-propyl-1H-pyrazol-3-yl)propan-1-ol (formula 6a) and 3-(1-tert-butyl-3-propyl-1H-pyrazol-5-yl)propan-1-ol (Formula 6b)

1-hydroxynonane-4,6-dione (3.5 g, 20.3 mmol) was dissolved in 10 mL of methanol. t-BuNHNH$_2$.HCl (7.6 g, 60.968 mmol) was dissolved in 30 mL of methanol and then added with TEA (8.5 mL, 61.0 mmol). After they were all dissolved, the mixture was added into a solution of 1-hydroxynonane-4,6-dione and then stirred for 12 hrs at 40° C. The reaction progress and completion were confirmed by TLC. Upon completion of the reaction, while the temperature was kept at room temperature, the solvent was removed under reduced pressure. The reaction residue was diluted with EtOAc, and added with water. The aqueous layer was extracted with EtOAc and the organic layer was dried with anhydrous MgSO$_4$ and filtered and concentrated under reduced pressure. The concentrate was separated by column chromatography (Ether:Hexane=1:1) to obtain target 1.686 g (37%) of compound (formula 6a) and 1.540 g (34%) of target compound (formula 6b).

3-(1-tert-butyl-5-propyl-1H-pyrazol-3-yl)propan-1-ol (formula 6a)

$^1$H NMR (400 MHz, MeOH-$d_4$) δ 5.94 (s, 1H), 3.58 (t, 2H, J=6.5 Hz), 2.78 (t, 2H, J=7.7 Hz), 2.60 (t, 2H, J=7.6 Hz), 1.88-1.78 (m, 2H), 1.78-1.64 (m, 2H), 1.60 (s, 9H), 1.04 (t, 3H, J=7.5 Hz).

3-(1-tert-butyl-3-propyl-1H-pyrazol-5-yl)propan-1-ol (formula 6b)

$^1$H NMR (400 MHz, CDCl$_3$) δ 5.88 (s, 1H), 3.74 (t, 2H, J=6.2 Hz), 2.87 (t, 2H, J=7.8 Hz), 2.53 (t, 2H, J=7.8 Hz), 1.98-1.86 (m, 2H), 1.69-1.53 (m, 2H), 1.61 (s, 9H), 0.96 (t, 3H, J=7.3 Hz).

Reference Example 4

3-(1-tert-butyl-5-(4-chlorophenyl)-1H-pyrazol-3-yl)propanal (Formula 2)

3-(1-tert-butyl-5-(4-chlorophenyl)-1H-pyrazol-3-yl)propan-1-ol (200 mg, 0.774 mmol), PCC (334 mg, 1.548 mmol), SiO$_2$ (334 mg) was added with 5 mL of CH$_2$Cl$_2$ under nitrogen atmosphere and stirred for 5 hrs at room temperature. The progress and completion of the reaction were confirmed by means of TLC. Upon completion of the reaction, the reaction mixture was cooled down to room temperature and the solvent was removed from the reaction mixture under reduced pressure. The reaction mixture was diluted with EtOAc, and added with water. The aqueous layer was extracted with EtOAc and the organic layer was dried with anhydrous MgSO$_4$ and filtered. The resulting filtrate was concentrated under reduced pressure and the resulting concentrate was passed through column chromatography (Ether:Hexane=2:3, v/v) to obtain 149 mg (75%) of target compound.

$^1$H NMR (400 MHz, CDCl$_3$) δ 9.88 (t, 1H, J=1.6 Hz), 7.38-7.33 (m, 2H), 7.27-7.23 (m, 2H) 5.91 (s, 1H), 2.98 (t, 2H, J=7.2 Hz), 2.85-2.78 (m, 2H), 1.41 (s, 9H)

EXPERIMENTAL EXAMPLES

Experimental Example 1

Measurement of Affinity for Dopamine D$_4$ Receptor

Compounds represented by the above formula 1 were measured of their affinities for dopamine D$_4$ receptor by the method described below.

The affinities of the compounds for dopamine D$_4$ receptor were measured by using human recombinant dopamine D$_{4.2}$ receptor (PerkinElmer Life and Analytical Sciences, USA) expressed in CHO-K1 cells, and [$^3$H]YM-09151-2 (PerkinElmer) was used as a radioactive ligand.

50 mM Tris-HCl (pH 7.4) containing 120 mM NaCl, 5 mM KCl, 5 mM MgCl$_2$ and 1 mM EDTA was used as a buffer solution for the analysis of receptor binding. [$^3$H]YM-09151-2 binding reactions were performed in a 96-well plate format.

For drug screening, a reaction mixture with a final volume of 0.25 mL was prepared by mixing a compound of the present invention, D$_4$ receptor membrane (43 μg/well), [$^3$H]YM-09151-2 (0.1 nM), 50 mM Tris-HCl (pH 7.4) and the like. The reaction mixture was incubated for 120 min at 25° C., and then promptly passed through Wallac GF/C glass fiber filter (Wallac, Finland), which was already wetted in 0.5% PEI, by using Inotech harvester (Inotech) to terminate the reaction, and then washed with cold 50 mM Tris-HCl buffer solution. The filter was then covered with MeltiLex, sealed in a sample bag, and then dried in an oven. The radioactivity retained in the filter was finally counted using MicroBeta Plus, Wallac.

The affinity (IC50) of a compound for the receptor was calculated via nonlinear regression analysis of sigmoidal dose-response equation with the data obtained from three independent experiments (GraphPad Prism Program, San Diego, USA), which are carried out using 7-8 different concentrations of the compound in duplicate. Nonspecific binding was measured in the presence of 10 μM clozapine.

As shown in the Table 1, compounds 155, 156, 159, 160, 163 and 177 showed very high affinities for dopamine D$_4$ receptor (IC$_{50}$<10 nM).

TABLE 1

| Tested Compound | D$_4$ receptor affinity (IC$_{50}$, nM) |
|---|---|
| Compound 155 | 5.9 |
| Compound 156 | 3.5 |
| Compound 159 | 1.3 |
| Compound 160 | 2.9 |
| Compound 163 | 7.7 |
| Compound 177 | 8.0 |

Experimental Example 2

Evaluation of Selectivity on Dopamine D$_4$ Receptor

In order to evaluate the selectivity of the compounds which showed superior affinities for dopamine D$_4$ receptor in Experimental Example 1 above, their affinities for the other dopamine receptor isotypes and serotonin receptors were measured, respectively.

2-1: Measurement of Affinities for Dopamine Receptor Isotypes (D$_2$ & D$_3$)

Human recombinant dopamine D$_2$ and D$_3$ receptors, which were expressed in CHO cell lines, respectively, were purchased from PerkinElmer and Euroscreen, respectively. The affinities for D$_2$ and D$_3$ dopamine receptors were determined by adding receptor membrane (3 and 1 ug/well, respectively), radioactive isotope [$^3$H] spiperone (0.5 and 0.8 nM, respectively) and a test compound to a buffer solution, and subsequently incubating for 60 min at 27° C., and finally measuring the radioactivity using Inotech Harvester after filtration same as in Experimental Example 1 above.

50 mM Tris-HCl (pH 7.4) containing 10 MgCl$_2$ and 1 mM EDTA was used as a buffer solution for the measurement of affinity for dopamine D$_2$ receptor. 50 mM Tris-HCl (pH 7.4) containing 5 mM MgCl$_2$, 5 mM EDTA, 5 mM KCl, 1.5 mM CaCl$_2$ and 120 mM NaCl was used as a buffer solution for the measurement of affinity for dopamine D$_3$ receptor. For measurement of non-specific binding, 10 μM haloperidol (haloperidol) was used.

2-2: Measurement of Affinity for Serotonin 5-HT Receptor Family

The measurement of affinity for serotonin 5-HT receptor family was performed according to the experimental conditions as specified in Table 2 below using the method same as in Experimental Example 1 above.

The detailed conditions of the analysis are shown in Table 2 below.

TABLE 2

Conditions for analysis of serotonin receptor binding experiment

| Receptor | $5\text{-}HT_{1A}$ | $5\text{-}HT_{2A}$ | $5\text{-}HT_{2C}$ | $5\text{-}HT_6$ | $5\text{-}HT_7$ |
|---|---|---|---|---|---|
| Receptor membrane source | Stable CHO or HEK-293 cell lines expressing human or rat recombinant receptors | | | | |
| Buffer solution | 50 mM Tris-HCl (pH 7.4), 10 mM $MgSO_4$, 0.5 mM EDTA, 0.1% ascorbic acid | 50 mM Tris-HCl (pH 7.4) | 50 mM Tris-HCl (pH 7.7), 0.1% ascorbic acid, 10 μM pargyline | 50 mM Tris-HCl (pH 7.4), 10 mM $MgCl_2$, 0.5 mM EDTA | |
| Final Volume | 250 μL | | | | |
| Radioactive ligand | [$^3$H]8-OH-DPAT, 0.5 nM | [$^3$H]ketanserin 1 nM | [$^3$H]Mesulergine 1 nM | [$^3$H] LSD 1.8 nM | [$^3$H] LSD 3 nM |
| Non-specific binding | methiothepin 0.5 μM | mianserin 1 μM | methiothepin 10 μM | | |
| Culture | 60 min at 27° C. | 15 min at 37° C. | 30 min at 37° C. | 60 min at 37° C. | 90 min at 27° C. |
| Filtration | GF/C 0.5% PEI | GF/C 0.05% Brij | GF/C 1% BSA | GF/C 0.5% PEI | |

The results of affinity measurements of compounds of the present invention for dopamine and serotonin receptor isotypes are shown in Table 3.

TABLE 3

Receptor affinity ($IC_{50}$, nM)

| Tested Compounds | $D_2$ | $D_3$ | $5\text{-}HT_{1A}$ | $5\text{-}HT_{2A}$ | $5\text{-}HT_{2C}$ | $5\text{-}HT_6$ | $5\text{-}HT_7$ |
|---|---|---|---|---|---|---|---|
| Compound 155 | 5264 | 461 | 109 | 35 | 671 | >10000 | 259 |
| Compound 156 | 696 | 87 | 126 | 152 | 1396 | >10000 | 313 |
| Compound 159 | 2046 | 131 | 413 | 8 | 154 | 2504 | 195 |
| Compound 160 | 3794 | 229 | 50 | 65 | 141 | 2014 | 84 |
| Compound 163 | 1056 | 420 | 494 | 45 | 558 | 617 | 651 |
| Compound 177 | 227 | 687 | 37 | 27 | 505 | 9214 | 252 |

As shown in Table 3 above, compounds 155, 156, 159, 160, 163 and 177 of the present invention showed poor affinities for dopamine receptor isotypes (D2 & D3) and serotonin receptors. In particular, they showed extremely poor affinity for D2 receptors, which are very closely associated with adverse reactions induced by a therapeutic agent for schizophrenia.

Further, the above compounds also showed relatively poor affinity for serotonin receptors ($5\text{-}HT_{1A}$-$5\text{-}HT_7$) except for $5\text{-}HT_{2A}$ receptor. Therefore, the compounds of 155-177 of the present invention were confirmed to have superior selectivity for $D_4$ receptors.

Experimental Example 3

Measurement of Influences on Apomorphine-Induced Behavior in Mice

To evaluate the effect of the compounds of the present invention against schizophrenia, which were shown to have excellent affinity for receptors in the above Table 1, the inhibitory effects of the compounds on apomorphine-induced psychiatric behavior, cage climbing, in mice were measured.

When mice were treated with apomorphine (1 mg/kg, sc), a potent dopamine receptor agonist, and were put into cylindrical cages (diameter, 12 cm/height, 14 cm) with the floor and wall consisting of metal bars and covered with a lid, they begin to perform repeatedly a psychotic behavior of 'cage climbing'. Their climbing behaviors were monitored every 10 min for 30 min and scored by 4-point rating scale (0~3 points) depending on the extent of the behavior (Costentin, J. et al., *Nature* 1975, 257, 405-7; Protais, P. et al., *Psychopharmacology* 1976, 50, 1-6).

The compounds were injected intraperitoneally into mice 30 min prior to apomorphine administration. The inhibitory effects of the compounds against control group were measured and each $ED_{50}$ was calculated therefrom.

The compounds 155, 156, 157, 159, 160 and 177 of the present invention significantly inhibited the psychotic behavior induced by apomorphine ($ED_{50}$: 8.8-14.5 mg/kg, ip). In fact, their effects were a little bit less than that of clozapine (4 mg/kg, ip), the most effective $D_4$ receptor antagonist for schizophrenia at present, thus proving that they have an excellent effect on treating psychotic diseases. $ED_{50}$ of each compound is shown in Table 4 below.

TABLE 4

Effects of Compounds of the present invention on psychotic diseases

| Tested Compounds | Inhibitory effects on apomorphine-induced climbing behavior $ED_{50}$ (mg/kg, ip) |
|---|---|
| Compound 155 | 10.7 |
| Compound 156 | 9.6 |
| Compound 157 | 14.5 |
| Compound 159 | 9.1 |
| Compound 160 | 10.6 |
| Compound 177 | 8.8 |
| clozapine (reference compound) | 4.0 |

Experimental Example 4

Effects on Rotarod Deficit in Mice

Rotarod test was performed to evaluate the effect of the compounds of the present invention on extrapyramidal side effects in mice as follows (Dunham, N. W. et al., *J. Am. Pharm. Assoc.* 1957, 46, 208-209). Each mouse was administered with a test drug, and then placed on a 1 inch diameter knurled plastic rod rotating at 6 rpm (Ugo-Basile, Milano, Italy), and the rotarod deficit (%) was obtained by counting the number of mice fallen from the rotating rod within 1 min at 30, 60, 90, and 120 min after the administration of the drug. The median neurotoxic dose ($TD_{50}$) was determined as the dose at which 50% of the mice showed rotarod deficit.

TABLE 5

| Tested Compound | Rotarod deficit $TD_{50}$ (mg/kg, ip) |
|---|---|
| Compound 155 | 28.5 |
| Compound 156 | 26.0 |
| Compound 157 | 50.1 |
| Compound 159 | 35.3 |
| Compound 160 | 24.6 |
| Compound 177 | 19.4 |
| clozapine | 3.9 |

As shown in the above Table 5, the compounds 155, 156, 157, 159, 160 and 177 of the present invention showed about 20-50 mg/kg (ip) of rotarod deficit $TD_{50}$. This is about 2.2-5 times of $ED_{50}$ for antipsychotic efficacy, and thus the above compounds were proved to be relatively safe as a drug working on central nervous system with low extrapyramidal side effects (EPS). In case of clozapine, a reference drug, there were observed adverse effects at dosage showing efficacies as shown in the above table ($ED_{50}$ and $TD_{50}$ are almost same).

Therefore, the compounds of the present invention are shown to be a safe drug having less adverse effects than those of clozapine, a reference drug.

MANUFACTURING EXAMPLES

The compounds of the present invention represented by the above formula 1 can be formulated in various forms. The followings are embodiments of formulation methods comprising the above compounds as active ingredient. However, they should not be construed as limiting the scope of the present invention.

Formulation 1

Preparation of Tablets 100 mg of a compound of the present invention or its pharmaceutically acceptable salt, 100 mg of corn starch, 100 mg of lactose and 2 mg of stearate magnesium were mixed and formulated into tablets according to a conventional tableting method.

Formulation 2

Preparation of Capsules 100 mg of a compound of the present invention or its pharmaceutically acceptable salt, 100 mg of corn starch, 100 mg of lactose and 2 mg of stearate magnesium were mixed and formulated into capsules according to a conventional capsulation method by filling the ingredients into a gelatin capsule.

Formulation 3

Preparation of Powder 2 g of a compound of the present invention or its pharmaceutically acceptable salt and 1 g of corn starch were mixed and filled into a sealing to be formulated into powder.

INDUSTRIAL APPLICABILITY

The piperazinyl-propyl-pyrazole derivatives of the present invention represented by the above formula 1 are shown to have excellent binding affinities for dopamine $D_4$ receptor. They are also shown to effectively inhibit psychotic behavior (cage climbing) in mice induced by apomorphine. Further, they have shown relatively low level of adverse effects in mice rotarod test, thus being expected to be very useful as a therapeutic agent for the prevention and treatment of schizophrenia, attention deficit hyperactivity disorder, depression, stress diseases, panic disorder, phobia, obsessive-compulsive disorder, posttraumatic stress disorder, cognitive disorder, Alzheimer's disease, Parkinson's disease, anxiety, paraphrenia, mania, seizure disorder, personality disorder, migraine, drug addiction, alcohol addiction, obesity, eating disorder, sleeping disorder and the like.

What is claimed is:

1. A piperazinyl-propyl-pyrazole derivative or its pharmaceutically acceptable salt represented by the following formula 1:

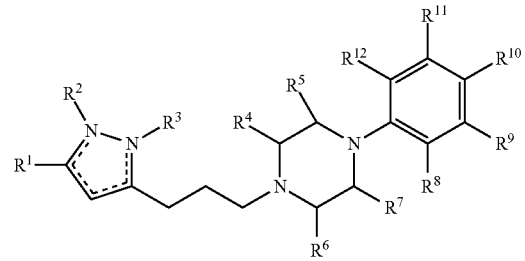

wherein R1 is a C1-C10 alkyl group, or a substituted or unsubstituted aryl or heteroaryl group;
one of R2 and R3 is a C1-C10 alkyl group, benzyl group, or substituted or unsubstituted aryl or heteroaryl group, such that only one of R2 and R3 is present which would result in a pyrazole ring;
R4, R5, R6 and R7, being same or different with one another, are independently a hydrogen atom or a C1-C10 alkyl group;
R8, R9, R10, R11 and R12, being same or different with one another, are independently a hydrogen atom, a halogen atom, a C1-C10 alkyl group, a C1-C10 alkoxy group, a bis(substituted or unsubstituted aryl)alkylene group, a benzyl group, a nitro group, a hydroxy group, a cyano group, an amino group, a mono or dialkylamino group, an alkylcarbonylamino group, an aminosulfonyl group, a mono or dialkylaminosulfonyl group, an alkylcarbonyl group, or an alkyloxycarbonyl group;
the dotted line represents a single bond or a double bond which depends on the presence of either R2 or R3 to maintain the aromaticity of a pyrazole ring;
said aryl group represents a phenyl group, said heteroaryl group represents a thiophenyl group or a pyridyl group, and said substituted aryl or heteroaryl group represents an aryl or a heteroaryl group with from 1 to 3 substituents selected from the group consisting of a halogen atom, a nitro group, a C1-C10 alkyl group, a C1-C10 alkoxy group, a C1-C10 haloalkyl group, and a C1-C10 haloalkoxy.

2. The piperazinyl-propyl-pyrazole derivative or its pharmaceutically acceptable salt of claim 1, wherein said R1 is a C1-C10 alkyl group, a substituted or unsubstituted phenyl group, or a substituted or unsubstituted thiophenyl group;

one of R2 and R3 is a C1-C10 alkyl group, benzyl group, a substituted or unsubstituted phenyl group, or a substituted or unsubstituted pyridyl group, such that only one of R2 and R3 is present which would result in a pyrazole ring;

R4, R5, R6 and R7, being same or different with one another, are independently a hydrogen atom or a C1-C10 alkyl group;

R8, R9, R10, R11 and R12, being same or different with one another, are independently a hydrogen atom, a halogen atom, a C1-C10 alkyl group, a C1-C10 alkoxy group, bis(substituted or unsubstituted phenyl)alkylene group, or a benzyl group;

the dotted line represents a single bond or a double bond which depends on the substitution of R2 and R3 but maintains the aromaticity of a pyrazole ring;

said substituted phenyl group, thiophenyl group or pyridyl group are independently a phenyl group, a thiophenyl group or a pyridyl group with from 1 to 3 substituents selected from the group consisting of a halogen atom, a nitro group, a C1-C10 alkyl group, a C1-C10 alkoxy group, a C1-C10 haloalkyl group, and a C1-C10 haloalkoxy group.

3. The piperazinyl-propyl-pyrazole derivative or its pharmaceutically acceptable salt of claim 1, wherein said R1 is phenyl, 4-methylphenyl, 4-chlorophenyl, 4-fluorophenyl, 4-methoxyphenyl, 2-thiophenyl, methyl, ethyl, propyl, isopropyl, butyl, or isobutyl;

one of R2 and R3 is t-butyl, benzyl, phenyl, 3-nitrophenyl, 4-nitrophenyl, 3-chlorophenyl, 4-fluorophenyl, 4-methylphenyl, 4-methoxyphenyl, 4-trifluoromethylphenyl, 4-trifluoromethoxyphenyl, or 2-pyridyl, such that only one of R2 and R3 is present which would result in a pyrazole ring;

R4, R5, R6 and R7, being same or different with one another, are independently a hydrogen atom or a methyl group;

R8, R9, R10, R11 and R12, being same or different with one another, are independently a hydrogen atom, a chloro, fluoro, methyl, methoxy, or bis(4-fluorophenyl) methylene.

4. The piperazinyl-propyl-pyrazole derivative or its pharmaceutically acceptable salt of claim 1, wherein said pharmaceutically acceptable salt is produced by reacting said derivative represented by the above formula 1 with an inorganic acid, an organic acid, an amino acid, sulfonic acid, an alkali metal or ammonium ion.

5. A method of preparing a piperazinyl-propyl-pyrazole derivative represented by the following formula 1 by performing reductive amination between a pyrazole aldehyde derivative represented by the following formula 2 and a piperazine derivative represented by the following formula 3:

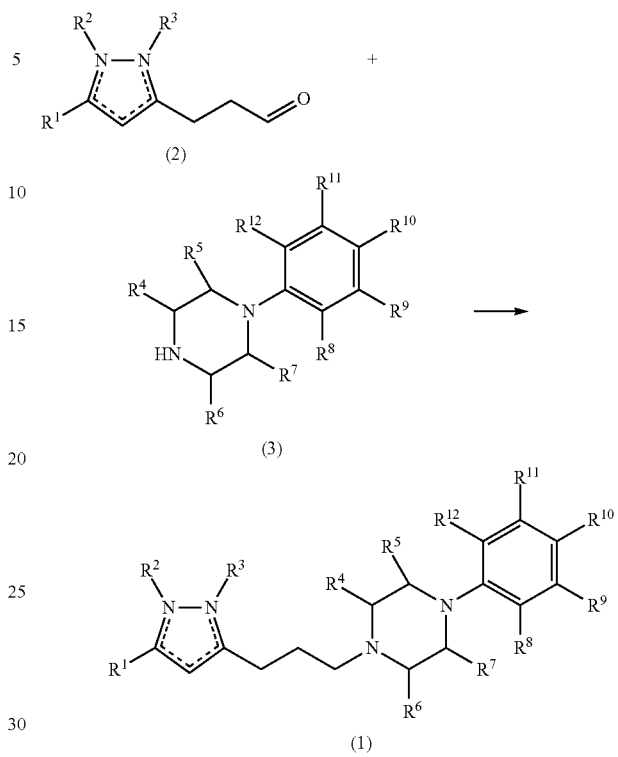

wherein, in the above reaction scheme I, R1, R2, R3, R4, R5, R6, R7, R8, R9, R10, R11 and R12 are same as defined in claim 1.

6. The method of claim 5, wherein said reductive amination is performed in the presence of a molecular sieve, a reducing agent and a base.

7. A pharmaceutical composition for the treatment of central nervous system disorders comprising a compound selected from claim 1.

8. A pharmaceutical composition for the treatment of central nervous system disorders comprising a compound selected from claim 2.

9. A pharmaceutical composition for the treatment of central nervous system disorders comprising a compound selected from claim 3.

10. A pharmaceutical composition for the treatment of central nervous system disorders comprising a compound selected from claim 4.

* * * * *